US007479547B2

(12) United States Patent
Williamson et al.

(10) Patent No.: US 7,479,547 B2
(45) Date of Patent: Jan. 20, 2009

(54) HIV-1 SUBTYPE ISOLATE REGULATORY/ACCESSORY GENES, AND MODIFICATIONS AND DERIVATIVES THEREOF

(75) Inventors: Carolyn Williamson, Cape Town (ZA); Joanne Heidi van Harmelen, Cape Town (ZA); Clive Maurice Gray, Johannesburg (ZA); William Bourn, Cape Town (ZA); Salim Abdool Karim, Durban (ZA)

(73) Assignees: The South African Medical Research Council, Cape Town (ZA); University of Cape Town, Cape Town (ZA)

( * ) Notice: Subject to any disclaimer, the term of this patent is extended or adjusted under 35 U.S.C. 154(b) by 433 days.

(21) Appl. No.: 10/494,131

(22) PCT Filed: Oct. 31, 2002

(86) PCT No.: PCT/IB02/04550

§ 371 (c)(1),
(2), (4) Date: Aug. 24, 2004

(87) PCT Pub. No.: WO03/037919

PCT Pub. Date: May 8, 2003

(65) Prior Publication Data

US 2005/0176929 A1 Aug. 11, 2005

(30) Foreign Application Priority Data

Oct. 31, 2001 (ZA) .................................. 2001/8978

(51) Int. Cl.
C07H 21/02 (2006.01)
C12N 5/00 (2006.01)
A61K 39/00 (2006.01)
A61K 38/00 (2006.01)

(52) U.S. Cl. ................ 536/23.1; 435/320.1; 424/184.1; 424/192.1; 530/300

(58) Field of Classification Search ........................ None
See application file for complete search history.

(56) References Cited

FOREIGN PATENT DOCUMENTS

| WO | WO 00/26416 | | 5/2000 |
|---|---|---|---|
| WO | WO 02/04493 | A2 | 1/2002 |
| WO | WO 02/04494 | A2 | 1/2002 |
| WO | WO 02/04494 | A3 | 1/2002 |
| WO | WO 02/04993 | A2 | 1/2002 |
| WO | WO 02/04993 | A3 | 1/2002 |
| WO | WO 02/22080 | A2 | 3/2002 |
| WO | WO 03/004620 | A2 | 1/2003 |
| WO | WO 03/004657 | A1 | 1/2003 |
| WO | WO 03/037919 | A3 | 5/2003 |

OTHER PUBLICATIONS

Mashishi TN et al. HIV-1 isolate ZADU151 from south africa nef gene. Entrez Accession No. AF397535.*
Gao, F. et al., "Molecular Cloning and Analysis of Functional Envelope Genes from Human Immunodeficiency Virus Type 1 Sequence Subtypes A through G," Journal of Virology, vol. 70, No. 3, 1651-1667, 1996, GENPEPT ANGIS Sequence, Accession No. AAB61130, and EMBL ANGIS Sequence, Accession No. HIUU52953.
Gao, F. et al., "Codon Usage Optimization of HIV Type 1 Subtype C *gag, pol, env*, and *nef* Genes: In Vitro Expression and Immune Responses in DNA-Vaccinated Mice," AIDS Research and Human Retroviruses, vol. 19, No. 9, 817-823, 2003, GENBANK ANGIS Sequence, Accession No. AY181198, and GENPEPT ANGIS Sequence, Accession No. AA065396.
GENBANK ANGIS Sequence, Accession No. AF075702, (Definition)—HIV-1 Isolate SE8603 from Uganda, complete genome, Submitted (Jul. 1, 1998) by Department of Infectious Disease Epidemiology, National Public Health Institute, Mannerheimintie 166, Helsinki FIN-00300, Finland, Web page available at www1.angis.org.au/bin/WebANGIS/QueryDB/qdb-?BrowseCode, as available via the Internet and printed Feb. 18, 2004.
GENPEPT ANGIS Sequence, Accession No. AAD41673, (Definition)—HIV-1 isolate SE8603 from Uganda, complete genome, Submitted (Jul. 1, 1998) Department of Infectious Disease Epidemiology, National Public Health Institute, Mannerheimintie 166, Helsinki FIN-00300, Finland, Web page available at www.1angis.org.au/bin/WebANGIS/QueryDB/qdb?do_call. pl+4615+AAD41673, as available via the Internet and printed Feb. 18, 2004.
GENPEPT ANGIS Sequence, Accession No. AAL05314, (Definition)—HIV-1 Isolate Du151 from South Africa, partial genome, AIDS Research and Human Retroviruses, vol. 17, No. 16, 1527-1531, 2001, Web page available at www1.angis.org.au/bin/WebANGIS/QueryDB/qdb?do_call.pl+4615+AAL05314, as available via the Internet and printed Feb. 18, 2004.
GENBANK ANGIS Sequence, Accession No. AY043173, (Definition)—HIV-1 Isolate Du151 from South Africa, partial genome, AIDS Research and Human Retroviruses, vol. 17, No. 16, 1527-1531, 2001, Web page available at www1.angis.org.au/bin/WebANGIS/QueryDB/qdb?do_call.pl+genback+AY04317, as available via the Internet and printed Feb. 17, 2004.
Index of Lab Research, web page at web.archive.org/web/20021121171118/www.aids.har.../consensus_sequence, as available via the Internet and printed Feb. 27, 2004.
Jubier-Maurin, V. et al., "Genetic Characterization of the *nef* Gene from Human Immunodeficiency Virus Type 1 Group M Strains Representing Genetic Subtypes A, B, C, E, F, G, and H," AIDS Research and Human Retroviruses, vol. 15, No. 1, 23-32, 1999, GENBANK ANGIS Sequence, Accession No. HIV232977, and GENPEPT ANGIS Sequence, Accession No. CAA13458.

(Continued)

*Primary Examiner*—Zachariah Lucas
*Assistant Examiner*—Bo Peng
(74) *Attorney, Agent, or Firm*—Kilpatrick Stockton LLP

(57) ABSTRACT

The invention describes HIV-1 subtype isolate regulatory/accessory genes, and modifications and derivatives thereof. The genes which are described are the tat, nef and rev genes. Consensus amino acid sequences are also disclosed. The invention also relates to a vaccine including two or more of the nucleotide sequences, and nucleotide sequences from the pol and/or gag genes of HIV-1.

7 Claims, 26 Drawing Sheets

OTHER PUBLICATIONS

Kong, W-P. et al., "Immunogenicity of Multiple Gene and Clade Human Immunodeficiency Virus Type 1 DNA Vaccines," Journal of Virology, vol. 77, No. 23, 12764-12772, 2003.

Lole, K. et al., "Full-Length Human Immunodeficiency Virus Type 1 Genomes from Subtype C-Infected Seroconverters in India, with Evidence of Intersubtype Recombination," Journal of Virology, vol. 73, No. 1, 152-160, 1999, GENBANK ANGIS Sequence, Accession No. AF067154, and GENPEPT ANGIS Sequence, Accession No. AAD12078.

Mashishi, T. et al., "Conserved Domains of Subtype C Nef from South African HIV Type 1-Infected Individuals Include Cytotoxic T Lymphocyte Epitope-Rich Regions," AIDS Research and Human Retroviruses, vol. 17, No. 17, 1681-1687, 2001, GENBANK ANGIS Sequence, Accession No. AF397535, GENPEPT ANGIS Sequence, Accession No. AAK98474, GENBANK ANGIS Sequence, Accession No. AF397542, and GENPEPT ANGIS Sequence, Accession No. AAK98481.

Okuda, K. et al., "Induction of Potent Humoral and Cell-Mediated Immune Responses Following Direct Injection of DNA Encoding the HIV Type 1 *env* and *rev* Gene Products," AIDS Research and Human Retroviruses, vol. 11, No. 8, 933-943, 1995.

Rodenburg, C. et al., "Near Full-Length Clones and Reference Sequences for Subtype C Isolates of HIV Type 1 from Three Different Continents," AIDS Research and Human Retroviruses, vol. 17, No. 2, 161-168, 2001, GENBANK ANGIS Sequence, Accession No. AF286227, GENPEPT ANGIS Sequence, Accession No. AAK30998, GENBANK ANGIS Sequence, Accession No. AF286225, and GENPEPT ANGIS Sequence, Accession No. AAK30980.

Novitsky, V., et al., "Human Immunodeficiency Virus Type 1 Subtype C Molecular Phytogeny: Consensus Sequence for an AIDS Vaccine Design?" Journal of Virology, vol. 76, No. 11, Jun. 2002, pp. 5435-5451, XP002248733.

Harvard AIDS Institute Online—Jun. 2002, XP002248734, Retrieved from the Internet: www.aids.Harvard.edu/lab_research/consensus_sequence/Tat.pdf>. Retrieved on Jul. 22, 2003.

Van Harmelen, J. et al., "Characterization of Full-Length HIV Type 1 Subtype C Sequences from South Africa." AIDS Research and Human Retroviruses, vol. 17, No. 16, Nov. 1, 2001, pp. 1527-1531, XP002248735.

Database EBI Online—Nov. 13, 2001; Van Harmelen, J. et al., "HIV-1 Isolate Du422 From South Africa, Partial Genome," Database Accession No. AY043175; XP002248737.

Database EBI Online—Nov. 13, 2001; Van Harmelen, J. et al., "HIV-1 Isolate Du151 From South Africa, Partial Genome," Database Accession No. AY043173; XP002248738.

Database EBI Online—Dec. 1, 2001; Van Harmelen, J. et al., "HIV-1 Tat Protein From Strain Du422," Database Accession No. Q901X5; XP002248739.

Database EBI Online—Dec. 1, 2001; Van Harmelen, J. et al., "HIV-1 Tat Protein From Strain Du151," Database Accession No. Q901Z3; XP002248740.

Database EBI Online—Aug. 19, 1998, Cheng-Mayer, C. et al., "HIV-1 Tat and Rev1 Genes, Second Exons," Database Accession No. M66535, XP002248741.

Los Alamos HIV Database Online—Dec. 1996, XP002248803, Retrieved from the Internet: www.hiv-web.lanl.gov/content/hiv-db/COMPENDIUM/1996/PART-I/tat.pdf>. Retrieved on Jul. 23, 2003.

Los Alamos HIV Database Online—Dec. 1996, XP002248804, Retrieved from the Internet: www.hiv-web.lanl.gov/content/hiv-db/COMPENDIUM/1996/PART-I/tat.pdf>. Retrieved on Jul. 23, 2003.

Williamson, C. et al., "Designing HIV-1 Subtype C Vaccines For South Africa," South African Journal of Science, Associated Scientific and Technical Societies of South Africa, SA, vol. 96, No. 6, Jun. 2000, pp. 318-324, XP008009291.

Novitsky, V. et al., "Molecular Cloning and Phylogenetic Analysis of Human Immunodeficiency virus Type 1 Subtype C: A Set of 23 Full-Length Clones From Botswana," Journal of Virology, US, vol. 73, No. 5, May 1999, pp. 4427-4432, XP002144689.

Megede, J. et al., "Increased Expression and Immunogenicity of Sequence-Modified Human Immunodeficiency virus Type 1 *gag* Gene," Journal of Virology, US, vol. 74, No. 6, Mar. 2000, pp. 2628-2635, XP000980650.

\* cited by examiner

```
ATGGAGCCAATAGATCCTAACCTAGAGCCCTGGAACCATCCAGGAAGTCAGCCTAATACT  60
CCTTCTAATAACTGCTATTGTAAACACTGTAGCTACCATTGTCTAGTTTGCTTTCAGACA  120
AAAGCCTTAGGCATTTCCTATGGCAGGAAGAAGCGGAGACAGCGACGAAGCACTCCTCCA  180
AGCAGTGAAGATCATCAAAATCCTATATCAAAGCAACCCTTATCCCAAACCCGAGGGGAC  240
CCGACAGGCTCGGAAGAATCGAAGAAGAAGGTGGAGAGCAAGACAAAGACAGATCCATTC  300
GATTAG                                                        306
```

Figure 1

```
MEPIDPNLEPWNHPGSQPNTPCNNCYCKHCSYHCLVCFQTKGLGISYGRKKRRQRRSTPP  60
SSEDHQNPISKQPLSQTRGDPTGSEESKKKVESKTKTDPFD                    101
```

Figure 2

```
ATGGAGCCAATAGATCCTAACCTAGAGCCCTGGAACCATCCAGGAAGTCAACCTAACACT  60
CCTTGTACTAAATGCTATTGTAAATACTGCAGCTATCATTGTCTAGTTTGCTTTCAGACA  120
AAAGCCTTAGGCATTTCCTATGGCAGGAAGAAGCGGACACAGCGACGAAGCACTCCTCCA  180
AGCAGTGAGGATCATCAAAATCTTATATCAGAGCAGCCCTTACCCCAAGCCCGAGGGGTC  240
CCGACAGGCTCGGAAGAATCGAAGAAGAAGGTGGAGAGCAAGACAAAAACAGATCCATTC  300
GATTAG                                                        306
```

Figure 3

```
MEPIDPNLEPWNHPGSQPNTPCTKCYCKYCSYHCLVCFQTKGLGISYGRKKRRQRRSTPP  60
SSEDHQNLISEQPLPQARGVPTGSEESKKKVESKTKTDPFD                    101
```

Figure 4

```
ATGGGGGGCAAGTGGTCAAAAAGCAGCATAGTGGGATGGCCTGCTGTAAGAGAAAGAATA  60
AGAAGAACTGAGCCAGCAGCAGAGGGAGTAGGACCAGCATCTCAAGACTTAGATAAACAT  120
GGAGCGCTTACAAGCAGCAACACAGCCCACAATAATCCTGACTGTGCCTGGCTACAAGCA  180
CAAGAGGAGGAAGAAGACGTAGGTTTTCCAGTCAGACCTCAGGTGCCTCTAAGACCAATG  240
ACTTATAAGGCAGCATTCGATCTCAGCTTCTTTTTAAAAGAAAAGGGGGACTGGAAGGG  300
TTAATTCACTCTAAGAGAAGACAAGACATTCTTGATTTGTGGGTCTATCACACACAAGGC  360
TACTTCCCTGATTGGCAAAACTACACGCCGGGACCAGGAGTCAGATACCCACTGACCTTT  420
GGATGGTGCTTCAAGCTAGTGCCAGTTGATCCAAGGGAAGTAGAAGAGGCCAACAAAGGA  480
GAAAACAACTGTTTGCTACACCCTATGAGCCAGCATGGAATGGAGGATGCAGACAGAGAA  540
GTATTAAGATGGGTGTTTGACAGCAGTCTAGCACGCAGACACCTGGCCCGCGAGAAACAT  600
CCGGAGTATTACAAAGAC                                            618
```

Figure 5

```
MGGKWSKSSIVGWPAVRERIRRTEPAAEGVGAASQDLDKHGALTSSNTAHNNPDCAWLQA60
QEEEPEVGFPVRPQVPLRPMTYKAAFDLSFFLKEKGGLEGLIYSKKRQDILDLWVYHTQG120
YFPDWQNYTPGPGVRLPLTFGWCFKLVPVDPEEVEEANKGENNCLLHPLSQHGMEDADRE180
VLKWVFDSSLARRHLAREKHPEYYKDC                                 207
```

Figure 6

```
ATGGCAGGAAGAAGCGGAGACAGCGACGAAGCACTCCTCCAAGCAGTGAAGATCATCAAA60
ATCCTATATCAAAGCAACCCTTATCCCAAACCCGAGGGGACCCGACAGGCTCGGAAGAAT120
CGAAGAAGAAGGTGGAGAGCAAGACAAGACAGATCCATTCGATTAGTGAGCGGATTCTT180
AGCACTTGCCTGGGACGATCTGCGGAGCCTGTGCCTCTTCAGCTACCACCAATTGAGAGA240
CTTCATATTGACTGCAGCGAGAGCAGCGGAACTTCTGGGACGCAGCAGTCTCAGGGGACT300
GCAGAGAGGGTGGGAAGTCCTTAA                                    324
```

Figure 7

```
MAGRSGDSDEALLQAVKIIKILYQSNPYPKPEGTRQARKNRRRRWRARQRQIKSISERIL60
STCLGRSAEPVPLQLPPIERLHIDCSESSGTSGTQQSQGTAERVGSP            107
```

Figure 8

```
GGATCCGCGG CCGCAAGCTT GCCACCATGG TAGGCATTTC CTATGGCAGG50
AAGAAGCGGA GACAGCGACG AAGCACTCCT CCAAGCAGTG AGGATCATCA100
AAATCCTATA TCAAAGCAGC CCTTACCCCA AACCCGAGGG GACCCGACAG150
GCTCGGAAGA ATCGAAGAAG AAGGTGGAGA GCAAGACAAA AACAGATCCA200
TTCGATTGTA AATACTGCAG CTATCATTGT CTAGTTTGCT TTCAGACAAA250
AGGCTTAGGT ATTAGCTATG GAAGGAAGAA ACGGATGGAG CCAATAGATC300
CTAACCTAGA GCCCTGGAAC CATCCAGGAA GTCAACCTAA CACTCCTTGT350
AATAAATGCT ATTGTAAGTA CTGTTCATAT CATTGCCTAG TT           392
```
Bold= Restriction sites and Kozac sequence engineered

Figure 9

```
GGATCCGCGG CCGCAAGCTT GCCACCATGG TGGGCATCAG CTACGGCCGC50
AAGAAGCGCC GCCAGCGCCG CAGCACCCCG CCCAGCAGCG AGGACCACCA100
GAACCCCATC AGCAAGCAGC CCCTGCCCCA GACCCGCGGC GACCCCACCG150
GCAGCGAGGA GAGCAAGAAG AAGGTGGAGA GCAAGACCAA GACCGACCCC200
TCCGACTGCA AGTACTGCAG CTACCACTGT CTGGTGTGCT TCCAGACCAA250
GGGCCTGGGC ATCTCCTACG GCGCAAGAA ACGGATGGAG CCCATCGACC300
CCAACCTGGA GCCCTGGAAC CACCCCGGCA GCCAGCCCAA CACCCCCTGC350
AACAAGTGCT ACTGCAAATA CTGCTCCTAC CACTGCCTCG TG           392
```
Bold= Restriction sites and Kozac sequence engineered

Figure 10

```
MLGISYGRKK RRQRRSTPFS SEDHQNPISK QPLPQTRGDP TGSEESKKKV⁵⁰
ESKTKTDPFD CKYCSYHCLV CFQTKGLGIS YGRKKRMEPI DPNLEPWNPP¹⁵⁰
GSQPNTPCNK CYCKYCSYHC LV                              ¹⁷²
```

Figure 11

```
GTGGGATGGC CTGCTGTAAG AGAAAGAATA AGAAGAACTG AGCCAGCAGC⁵⁰
AGAGGAGTA GGACCAGCAT CTCAAGACTT AGATAAACAT GGAGCGCTTA¹⁰⁰
CAAGCAGCAA CACAGCCCAC AATAATCCTG ACTGTGCCTG GCTACAAGCA¹⁵⁰
CAAGAGGAGG AAGAAGACGT AGGTTTTCCA GTCAGACCTC AGGTGCCTCT²⁰⁰
AAGACCAATG ACTTATAAGG CAGCATTCGA TCTCAGCTTC TTTTTAAAAG²⁵⁰
AAAAGGGGGG ACTGGAAGGG TTAATTCACT CTAAGAGAAG ACAAGACATT³⁰⁰
CTTGATTTGT GGGTCTATCA CACACAAGGC TACTTCCCTG ATTGGCAAAA³⁵⁰
CTACACGCCG GGACCAGGAG TCAGATACCC ACTGACCTTT GGATGGTGCT⁴⁰⁰
TCAAGCTAGT GCCAGTTGAT CCAAGGGAAG TAGAAGAGGC AACAAAGGA⁴⁵⁰
GAAAACAACT GTTTGCTACA CCCTATGAGC AGCATGGAA TGGAGGATGC⁵⁰⁰
AGACAGAGAA GTATTAAGAT GGGTGTTTGA CAGCAGTCTA GCACGCAGAC⁵⁵⁰
ACCTGGCCCG CGAGAAACAT CCGGAGTATT ACAAAGACTA GGAATTCTCT⁶⁰⁰
AGAGCGGCCG CGTCGAC                                    ⁶¹⁷
```

Bold= Restriction sites engineered

Figure 12

```
GTGGGCTGGC CCGCCGTGCG CGAGCGCATC CGCCGCACCG AGCCCGCCGC⁵⁰
CGAGGGCGTG GGCCCCGCCA GCCAGGACCT GGACAAGCAC GGCGCCCTGA¹⁰⁰
CCAGCAGCAA CACCGCCCAC AACAACCCCG ACTGCGCCTG GCTGCAGGCC¹⁵⁰
CAGGAGGAGG AGGAGGACGT GGGCTTCCCC GTGCGCCCCC AGGTGCCCCT²⁰⁰
GCGCCCCATG ACCTACAAGG CCGCCTTCGA CCTGAGCTTC TTCCTGAAGG²⁵⁰
AGAAGGGCGG CCTGGAGGGC CTGATCCACA GCAAGCGCCG CCAGGACATC³⁰⁰
CTGGACCTGT GGGTGTACCA CACCCAGGGC TACTTCCCCG ACTGGCAGAA³⁵⁰
CTACACCCCC GGCCCCGGCG TGCGCTACCC CCTGACCTTC GGCTGGTGCT⁴⁰⁰
TCAAGCTGGT GCCCGTGGAC CCCCGCGAGG TGGAGGAGGC CAACAAGGGC⁴⁵⁰
GAGAACAACT GCCTGCTGCA CCCCATGAGC AGCACGGCA TGGAGGACGC⁵⁰⁰
CGACCGCGAG GTGCTGCGCT GGGTGTTCGA CAGCAGCCTG GCCCGCCGCC⁵⁵⁰
ACCTGGCCCG CGAGAAGCAC CCCGAGTACT ACAAGGACTG AGAATTCTCT⁶⁰⁰
AGAGCGGCCG CGTCGAC                                    ⁶¹⁷
```

Bold= Restriction sites engineered

Figure 13

```
VGWPAVRERI RRTEPAAEGV GPASQDLDKH GALTSSNTAH NNPDCAWLQA⁵⁰
QEEEEDVGFP VRPQVPLRPM TYKAAFDLSF FLKEKGGLEG LIHSKRRQDI¹⁰⁰
LDLWVYHTQG YFPDWQNYTP GPGVRYPLTF GWCFKLVPVD PREVEEANKG¹⁵⁰
ENNCLLHPMS QHGMEDADRE VLRWVFDSSL ARRHLAREKH PEYYKD     ¹⁹⁶
```

Figure 14

GGATCCGCGG CCGCAAGCTT GCCACCATGG TAGGCATTTC CTATGGCAGG⁵⁰
AAGAAGCGGA GACAGCGACG AAGCACTCCT CCAAGCAGTG AGGATCATCA¹⁰⁰
AAATCCTATA TCAAGCAGC CCTTACCCCA AACCCGAGGG GACCCGACAG¹⁵⁰
GCTCGGAAGA ATCGAAGAAG AAGGTGGAGA GCAAGACAAA AACAGATCCA²⁰⁰
TTCGATTGTA AATACTGCAG CTATCATTGT CTAGTTTGCT TTCAGACAAA²⁵⁰
AGGCTTAGGC ATTTCCTATG GCAGGAAGAA GCGGATGGAG CCAATAGATC³⁰⁰
CTAACCTAGA GCCCTGGAAC CATCCAGGAA GTCAACCTAA CACTCCTTGT³⁵⁰
AATAAATGCT ATTGTAAATA CTGCAGCTAT CATTGTCTAG TTGTGGGATG⁴⁰⁰
GCCTGCTGTA AGAGAAAGAA TAAGAAGAAC TGAGCCAGCA GCAGAGGGAG⁴⁵⁰
TAGGACCAGC ATCTCAAGAC TTAGATAAAC ATGGAGCGCT TACAAGCAGC⁵⁰⁰
AACACAGCCC ACAATAATCC TGACTGTGCC TGGCTACAAG CACAAGAGGA⁵⁵⁰
GGAAGAAGAC GTAGGTTTTC CAGTCAGACC TCAGGTGCCT CTAAGACCAA⁶⁰⁰
TGACTTATAA GGCAGCATTC GATCTCAGCT TCTTTTTAAA AGAAAAGGGG⁶⁵⁰
GGACTGGAAG GGTTAATTCA CTCTAAGAGA AGACAAGACA TTCTTGATTT⁷⁰⁰
GTGGGTCTAT CACACACAAG CTACTTCCC TGATTGGCAA AACTACACGC⁷⁵⁰
CGGGACCAGG AGTCAGATAC CCACTGACCT TTGGATGGTG CTTCAAGCTA⁸⁰⁰
GTGCCAGTTG ATCCAAGGCA AGTAGAAGAG GCCAACAAAG GAGAAAACAA⁸⁵⁰
CTGTTTGCTA CACCCTATGA GCCAGCATGG AATGGAGGAT GCAGACAGAG⁹⁰⁰
AAGTATTAAG ATGGGTGTTT GACAGCAGTC TAGCACGCAG ACACCTGGCC⁹⁵⁰
CGCGAGAAAC ATCCGGAGTATTACAAAGACTAGGAATTCTCTAGAGCGGCCGC¹⁰⁰⁰
GTCGAC                                                                     ¹⁰⁰⁶

Bold = Restriction sites engineered

Underlined = Kozac sequence and start ATG

TG = junction between shuffled tat and nef

Figure 15

MVGISYGRKK RRQRRSTPPS SDHQNPISK QPLPQTRGDP TGSEESKKKV⁵⁰
ESKTKTDPFD CKYCSYHCLV CFQTKGLGIS YGRKKRMEPI DPNLEPWNHP¹⁰⁰
GSQPNTPCNK CYCKYCSYEC LVVGWPAVRE RIRRTEPAAE GVGPASQDLD¹⁵⁰
KHGALTSSNT AHNNPDCAWL QAQEEEDVG FPVRPQVPLR PMTYKAAFDL²⁰⁰
SFFLKEKGGL EGLIHSKRRQ DILDLWVYHT QGYFPDWQNY TPGPGVRYPL²⁵⁰
TFGWCFKLVP VDPREVEEAN KGENNCLLHP MSQHGMEDAD REVLRWVFDS³⁰⁰
SLARRHLARE KHPEYYKD                                           ³¹⁸

Figure 16

```
GGATCCGCGG  CCGCAAGCTT  GCCACCATGG  TGGGCATCAG  CTACGGCCGC⁵⁰
AAGAAGCGCC  GCCAGCGCCG  CAGCACCCCG  CCCAGCAGCG  AGGACCACCA¹⁰⁰
GAACCCCATC  AGCAAGCAGC  CCCTGCCCCA  GACCCGCGGC  GACCCCACCG¹⁵⁰
GCAGCGAGGA  GAGCAAGAAG  AAGGTGGAGA  GCAAGACCAA  GACCGACCCC²⁰⁰
TTCGACTGCA  AGTACTGCAG  CTACCACTGT  CTGGTGTGCT  TCCAGACCAA²⁵⁰
GGGCCTGGGC  ATCTCCTACG  GGCGCAAGAA  ACGGATGGAG  CCCATCGACC³⁰⁰
CCAACCTGGA  GCCCTGGAAC  CACCCCGGCA  GCCAGCCCAA  CACCCCCTGC³⁵⁰
AACAAGTGCT  ACTGCAAATA  CTGCTCCTAC  CACTGCCTCG  TGGTGGGCTG⁴⁰⁰
GCCCGCCGTG  CGCGAGCGCA  TCCGCCGCAC  CGAGCCCGCC  GCCGAGGGCG⁴⁵⁰
TGGGCCCCGC  CAGCCAGGAC  CTGGACAAGC  ACGGCGCCCT  GACCAGCAGC⁵⁰⁰
AACACCGCCC  ACAACAACCC  CGACTGCGCC  TGGCTGCAGG  CCCAGGAGGA⁵⁵⁰
GGAGGAGGAC  GTGGGCTTCC  CCGTGCGCCC  CCAGGTGCCC  CTGCGCCCCA⁶⁰⁰
TGACCTACAA  GGCCGCCTTC  GACCTGAGCT  TCTTCCTGAA  GGAGAAGGGC⁶⁵⁰
GGCCTGGAGG  GCCTGATCCA  CAGCAAGCGC  CGCCAGGACA  TCCTGGACCT⁷⁰⁰
GTGGGTGTAC  CACACCCAGG  GCTACTTCCC  CGACTGGCAG  AACTACACCC⁷⁵⁰
CCGGCCCCGG  CGTGCGCTAC  CCCCTGACCT  TCGGCTGGTG  CTTCAAGCTG⁸⁰⁰
GTGCCCGTGG  ACCCCGCGA  GGTGGAGGAG  GCCAACAAGG  GCGAGAACAA⁸⁵⁰
CTGCCTGCTG  CACCCCATGA  GCCAGCACGG  CATGGAGGAC  GCCGACCGCG⁹⁰⁰
AGGTGCTGCG  CTGGGTGTTC  GACAGCAGCC  TGGCCGCCG   CCACCTGGCC⁹⁵⁰
CGCGAGAAGC  ACCCCGAGTA  CTACAAGGAC  TGAGAATTCT  CTAGAGCGGC¹⁰⁰⁰
CGCGTCGAC                                                  ¹⁰⁰⁶
```

Bold= Restriction sites engineered

Underlined= Kozac sequence and start ATG

GG= Junction between shuffled, codon optimised *tat* and *nef*

Figure 17

```
                                                                40
ZATatcon    MEPVDPNLEPWNHPGSQPKTACNKCYCKHCSYHCLVCFQT    SEQ ID NO: 39
RB13        MEPVDPKLEPWNHPGSQPKTACTQCYCKKCSYHCLVCFQT    SEQ ID NO: 40
Du151       MEPIDPNLEPWNHPGSQPNTPCTKCYCKYCSYHCLVCFQT    SEQ ID NO: 41
Du368       MEPVDPNLEPWNHPGSQPKTPCTNCYCKHSSYHCLVCFQT    SEQ ID NO: 42
Du123       MEPVDPNLDPWNHPGSQPKTPCTKCYCKHCSYHCLVCFQT    SEQ ID NO: 43
Du204       MEPVDLDLEPWNNPGSQPKTACNKCYCKHCSYHCLVCFQT    SEQ ID NO: 44
CTSc2       MEPVDPNLEPWNHPGSQPKTACNPCYCKKCSYHCLVCFQK    SEQ ID NO: 45
RB28        MEPVDPNLEPWNHPGSQPKTACNKCYCKVCSYHCLVCFQT    SEQ ID NO: 46
GG2         ------NLEPWNHPGSQPKTACNPCYCKHCSYHCLVCFQT    SEQ ID NO: 47
GG10        ------NLEPWNHPGSQPKTPCNKCYCKHCSYHCLVCFQT    SEQ ID NO: 48
Du422       MEPIDPNLEPWNHPGSQPNTPCNNCYCKHCSYHCLVCFQT    SEQ ID NO: 49
Du281       MEPVDPNLEPWNHPGSQPLTPCNKCYCKHCSYHCLVCFQT    SEQ ID NO: 50
Du179       MEPIDPNLEPWNHPGSQPKTACNKCFCKRCSYHCQFCFLT    SEQ ID NO: 51
RB12        MEPIDPNLEPWNHPGSQPKTPCNKCYCKRCSYHCLACFQT    SEQ ID NO: 52
GG4         MEPTDPNLEPWNHPGSQPKTPCNKCYCKRCSYHCLVCFQK    SEQ ID NO: 53
Du156       MEPVDPNLEPWNHPGSQPKTPCNTCYCKHCSYHCLVCFQT    SEQ ID NO: 54
Du285       MEPVDPKLEPWNHPGSQPKTPCNSCYCKKCSYHCLVCFQK    SEQ ID NO: 55
CTSc1       MDPIDPNLEPWNHPGSQPKTACNKCYCKRCCYHCLVCFQK    SEQ ID NO: 56

80
ZATatcon    KGLGISYGRKKRRQ-RRSAPPSSEDHQNLISKQPLPQTRG
RB13        KGLGISYGRKKRRQ-RRAPPSSEDHQNPISKQPLPRTRG
Du151       KGLGISYGRKKRRQ-RRSTPPSSEDHQNLISEQPLPQARG
Du368       KGLGISYGRKKRRQ-RRSTPPSSEDHQNLISKQPLSQPEG
Du123       KGLGISYGRKKRRQ-RRSTPPSSEDHQNLISKQPLPQPRG
Du204       KGLGISYGRKKRRQQRRSTPSSSKDHQNPISKQPLPQPRG
CTSc2       KGLGISYGRKKRRQ-RRTAPPSSEDHQNPISKQPFPRTQG
RB28        KGLGISYGRKKRRQ-RRSAPPSSEDHQNPISKQPLPQTRR
GG2         KGLGISYGRKKRRQ-RQTAPPSSEDHQNPISKQPLPQTRG
GG10        KGLGISYGRKKRRQ-RQTTPPSSEDHQNLVSKQPLSQTRG
Du422       KGLGISYGRKKRRQ-RRSTPPSSEDHQNPISKQPLSQTRG
Du281       KGLGISYGRKKRRQ-RRSTPPSSEDHQNLVSKQPLPQTRG
Du179       KGLGISYGRKKRRQ-RRSAPPSSEDHQNPISKQPLPQTRG
RB12        KGLGISYGRKKRRQ-RRSTPPSSKNHQNPVSKQPLPQTRG
GG4         KGLGISYGRKKRRQ-RRNAPPSSEDHQNLISKQPLPQTRG
Du156       KGLGISYGRKKRRQ-RRSTPPSNKDHQNPVPKQPLPQPRG
Du285       KGLGIYYGRKKQRQ-RRRAPPSNKDHQNPVPKQ-------
CTSc1       KGLGISYGRKKRRQ-RRSAPPSNKDHQNPVSKQ-------

101
ZATatcon    DPTGSEESKKKVESKTETDPFD
RB13        DSTGSEESKKKVESKTETDQFD
Du151       VPTGSEESKKKVESKTKTDPFD
Du368       NSTGSEKSKKKVESKTRTDPFD
Du123       DSTGSEESKKKVESKTKTDQFD
Du204       DSTGSEESKKKVESKTQTDPFA
CTSc2       DPTGSEESKKKVESKTKTDQFD
RB28        DPTGSEESKKKVESKAEADPFD
GG2         DPTGSEESKKKVESKTKTDPFD
GG10        DPTGSEESKKKVESKTETDPFDW
Du422       DPTGSEESKKKVESKTKTDPFD
Du281       DPTGSEESKKKVESKTKTDPFD
Du179       DPTGSEKSKKKVESKTETDPFD
RB12        DPTGSEESKKKVESKTETDPFD
GG4         DPTGSEESKKKVESKTETDPFD
Du156       DSTGSEESKKKVESKTKTDPFD
Du285       ----------------------
CTSc1       ----------------------
```

Figure 22

|          |                                                                                          | SEQ ID NO: |
|----------|------------------------------------------------------------------------------------------|------------|
| ZANefcon | MGGKWSKSSIVGWPAVRERIRR----------TEPAAEG--------VGAASQDLDKHG                              | 57         |
| rb28     | MGGKWSKSSIGGWPAIRERIRR----------AKPAAEG--------VGAASQDLEKHG                              | 58         |
| gg5      | MGGKWSKSSIVGWPAVRERMRK----------TEPAAEG--------VGAASQDLDKHG                              | 59         |
| Du151    | MGGKWSKSSIVGWPAVRERIRRT---------EPAAEG--------VGAASQDLDKHG                               | 60         |
| rb12     | MGGKWSKSSIVGWPAVRERIRQTR--------IEPAAEG--------VGAASQDLDKYG                              | 61         |
| Du422    | MGGKWSKSSLAGWPAVRERIRRT---------EPAAEG--------VGAASRDLEKHG                               | 62         |
| Du123    | MGGKWSKSSIIGWPEVRERIRRT---------EPAAEG--------VGAASRDLEKYG                               | 63         |
| Du368    | MGGKWSKSSIIGWPTEGERRRRAKPT----IRRTEPAAEG--------VGAASQDLEKYG                             | 64         |
| Du467    | MGGKWSKSSIVGWPTERERRRRAKPT----KRRPEPAAEG--------VGAASQDLDKYG                             | 65         |
| Du457    | MGGKWSKSSIIGWPEEER----------IRRTEPAAEG--------VGAASRDLDKYG                               | 66         |
| Du258    | MGGKWSKSSIIGWPEVREGIRRT---------EPAAEG--------VGAASQDLDKYG                               | 67         |
| Du179    | MGGKWSKSSIVGWPTVRERMRRT---------DPAAEG--------VGAASQDLDKHG                               | 68         |
| SW-10    | MGGKCSKSSIVGWPEIRERIRQTR--------TGPAAEG--------VGAASQDLDKYG                              | 69         |
| gg3      | MGGKWSKSSIVGWPAVRERIRRA---------EPAAEG--------VGAASRDLDKHG                               | 70         |
| rb18     | MGNKWSKSSIVGWPAVRERIRRT---------EPAAEG--------VGAASQDLDKHG                               | 71         |
| SW-7     | MGGKWSKSSIVGWPAVRERIRRTRPNGRERIRQTEPAAEG--------VGAASQDLDKYG                             | 72         |
| CTSc2    | MGGKLSKSSIVGWPEVRERLRRAGS----------AAEG--------VGAASQDLDRHG                              | 73         |
| gg2      | MGGKWSKSSIVGWPEVRERLRRTEP----------AAEG--------VGTASQDLDKYG                              | 74         |
| COT2     | MGGKWSKGSIVGWPAVRERIRRTVPT----AKRTEPAAEG--------VGPASRDLDKYG                             | 75         |
| COT6     | MGGKWSKGSIVGWPAVRERIRRTVPT----AKRTEPAAEG--------VGPASRDLDKYG                             | 76         |
| SW-15    | MGGKWSKSSIVGWPAVRERIRRAGP-----GRRAEPAAEG--------VGAASRDLDKYG                             | 77         |
| SW-5     | MGGKWSKSSIVGWPAVRERIRRAGP-----GRRAEPAAEG--------VGAASRDLDKYG                             | 78         |
| gg6      | MGSKWSKSSIVGWPAVRERIRQTS-----------AAEG--------VGAASQDLDKHG                              | 79         |
| SW-20    | MGGQWSKSSIIGWPAVRERIRKTTPT----AERVEAAAVG--------VGAASQDLEKHG                             | 80         |
| rb15     | MGGKWSKSSIVGWPAVRERMRR--------ARTEPAAEG--------VGAASRDLEKHG                              | 81         |
| gg10     | MGGKWSKRSVVGWTEIRDRMRRTRP--------TAPAAEG--------VGAASQDLDRHG                             | 82         |
| gg4      | MGNKWSKS----WPSVRERIRRARPA---AEERTRPAAEG--------VGTASQDLDKHG                             | 83         |
| rb13     | MGNKWSKSSIVGWPAVRDRIRRTEP-------RTEPAAVG--------VGAASQDLDKHG                             | 84         |
| rb21     | MGNKWSKS----WPAVRDRMRRTRP----------AAEG--------VGAASQDLDKHG                              | 85         |
| SW9      | MGGKWSKRSLGGWPAVRERMRRTEPAAE-RIRQTEPAAEG--------VGAASQDLDRHG                             | 86         |
| SW2      | MGGKWSKRSLGGWPAVRERMRRTEPAAE-RIRQTEPAAEG--------VGAASQDLDRHG                             | 87         |
| SW8      | MGGKWSKRSLGGWPAVRERMRRTEP---------EPAAEG--------VGAASQDLDRHG                             | 88         |
| SW-23    | MGGKWSKCSMGGWPSVRERMRRTEP----------AAEG--------VGAASQDLDRHG                              | 89         |

|          |                                                                              120            |
|----------|----------------------------------------------------------------------------------------------|
| ZANefcon | ALTSSNTAHNNADCAWLQAQEEEEEVGFPVRPQVPLRPMTYKGAFDLSFFLKEKGGLEGL                                  |
| rb28     | ALTTSNTARNNPDCAWLQAQEEEEEVGFPVRPQVPLRPMTYKGAFDLSFFLKEKGGLEGL                                  |
| gg5      | ALTSSNTATTNAACAWLEAQEEEGEVGFPVRPQVPLRPMTYKGAFDLGFFLKEKGGLEGL                                  |
| Du151    | ALTSSNTAHNNPDCAWLQAQEEEPEVGFPVRPQVPLRPMTYKAAFDLSFFLKEKGGLEGL                                  |
| rb12     | ALTSSNTAHNNADCAWLQAQEEEGEVGFPVRPQVPLRPMTYKGAFDLSFFLKEKGGLEGL                                  |
| Du422    | ALTSSNTAHNNPDCAWLQAQEEEEEVGFPVRPQVPLRPMTYKAAVDLSFFLKEKGGLEGL                                  |
| Du123    | ALTSSNTAHTNADCAWLQAQEEEDEVGFPVRPQVPLRPMTYKAAFDLSFFLKEKGGLEGL                                  |
| Du368    | ALTSSNTAHTNADCAWLQAQEEEDEVGFPVRPQVPLRPMTYKAAFDLSFFLKEKGGLEGL                                  |
| Du467    | ALTTSNTAHNNPDCAWLQAQEEEEEVGFPVTPQVPVRPMTYKAAFDLSFFLKEKGGLDGL                                  |
| Du457    | ALTTSNTAHNNPDCAWLQAQEEEEEVGFPVRPQVPLRPMTYKAAFDLSFFLKEKGGLEGL                                  |
| Du258    | ALTTSNTAHTNADCAWLQAQEEEEEVGFPVRPQVPLRPMTYKAAFDLSFFLKEKGGLDGL                                  |
| Du179    | ALTSSNTAHNNPACAWLQAQEEDEEVGFPVRPQVPLRPMTFKGAFDLSFFLKEKGGLDGL                                  |
| SW-10    | ALTTSNTPHNNAACAWLQAQEEEEEVGFPVRPQVPLRPMTYKGAFDLGFFLKEKGGLDGL                                  |
| gg3      | ALTTSNTAQNNADCAWLQAQEEADEVGFPVRPQVPLRPMTYKAAFDLGFFLKEKGGLDGL                                  |
| rb18     | ALTTSNTPTNNADCAWLQAQEDED-VGFPVRPQVPLRPMTYKAAVDLSFFLKEKGGLEGL                                  |
| SW-7     | ALTSSNTPGNNADCAWLQAQEEEEDVGFPVRPQVPLRPMTYKAAVDLSFFLKEKGGLEGL                                  |
| CTSc2    | ALTSSNTPATNAACAQLEAQEEEEEVGFPVRPQVPLRPMTFKGAFDLSFFLKEKGGLDGL                                  |
| gg2      | ALTINNSGPTNAACAWLEAQEEDGEVGFPVRPQVPLRPMTFKGAFDLSFFLKEKGGLDGL                                  |
| COT2     | ALTSSNTTSNNAACAWLEAQEEEGEVGFPVKPQVPVRPMTYKAALDLGFFLKEKGGLDGL                                  |

```
COT6       ALTSSNTTSNNAACAWLEAQEEEGEVGFPVKPQVPVRPMTYKAALDLGFFLKEKGGLDGL
SW-15      ALTTSNTASNNADCAWLEAQEDE-EVGFPVKPQVPLRPMTYKGAFDLGFFLKEKGGLDGL
SW-5       ALTTSNTASNNADCAWLEAQEDE-EVGFPVKPQVPLRPMTYKGAFDLGFFLKEKG-TGWV
gg6        ALTTSNTASNNAACAWLEAQEEEGEVGFPVRPQVPLRPMTYKGAFDLSFFLKEKGGLDGL
SW-20      ALTSSNTAASNADCAWLEAQEEEEEVGFPVRPQVPLRPMTYKAAFDLGFFLKEKGGLDGI
rb15       ALTSSNTAATNAACAWLEAQEEEEEVGFPVRPQVPLRPMTYKGAVDLGFFLKEKGGLDGL
gg4        ALTTSNTATNNAACAWVEAQEEGEEVGFPVRPQVPLRPMTYKAAFDLSFFLKEKGGLEGL
rb13       ALTSSNTDANNATCAWLRAQEEGEEEVGFPVRPQVPLRPMTYKAAFDLSFFLKEKGGLEGL
rb21       ALTTSNTVSNNAAGAWLQAQEEEEEVGFPVRPQVPLRPMTYKAAFDLSFFLKEKGGLDGL
SW9        ALTSSNTETTNATCAWLRAQEEDEEVGFPVKPQVPLRPMTYKAAFDLGFFLKEKGGLEGL
SW2        ALTSSNTETTNATCAWLRAQEEDEEVGFPVKPQVPLRPMTYKAAFDLGFFLKEKGGLDGL
SW8        ALTSSNTATNNATCAWLRAQEEEEEVGFQVKPQVPLRPMTYKAAFDLGFFLKEKGGLDGL
SW-23      ALTTSNTPTNNADCAWLQAQEEGEEVGFPVRPQVPLRPMTYKAAFDLSFFLKEKGGLEGL

180
ZANefcon   IYSK-----------KRQEILDLWVYHTQGFFPDWQNYTPGPGVRYPLTFGWCFKLVPV
rb28       IHSK-----------KRQDILDLWVYHTQGYFPDWQNYTPGPGVRYPLTFGWCFKLVPV
gg5        IYSK-----------KRQEILDLWVYHTQGFFPDWQNYTLGPGVRYPLTFGWPFKLVPV
Du151      IYSK-----------KRQDILDLWVYHTQGYFPDWQNYTPGPGVRLPLTFGWCFKLVPV
rb12       IWSK-----------KRQEILDLWVYHTQGYFPDWQNYTPGPGVRFPLTFGWCFKLVPV
Du422      IHSK-----------RRQDILDLWVYHTQGYFPDWQNYTPGPGVRFPLTFGWCFKLVPV
Du123      IWSK-----------RRQDILDLWVYNTQGYFPDWQNYTPGPGVRFPLTFGWCFKLVPV
Du368      IYSK-----------KRQDILDLWVYHTQGFFPDWQNYTPGPGVRYPLTFGWCFKLVPV
Du467      IHSK-----------KRQEILDLWVYHTQGFFPDWQNYTPGPGVRYPLTFGWCFKLVPV
Du457      IYSK-----------KRQDILDLWVYNTQGFFPDWQNYTPGPGVRYPLTFGWCFKLVPV
Du258      IYSK-----------KRQDILDLWVYHTQGFFPDWQNYTPGPGTRFPLTFGWCFKLVPV
Du179      IYSK-----------KRHDILDLWVYNTQGYFPDWQNYTPGPGIRYPLTFGWCFKLVPV
SW-10      IWSKEKGGLDGLIWSKKRQEILDLWVYNTQGYFPDWQNYTPGPGVRYPLTFGWCFKLVPV
gg3        IWSK-----------KRQEILDLWVYHTQGFFPDWQNYTPGPGVRYPLTFGWCFKLVPV
rb18       IYSK-----------KRQEILDLWVYHTQGFFPDWQNYTPGPGVRFPLTFGWCFKLVPV
SW-7       IHSK-----------QRQDILDLWVYNTQGYFPDWQNYTPGPGIRYPLTFGWCFKLVPV
CTSc2      IYSK-----------KRHEILDLWVYNTQGYFPDWQNYTPGPGVRYPLTFGWCYKLVPV
gg2        IYSK-----------KRQEILDLWVYHTQGFFPDWQNYTPGPGVRYPLTFGWCYKLVPV
COT2       IYSK-----------KRQDILDLWVYHTQGFFPDWQNYTPGPGVRYPLTFGWCFKLVPV
COT6       IYST-----------KRQEILDLWVYHTQGFFPDWQNYTSGPGVRYPLTFGWCFKLVPV
SW-15      IYSK-----------KRQEILDLWVYNTQGYFPDWQNYTSGPGIRYPLTFGWCYKLVPV
SW-5       NLLK-----------KRQDILDLWVYNTQGFFPDWQNYTPGPGVRYPLTFGWCYKLVPV
gg6        IYSK-----------KRQEILDLWVYHTQGFFPDWQNYTPGPGVRYPLTFGWCYKLVPV
SW-20      IYSK-----------KRQDILDLWVYHTQGFFPDWQNYTPGPGVRYPLTFGWPFKLVPV
rb15       IYSK-----------QRQDILDLWVYNTQGFFPDWQNYTPGPGVRYPLTFGWCYKLVPV
gg10       IYSK-----------KRQEILDLWVYHTQGFFPDWQNYTPGPGVRYPLTFGWCFKLVPV
gg4        IYSK-----------KRQDILDLWVYNTQGFFPDWQNYTPGPGIRYPLTFGWCFKLVPV
rb13       IYSK-----------RRQDILDLWVYNTQGFFPDWHNYTPGPGTRYPLTFGWCFKLVPV
rb21       IYSK-----------QRQDILDLWVYNTQGYFPDWQNYTPGPGVRYPLTFGWCYKLVPV
SW9        IYSK-----------KRQEILDLWVYNTQGFFPDWHNYTPGPGVRYPLTFGWCFKLVPV
SW2        IYSK-----------KRQEILDLWVYHTQGFFPDWQNYTPGPGVRYPLTFGWCFKLVPV
SW8        ISSK-----------KRQEILDLWVYNTQGYFPDWQNYTPGPGVRYPLTFGWCIQLVAV
SW-23      IHSK-----------KRQDILDLWVYQTQGFFPDWQNYTPGPGVRYPLTFGWCFKLVPV 239
ZANefcon   DPREVEEANEGENNCLLHPMSQHGMEDEDREVLKWKFDSSLARRHMARELHPEYY-KDC
rb28       DPREVEEANEGEDNCLLHPMSQHGMEDAEREVLMWKFDSSLARRHMARELHPEYY-KDC
gg5        DPGEVEEANKGENNCLLHPISLHGMEDDHREVLKWKFDSQLARRHIARELHPEYY-KDC
Du151      DPEEVEEANKGENNCLLHPLSQHGMEDADREVLKWVFDSSLARRHLAREKHPEYY-KDC
rb12       DPSEVEEANKGENNCLLHPMSQHGMEDEDREVLKWVFDSSLARRHTAREKHPEFY-KDC
Du422      DPREVEEANKGENNCLLHPMSQHGIEDEEREVLQWMFDSSLARRHMAREKHPEFY-KDC
Du123      DPREVEEANKGENNCLLHPMSQHGIEDEDREVLKWEFDSSLARRHLAREIHPEYY-KDC
Du368      DPREVEEATKGEENCLLHPLNQHGMEDEEKEVLQWKFDSSLARRHLARELHPEYY-KDC
```

```
Du467    DPREVEEANQGENNCVLHPLSQHGMEDEEKEVLKWMFDSSLARRHLAREKHPEYY-KDC
Du457    DPREVEEANKGENNCLLHPMSQHGMEDPEGEVLKWKFDSSLARRHLAREKHPEFY-KDC
Du258    DPQEVEEANEGENNCLLHPISQHGMEDADREVLRWEFDSQLARRHMARELHPEFY-KDC
Du179    DPREVEEANEGDNNCLLHPMSQHGIEDGEREVLKWEFDSSLARRHMAREKHPEFY-KDC
SW-10    DPSEVEEANKGENNCLLHPMSQHGMEDEEREVLKWQFDSSLARRHMAREIHSEYY-KDC
gg3      DPREVEEYNKGENNCLLHPMSLHGMEDEEGEVLKWEFDSSLARRHLAREKHPEFY-KDC
rb18     DPREVEEANEGENNCLLHPMSLHGMEDEEREVLKWVFDSSLARRHLARELHPEYY-KDC
SW-7     DPREVEEANEGEDNCLLHPMSQHGADDADKEVLMWKFGSDLAYKHIAREIHSEYY-KDC
CTSc2    DPRKVEEANEGENNCLLHPMHQHGMDDEDREVLIWKFDSSLARRHMAREMHPEYY-KDC
gg2      DPGEVEEANKGENNCLLHPLSQHGMEDEDREVLKWQFDSSLARRHLARELHPEYY-KDC
COT2     DPEKVEEANEGENNNLLHPGSLHGMDDPQREVLQWRFDSRLAFHHVARELHPGSG-DDC
COT6     DPQEVEEANEGDNNCLLHPMSLHGMEDPHGEVLKWQFDSSLARRHLARELHPEYY-KDC
SW-15    DPSEVEEANKGEDNCLLHPMSQHGMEDEDREVLKWQFDSSLARRHVARELHPGVL-KDC
SW-5     DPKEVEEANKGENNCLLHPMSQHGMEDEERETLKWVFDSSLARRHIAREKHPEYY-KDC
gg6      DPKEVEEANEGENNCLLHPMSLHGMEDEDREVLKWQFDSLLARRHVARELHPEFY-KDC
SW-20    DPREVEEANNGENNCLLHPMSQHGMDDADREVLMWKFDSGLARRHMARE-YSEFY-KDC
rb15     DPREVEEANK-EDTRLLHPISQHGMEDADREVLKWQFDSSLARRHVARELYPEFY-KDC
gg10     DPKEVEEANEGEDNCLLHPMSLHGMEDSDGEVLKWFDTQLARRHIARELHPEFY-KDC
gg4      DPDEVEEANKGENNCLLHPMSQHGMEDEDREVLQWKFDSALARRHMARELHPEFF-NN-
rb13     DPREVEEATEGDNNCLLHPMSQHGMEDEHKEVLQWKFDSLLARRHMARELHPEFY-KDC
rb21     DPREVEEANEGEDNCLLHPISQHGMEDPQRETLKWVFDSHLARRHMARELHPEYY-KDC
SW9      DPEEVEEATEGENNCLLHPINQHGMDDEDREVLKWKFDSMLARRHMARELHPEYY-KDC
SW2      DPAEVEENNKGEDSCLLHPISQHGMDDDDKEVLQWQFDSSLARIHLARELHPEYY-KDC
SW8      FQAYVEEVNEGENNCLLHPISQHGMEDEEREVLKWQFDSSLARRHVARELHPEYY-KDC
SW-23    DPGEVEEANKGEDNCLLHPMSQHGMEDGDREVLKWVFDSSLARRHLGPELHPEYY-KDC
```

|          |                                                      | 40 |                 |
|----------|------------------------------------------------------|----|-----------------|
| ZARevcon | MAGRSGDS-DEALLQAVRIIKILYQSNPYPKPEGTRQARK             |    | SEQ ID NO: 90   |
| RB18     | MAGRSGDS-DKPLLQAVRIIKILYQSNPYPKPEGTRQARR             |    | SEQ ID NO: 91   |
| GG5      | MAGRSGDS-DEALLQAVRIIKILYQSNPYPKPEGTRQARR             |    | SEQ ID NO: 92   |
| GG10     | MAGRSGDS-DKPLLQAVRTIKILYQSNPYPKPEGTRQARR             |    | SEQ ID NO: 93   |
| Du179    | MAGRSGDS-DEALLQAVRIIKILYQSNPYPKPEGTRQARR             |    | SEQ ID NO: 94   |
| Du156    | MAGRSGDS-DEALLQVIRIIKILYQSSPYPNPEGTRQARK             |    | SEQ ID NO: 95   |
| Du151    | MAGRSGDS-DEALLQAVRIIKILYQSNPYPKPEGSRQARK             |    | SEQ ID NO: 96   |
| Du422    | MAGRSGDS-DEALLQAVKIIKILYQSNPYPKPEGTRQARK             |    | SEQ ID NO: 97   |
| DU281    | MAGRSGDS-DEALLQAVRTIKILYQSSPYPKPEGTRQARK             |    | SEQ ID NO: 98   |
| RB28     | MAGRSGDS-DEALLQAVRIIKILYQSNPYPKPGGTRQARK             |    | SEQ ID NO: 99   |
| CTSc2    | MAGRSGDN-DEQLLQAVRIIKILYQSNPFPEPKGTRQARK             |    | SEQ ID NO: 100  |
| RB13     | MAGRSGDS-DAELLQAVRIIKILYQSNPYPEPEGTRQARK             |    | SEQ ID NO: 101  |
| DU204    | MAGRSGDSSDAALLQAVRIIKILYQSSPEPR--GTRQARK             |    | SEQ ID NO: 102  |
| Du368    | MAGRSGDS-DEALLQAVRTIKILYQSSPYPKPEGTRQARK             |    | SEQ ID NO: 103  |
| Du123    | MAGRSGDS-DEALLQAVRIIKILYQSSPYPKPEGTRQARK             |    | SEQ ID NO: 104  |
| RB27     | MAGRSGDS-DEALLQAVRIVKILYQSNPYPKPEGTRQARK             |    | SEQ ID NO: 105  |
| RB21     | MAGRSGDS-DEALLQAVRIIKILYQSNPYPKPEGTRQARK             |    | SEQ ID NO: 106  |
| RB12     | MAGRSGDS-DEALLQAVRIIKILYQSNPYPKPEGTRQAQK             |    | SEQ ID NO: 107  |

|          |                                           | 80 |
|----------|-------------------------------------------|----|
| ZARevcon | NRRRRWRARQRQIHSISERILSTCLGRPAEPVPLQLPPIE  |    |
| RB18     | NRRRRWRARQRQINSISERILSTCLGRPTEPVPFQLPPIE  |    |
| GG5      | NRRRRWRARQRQIHSISERILSTCLGRPAEPVPLQLPPIE  |    |
| GG10     | NRRRRWRARQRQIHSIGERILSHCLGRPAEPVPLQLPPIE  |    |
| Du179    | NRRRRWRARQRQIRSISERILTTCLGRSAEPVPLQLPPIE  |    |
| Du156    | NQRRRWRARQRQIHSISERILSTCLGRSAEPVPLQLPPIE  |    |
| Du151    | NRRRRWRARQKQIHSISERILSTCLGRSAEPVPLRLPPIE  |    |
| Du422    | NRRRRWRARQRQIHSISERILSTCLGRSAEPVPLQLPPIE  |    |
| DU281    | NRRRRWRARQRQIHSISERILNACLGRPAEPVPLQLPPLE  |    |
| RB28     | NRRRRWRARQRQIHSISQRILSDCLGRPAEPVPLQLPPIE  |    |
| CTSc2    | NRRRRWRARQRQINSISERILSDCLGRSAEPVPLQLPPIE  |    |
| RB13     | NRRRRWRARQRQINSISERILSTCLGRSAEPVPLQLPPIE  |    |
| DU204    | NRRRRWRARQKQIHSLRERILSNCLGRPAEPVPLQLPPIE  |    |
| Du368    | NRRRRWRARQRQIHSISERILSTCLGRPAEPVPLQLPPIE  |    |
| Du123    | NRRRRWRARQRQINSISERILSTCLGRPTEPVPLQLPPIE  |    |
| RB27     | NRRRRWRARQRQIHSISERILVTCLGRPTEPVPLQLPPIE  |    |
| RB21     | NRRRRWRARQRQIHSISERILSTVLGRPTEPVPLQLPPIE  |    |
| RB12     | NRRRRWRARQRQIHSISERILSTCLGRPAEPVPLQLPPIE  |    |

|          |                                      | 107 |
|----------|--------------------------------------|-----|
| ZARevcon | RLHIDCSESSGTSGTQQSQQTTEGVGSP         |     |
| RB18     | RLCIDCSESGGTS-------TAEGVGST         |     |
| GG5      | RLNLGCDESSGTSGTQQPQGTTEGVGSP         |     |
| GG10     | RLHIDCSESSGTSGTQQSQGTTEGVGSP         |     |
| Du179    | RLHIDCSEDSGTSGTQQSQGTPEGVGSP         |     |
| Du156    | RLHIDCSESSGTSGTQQSQGTTEGVGSS         |     |
| Du151    | RLHIDCSESSGTSGTQQSQGTAERVGSP         |     |
| Du422    | RLHIDCSESSGTSGTQQSQGTAERVGSP         |     |
| DU281    | RLHIDCSENSGTSGTQQPQGTTERVGSP         |     |
| RB28     | KLHIDCSEDSGTSGTQQSQGTTERVGSP         |     |
| CTSc2    | RLHIGCSESGGTSGAQQSHGTTEGVGRP         |     |
| RB13     | RLHIGDSESGGTSGTQQPQGTTERVGNH         |     |
| DU204    | RLHIDCSENGGTSGTQQPQGTTEGVGSP         |     |
| Du368    | RLHIGDSESSGTSGTQQPQGTAEGLGSP         |     |
| Du123    | RLHIGCSESSGTSGTQQSQGTTERVGSP         |     |
| RB27     | RLHINCSESSGTSGTQQSQGTTEGVGNP         |     |
| RB21     | RLHINCSESSGTSGTQQSQGTTEGVGNP         |     |
| RB12     | RLcIDCSESSGTSGTQQSQgTTEGVGSc         |     |

Figure 24

| | ZAtatcon | RB13 | Du151 | Du368 | Du123 | Du204 | CTSc2 | RB28 | GG2 | GG10 | Du422 | Du281 | Du179 | RB12 | GG4 | Du156 | Du285 | CTSc1 |
|---|---|---|---|---|---|---|---|---|---|---|---|---|---|---|---|---|---|---|
| ZAtatcon | 100 | 90.492 | 89.356 | 87.031 | 91.612 | 88.202 | 89.356 | 94.871 | 94.535 | 93.391 | 91.612 | 94.871 | 91.612 | 90.492 | 94.871 | 88.202 | 79.288 | 86.289 |
| RB13 | 90.492 | 100 | 82.155 | 82.155 | 88.202 | 83.403 | 90.492 | 88.202 | 88.629 | 83.547 | 84.632 | 84.632 | 84.632 | 83.403 | 87.031 | 83.403 | 84.598 | 81.099 |
| Du151 | 89.356 | 82.155 | 100 | 85.841 | 90.492 | 80.886 | 80.886 | 84.632 | 86.13 | 87.39 | 91.612 | 91.612 | 83.403 | 87.031 | 88.202 | 84.632 | 71.596 | 79.288 |
| Du368 | 87.031 | 82.155 | 85.841 | 100 | 90.492 | 78.284 | 84.632 | 80.886 | 82.221 | 86.13 | 88.629 | 88.202 | 87.031 | 79.596 | 83.403 | 85.841 | 75.536 | 77.435 |
| Du123 | 91.012 | 88.202 | 90.492 | 90.492 | 100 | 87.031 | 84.632 | 85.841 | 82.221 | 83.547 | 88.202 | 88.629 | 87.031 | 92.155 | 88.202 | 90.492 | 75.536 | 79.288 |
| Du204 | 88.202 | 83.403 | 80.886 | 82.155 | 87.031 | 100 | 79.596 | 84.632 | 87.39 | 88.629 | 84.632 | 86.13 | 89.356 | 80.886 | 88.202 | 82.155 | 75.536 | 81.099 |
| CTSc2 | 89.356 | 90.492 | 84.632 | 78.284 | 84.632 | 79.596 | 100 | 87.031 | 86.13 | 83.547 | 84.632 | 86.13 | 83.403 | 82.155 | 82.155 | 84.632 | 84.598 | 86.289 |
| RB28 | 94.871 | 88.202 | 80.886 | 80.886 | 85.841 | 84.632 | 87.031 | 100 | 87.39 | 83.547 | 85.841 | 85.841 | 85.841 | 88.202 | 88.202 | 88.202 | 81.099 | 87.944 |
| GG2 | 94.535 | 88.629 | 86.13 | 82.221 | 86.13 | 87.39 | 92.229 | 87.39 | 100 | 87.39 | 88.202 | 88.629 | 89.356 | 87.39 | 91.048 | 84.632 | 77.093 | 83.027 |
| GG10 | 93.391 | 83.547 | 87.39 | 86.13 | 88.629 | 88.629 | 83.547 | 88.202 | 92.229 | 100 | 92.229 | 92.229 | 91.048 | 91.048 | 92.229 | 87.39 | 77.093 | 83.027 |
| Du422 | 91.612 | 84.632 | 91.612 | 88.202 | 89.356 | 89.356 | 85.841 | 89.356 | 92.229 | 92.229 | 100 | 94.535 | 84.849 | 90.492 | 89.356 | 89.356 | 77.435 | 82.868 |
| Du281 | 94.871 | 84.632 | 91.612 | 88.202 | 89.356 | 89.356 | 85.841 | 89.356 | 94.535 | 92.229 | 100 | 100 | 87.031 | 91.048 | 91.612 | 80.886 | 79.288 | 82.868 |
| Du179 | 91.612 | 84.632 | 83.403 | 87.031 | 92.714 | 82.155 | 85.841 | 88.202 | 84.849 | 94.535 | 93.801 | 100 | 85.841 | 91.612 | 80.356 | 91.612 | 71.596 | 84.598 |
| RB12 | 90.492 | 83.403 | 87.031 | 88.202 | 82.155 | 85.841 | 85.841 | 84.632 | 91.048 | 84.849 | 93.801 | 100 | 85.841 | 100 | 89.356 | 91.612 | 80.886 | 84.598 |
| GG4 | 94.871 | 87.031 | 88.202 | 90.492 | 88.202 | 88.202 | 82.155 | 88.202 | 91.048 | 91.048 | 94.849 | 91.612 | 89.356 | 89.356 | 100 | 90.492 | 79.288 | 87.944 |
| Du156 | 88.202 | 83.403 | 84.632 | 85.841 | 90.492 | 82.155 | 88.202 | 82.155 | 92.229 | 87.39 | 89.356 | 91.612 | 80.886 | 89.356 | 84.632 | 100 | 87.944 | 86.289 |
| Du285 | 79.288 | 84.598 | 71.596 | 75.536 | 75.536 | 88.202 | 84.598 | 81.099 | 77.093 | 77.093 | 77.435 | 79.288 | 71.596 | 79.288 | 81.099 | 87.944 | 100 | 82.868 |
| CTSc1 | 86.289 | 81.099 | 79.288 | 77.435 | 81.099 | 86.289 | 86.289 | 87.944 | 83.027 | 83.027 | 82.868 | 82.868 | 84.598 | 87.944 | 86.289 | 86.289 | 82.868 | 100 |

| | ZArevcon | RB18 | GG5 | GG10 | Du179 | Du156 | Du151 | Du422 | Du201 | RB2R | CTSc2 | RB13 | Du204 | Du368 | Du123 | RB27 | RB21 | RB12 |
|---|---|---|---|---|---|---|---|---|---|---|---|---|---|---|---|---|---|---|
| ZArevcon | 100 | 85.685 | 93.143 | 93.143 | 93.143 | 92.108 | 93.143 | 95.169 | 91.059 | 93.143 | 85.582 | 86.71 | 87.569 | 92.108 | 94.163 | 94.163 | 95.169 | 96.161 |
| RB18 | 85.685 | 100 | 83.217 | 85.685 | 83.217 | 78.033 | 80.668 | 83.217 | 78.033 | 79.362 | 79.362 | 81.953 | 76.122 | 79.362 | 85.685 | 81.953 | 83.217 | 85.685 |
| GG5 | 93.143 | 83.217 | 100 | 89.995 | 89.995 | 86.71 | 87.821 | 89.995 | 87.821 | 87.821 | 82.096 | 85.582 | 84.108 | 91.059 | 91.059 | 91.059 | 91.059 | 92.108 |
| GG10 | 93.143 | 85.685 | 89.995 | 100 | 89.995 | 86.71 | 87.821 | 89.995 | 88.916 | 87.821 | 83.276 | 85.279 | 85.279 | 88.916 | 88.916 | 89.995 | 89.995 | 91.059 |
| Du179 | 93.143 | 83.217 | 89.995 | 89.995 | 100 | 88.916 | 87.821 | 93.143 | 87.821 | 88.916 | 84.438 | 84.108 | 82.918 | 88.916 | 88.916 | 87.821 | 89.995 | 91.059 |
| Du156 | 92.108 | 78.033 | 86.71 | 86.71 | 88.916 | 100 | 88.916 | 91.059 | 86.71 | 86.71 | 84.438 | 84.108 | 82.918 | 87.821 | 88.916 | 88.916 | 89.995 | 91.059 |
| Du151 | 93.143 | 80.668 | 87.821 | 87.821 | 88.916 | 88.916 | 100 | 96.161 | 87.821 | 87.821 | 85.582 | 85.279 | 84.108 | 88.916 | 91.059 | 87.821 | 92.108 | 91.059 |
| Du422 | 95.169 | 83.217 | 89.995 | 89.995 | 91.059 | 91.059 | 96.161 | 100 | 89.995 | 89.995 | 82.096 | 83.276 | 84.108 | 91.059 | 91.059 | 88.916 | 87.821 | 93.143 |
| Du201 | 91.059 | 78.033 | 87.821 | 88.916 | 87.821 | 88.916 | 87.821 | 89.995 | 100 | 89.995 | 78.445 | 84.438 | 84.108 | 91.059 | 91.059 | 88.916 | 89.995 | 88.916 |
| RB2R | 93.143 | 79.362 | 87.821 | 88.916 | 89.995 | 86.71 | 89.995 | 92.108 | 89.995 | 100 | 83.276 | 87.569 | 85.279 | 86.71 | 91.059 | 83.276 | 84.438 | 91.059 |
| CTSc2 | 85.582 | 79.362 | 82.096 | 82.096 | 84.438 | 82.096 | 78.445 | 84.438 | 78.445 | 83.276 | 100 | 85.279 | 81.71 | 80.898 | 85.582 | 85.582 | 86.71 | 83.276 |
| RB13 | 86.71 | 81.953 | 85.582 | 83.276 | 84.438 | 84.438 | 83.276 | 87.821 | 83.276 | 83.276 | 86.71 | 100 | 84.108 | 86.71 | 88.916 | 82.918 | 84.108 | 85.582 |
| Du204 | 87.569 | 76.122 | 84.108 | 85.279 | 82.918 | 84.108 | 85.279 | 84.108 | 85.279 | 85.279 | 81.71 | 84.108 | 100 | 85.279 | 85.279 | 82.918 | 84.108 | 85.279 |
| Du368 | 92.108 | 79.362 | 91.059 | 88.916 | 87.821 | 87.821 | 86.71 | 84.108 | 87.569 | 85.279 | 80.898 | 86.71 | 85.279 | 100 | 92.108 | 88.916 | 89.995 | 89.995 |
| Du123 | 94.163 | 85.685 | 91.059 | 88.916 | 89.995 | 89.995 | 91.059 | 88.916 | 91.059 | 91.059 | 85.582 | 88.916 | 85.279 | 92.108 | 100 | 93.143 | 94.163 | 92.108 |
| RB27 | 94.163 | 81.953 | 89.995 | 88.916 | 89.995 | 87.821 | 88.916 | 91.059 | 88.916 | 88.916 | 83.276 | 85.582 | 82.918 | 88.916 | 93.143 | 100 | 97.14 | 92.108 |
| RB21 | 95.169 | 83.217 | 91.059 | 89.995 | 89.995 | 88.916 | 89.995 | 92.108 | 89.995 | 89.995 | 84.438 | 86.71 | 84.108 | 89.995 | 94.163 | 97.14 | 100 | 93.143 |
| RB12 | 96.161 | 85.685 | 92.108 | 91.059 | 91.059 | 91.059 | 91.059 | 93.143 | 88.916 | 91.059 | 83.276 | 85.582 | 85.279 | 89.995 | 92.108 | 92.108 | 93.143 | 100 |

Figure 30

FRAGMENT A

MEPIDPNLEPWNHPGSQPNTPCNKCYCKYCSYHCLV (SEQ ID NO: 108)

FRAGMENT B

CKYCSYHCLVCFQTKGLGISYGRKKR (SEQ ID NO: 109)

FRAGMENT C

LGISYGRKKKRRQRRSTPPSSEDHQNPISKQPLPQTRGDPTGSEESKKKVESKTKTDPFD (SEQ ID NO: 110)

Intron site

Underline...mutations
Double underline...mutations used by others
Underline/bold...TAR binding site

Final version

X---------FRAGMENT C---------X-----FRAGMENT B------X-----FRAGMENT A-------X
LGISYGRKKKRRQRRSTPPSSEDHQNPISKQPLPQTRGDPTGSEESKKKVES

```
   1    AAGCTTGCCA CCATGGCTGC TCGCGCATCT ATCCTCAGAG GCGAAAAGTT GGATAAGTGG
  61    GAAAAAATCA GACTCAGGCC AGGAGGTAAA AAACACTACA TGCTGAAGCA TATCGTGTGG
 121    GCATCTAGGG AGTTGGAGAG ATTTGCACTG AACCCCGGAC TGCTGGAAAC CTCAGAGGGC
 181    TGTAAGCAAA TCATGAAACA GCTCCAACCA GCCTTGCAGA CCGGAACAGA AGAGCTGAAG
 241    TCCCTTTACA ATACCGTGGC AACCCTCTAT TGCGTCCACG AGAAGATCGA GGTGAGAGAC
 301    ACAAAGGAGG CCCTGGACAA AATCGAGGAG GAGCAGAATA AGTGCCAGCA GAAGACCCAG
 361    CAGGCAAAGG CTGCTGACGG AAAGGTCTCT CAGAACTATC CTATCGTTCA GAACCTTCAG
 421    GGGCAGATGG TGCACCAAGC AATCAGCCCT AGAACCCTGA ACGCATGGGT GAAGGTGATC
 481    GAGGAGAAAG CCTTTTCTCC CGAGGTTATC CCCATGTTTA CCGCCCTGAG CGAAGGCGCC
 541    ACTCCTCAAG ACCTGAACAC TATGCTGAAC ACAGTGGGAG GACACCAGGC CGCTATGCAG
 601    ATGTTGAAGG ATACCATCAA CGAGGAGGCA GCCGAATGGG ACCGCCTCCA CCCCGTGCAC
 661    GCCGGACCTA TCGCCCCCGG ACAAATGAGA GAACCTCGCG GAAGTGATAT TGCCGGTACT
 721    ACCAGCACCC TTCAAGAGCA GATTGCTTGG ATGACCAGCA ACCCACCCAT CCCAGTGGGC
 781    GATATTTACA AAAGGTGGAT TATTCTGGGG CTGAACAAAA TTGTGAGAAT GTACTCCCCC
 841    GTCTCCATCC TCGACATCCG CCAAGGACCC AAGGAGCCTT TTAGGGATTA CGTGGACAGA
 901    TTCTTCAAAA CCCTTAGAGC TGAGCAAGCC ACTCAGGAGG TTAAGAACTG GATGACAGAT
 961    ACTCTGCTCG TGCAAAACGC TAACCCCGAT TGCAAAACCA TCTTGAGAGC TCTCGGTCCA
1021    GGTGCCACCC TTGAGGAAAT GATGACAGCA TGTCAAGGCG TGGAGGACC TGGGCACAAG
1081    GCCAGAGTTC TCGCTGAGGC CATGAGCCAG ACAAACTCAG GCAATATCAT GATGCAGAGG
1141    AGTAACTTTA AGGGTCCCAG GAGAATCGTC AAGTGCTTCA ATTGTGGCAA GGAGGGTCAC
1201    ATTGCCAGGA ACTGCCGCGC CCCCAGGAAG AAAGGCTGCT GCAAGTGTGG CAAAGAGGGC
1261    CACCAGATGA AGGATTGCAC CGAGCGCCAA GCAAACTTCC TGGGAAAGAT TTGGCCCAGT
1321    CATAAGGGCC GCCCTGGCGA ATTCTGCGGC AAGAAGGCCA TCGGCACCGT GCTGGTGGGC
1381    CCCACCCCCG TGAACATCAT CGGCCGGAAC ATGCTGACCC AGCTGGGCTG CACCCTGAAC
1441    TTCCCCATCA GCCCCATCGA GACCGTGCCC GTGAAGCTGA AGCCCGGCAT GGACGGCCCC
1501    AAGGTGAAGC AGTGGCCCCT GACCGAGGTG AAGATCAAGG CCCTGACCGC CATCTGCGAG
1561    GAGATGGAGA AGGAGGGCAA GATCACCAAG ATCGGCCCCG AGAACCCCTA CAACACCCCC
1621    ATCTTCGCCA TCAAGAAGGA GGACAGCACC AAGTGGCGGA AGCTGGTGGA CTTCCGGGAG
1681    CTGAACAAGC GGACCCAGGA CTTCTGGGAG GTGCAGCTGG GCATCCCCCA CCCCGCCGGC
1741    CTGAAGAAGA AGAAGAGCGT GACCGTGCTG GACGTGGGCG ACGCCTACTT CAGCGTGCCC
1801    CTGGACGAGG GCTTCCGGAA GTACACCGCC TTCACCATCC CAGCATCAA CAACGAGACC
1861    CCCGGCATCC GGTACCAGTA CAACGTGCTG CCCCAGGGCT GGAAGGGCAG CCCCGCCATC
1921    TTCCAGGCCA GCATGACCAA GATCCTGGAG CCCTTCCGGG CCAAGAACCC CGACATCGTG
1981    ATCTACCAGT ACATGGCCGC CCTGTACGTG GGCAGCGACC TGGAGATCGG CCAGCACCGG
2041    GCCAAGATCG AGGAGCTGCG GGAGCACCTG CTGAAGTGGG GCTTCACCAC CCCCGACAAG
2101    AAGCACCAGA AGGAGCCCCC CTTCCTGTGG ATGGGCTACG AGCTGCACCC CGACAAGTGG
2161    ACCGTGCAGC CCATCCAGCT GCCCGAGAAG GACAGCTGGA CCGTGAACGA CATCCAGAAG
2221    CTGGTGGGCA AGCTGAACTG GACCAGCCAG ATCTACCCCG GCATCAAGGT GCGGCAGCTG
2281    TGCAAGCTGC TGCGGGGCAC CAAGGCCCTG ACCGACATCG TGCCCCTGAC CGAGGAGGCC
2341    GAGCTGGAGC TGGCCGAGAA CCGGCAGATC CTGAAGGAGC CCGTGCACGG CGTGTACTAC
2401    GACCCCAGCA AGGACCTGAT CGCCGAGATC CAGAAGCAGG GCGACGACCA GTGGACCTAC
2461    CAGATCTACC AGGAGCCCTT CAAGAACCTG AAAACCGGCA AGTACGCCAA GCGGCGGACC
2521    ACCCACACCA ACGACGTGAA GCAGCTGACC GAGGCCGTGC AGAAGATCAG CCTGGAGAGC
2581    ATCGTGACCT GGGGCAAGAC CCCCAAGTTC CGGCTGCCCA TCCAGAAGGA GACCTGGGAG
2641    ATCTGGTGGA CCGACTACTG GCAGGCCACC TGGATCCCCG AGTGGGAGTT CGTGAACAGC
2701    GGCCGCAAGC TTGCCACTAT GGTGGGCATC AGCTACGGCC GCAAGAAGCG CCGCCAGCGC
2761    CGCAGCACCC CGCCCAGCAG CGAGGACCAC CAGAACCCCA TCAGCAAGCA GCCCCTGCCC
2821    CAGACCCGCG GCGACCCCAC CGGCAGCGAG GAGAGCAAGA AGAAGCCCAG CAGCAAGACC
2881    AAGACCGACC CCTTCGACTG CAAGTACTGC AGCTACCACT GTCTGGTGTG CTTCCAGACC
2941    AAGGGCCTGG GCATCTCCTA CGGGCGCAAG AAACGGATGG AGCCCATCGA CCCCAAGCTG
3001    GAGCCCTGGA ACCACCCCGG CAGCCAGCCC AACACCCCCT GCAACAAGTG CTACTGCAAA
3061    TACTGCTCCT ACCACTGCCT CGTGGTGGGC TGGCCCGCCG TGCGCGAGCG CATCCGCCGC
3121    ACCGAGCCCG CCGCCGAGGG CGTGGGCCCC GCCAGCCAGG ACCTGGACAA GCACCGCGCC
3181    CTGACCAGCA GCAACACCGC CCACAACAAC CCCGACTGCG CCTGGCTGCA GGCCCAGGAG
3241    GAGGAGGAGG ACGTGGGCTT CCCCGTGCGC CCCCAGGTGC CCTGCGCCC CATGACCTAC
3301    AAGGCCGCCT TCGACCTGAG CTTCTTCCTG AAGGAGAAGG CGGCCTGGA GGGCCTGATC
3361    CACAGCAAGC GCCGCCAGGA CATCCTGGAC CTGTGGGTGT ACCACACCCA GGGCTACTTC
3421    CCCGACTGGC AGAACTACAC CCCCGGCCCC GGCGTGCGCT ACCCCCTGAC CTTCGGCTGG
3481    TGCTTCAAGC TGGTGCCCGT GGACCCCCGC GAGGTGGAGG AGGCCAACAA GGGCGAGAAC
3541    AACTGCCTGC TGCACCCCAT GAGCCAGCAC GGCATGGAGG ACGCCGACCG CGAGGTGCTG
3601    CGCTGGGTGT TCGACAGCAG CCTGGCCCGC CGCCACCTGG CCCGCGAGAA GCACCCCGAG
3661    TACTACAAGG ACTGAGAATT CTCTAGA
```

Figure 32a

```
  1  KLATMAARAS ILRGEKLDKW EKIRLRPGGK KHYMLEHIVW ASRELERFAL NPGLLETSEG
 61  CKQIMKQLQP ALQTSTEELK SLYNTVATLY CVHEKIEVRD TKEALOKIEE EQNKCQQKTQ
121  QAKAADGKVS QNYPIVQNLQ GQMVHQAISP RTLNAWVKVI EEKAFSPEVI PMFTALSEGA
181  TPQDLNTMLN TVGGHQAAMQ MLKDTINEEA AEWDRLHPVH AGPIAPGQMR EPRGSDIAGT
241  TSTLQEQIAW MTSNPPIPVG DIYKRWIILG LNKIVRMYSF VSILDIRQGP KEPFRDYVDR
301  FFKTLRAEQA TQEVKNWMTD TLLVQNANPD CKTILRALGP GATLEEMMTA CQGVGGPGHK
361  ARVLAEAMSQ TNSGNIMMQR SNFKGPRRIV KCFNCGKEGH IARNCRAPRK KGCWKCGKEG
421  HQMKDCTERQ ANFLGKIWPS HKGRPGEFCG KKAIGTVLVG PTPVNIIGRN MLTQLGCTLN
481  FPISPIETVP VKLKPGMDGP KVKQWPLTEV KIKALTAICE EMEKEGKITK IGPENPYNTP
541  IFAIKKEDST KWRKLVDFRE LNKRTQDFWE VQLGIPHPAG LKKKKSVTVL DVGDAYFSVP
601  LDEGFRKYTA FTIPSINNET PGIRYQYNVL PQGWKGSPAI FQASMTKILE PFRAKNPEIV
661  IYQYMAALYV GSDLEIGQHR AKIEELRSHL LKWGFTTPDK KHQKEPPFLW MGYELHPDKW
721  TVQPIQLPEK DSWTVNDIQK LVGKLNWTSQ IYPGIKVRQL CKLLRGTKAL PDIVPLTEEA
781  ELELAENREI LKEPVHGVYY DPSKDLIAEI QKQGDDQWTY QIYQEPFKNL RTGKYARRRT
841  THTNDVKQLT EAVQKISLES IVTWGKTPKF RLPIQKETWE IWWTDYWQAT WIPEWEFVNS
901  GRKLATPEGI SYGRKKRRQR RSTPPSSEDH QWPISEQPLF QTRGDPTGSE ESKKKVESKT
961  KTDPFDCKYC SYHCLVCFQT KGLGISYGRK KRMEPIDPNL EPWNHPGSQP NTPCEKCYCK
1021 YCSYHCLVWG WPAVRERIRR TEDAAEGVGP ASQDLDKHGA LTSSNTAHNN PDCAWLQAQE
1081 EEEDVGFFVR PQVPLRPMTY KAAFDLSFFL KEKGGLEGLI HSKRRQDILD LWVHTQGYF
1141 PDWQNYTPGP GVRYPLTFGW CFKLVPVDPR EVEEANKGEN NCLLHPMSQH GMEDADREVL
1201 RWVFDSSLAR RHLAREKHPE YYKU*EFBR
```

Bold= Restriction sites engineered

Bold Underlined= Kozac sequence and start ATG

Mutation to remove myristylation site of Gag (G6A) (Lee et al., 1994; Spearman et al., 1997)

Mutation to inactivate RT underlined (D666A, D667A) mutation (Chao S-F et al., 1995)

Start of shuffled Tat

Start of Truncated Nef

Figure 32b

```
ATGGCTGCTC GCGCATCTAT CCTCAGAGGC GAAAAGTTGG ATAAGTGGGA AAAAATCAGA¹
CTCAGGCCAG GAGGTAAAAA ACACTACATG CTGAAGCATA TCGTGTGGGC ATCTAGGGAG⁶¹
TTGGAGAGAT TTGCACTGAA CCCCGGACTG CTGGAAACCT CAGAGGGCTG TAAGCAAATC¹²¹
ATGAAACAGC TCCAACCAGC CTTGCAGACC GGAACAGAAG AGCTGAAGTC CCTTTACAAT¹⁸¹
ACCGTGGCAA CCCTCTATTG CGTCCACGAG AAGATCGAGG TGAGAGACAC AAAGGAGGCC²⁴¹
CTGGACAAAA TCGAGGAGGA GCAGAATAAG TGCCAGCAGA AGACCCAGCA GGCAAAGGCT³⁰¹
GCTGACGGAA AGGTCTCTCA GAACTATCCT ATCGTTCAGA ACCTTCAGGG GCAGATGGTG³⁶¹
CACCAAGCAA TCAGCCCTAG AACCCTGAAC GCATGGGTGA AGGTGATCGA GGAGAAAGCC⁴²¹
TTTTCTCCCG AGGTTATCCC CATGTTTACC GCCCTGAGCG AAGGCGCCAC TCCTCAAGAC⁴⁸¹
CTGAACACTA TGCTGAACAC AGTGGGAGGA CACCAGGCCG CTATGCAGAT GTTGAAGGAT⁵⁴¹
ACCATCAACG AGGAGGCAGC CGAATGGGAC CGCCTCCACC CCGTGCACGC CGGACCTATC⁶⁰¹
GCCCCCGGAC AAATGAGAGA ACCTCGCGGA AGTGATATTG CCGGTACTAC CAGCACCCTT⁶⁶¹
CAAGAGCAGA TTGCTTGGAT GACCAGCAAC CCACCCATCC CAGTGGGCGA TATTTACAAA⁷²¹
AGGTGGATTA TTCTGGGGCT GAACAAAATT GTGAGAATGT ACTCCCCCGT CTCCATCCTC⁷⁸¹
GACATCCGCC AAGGACCCAA GGAGCCTTTT AGGGATTACG TGGACAGATT CTTCAAAACC⁸⁴¹
CTTAGAGCTG AGCAAGCCAC TCAGGAGGTT AAGAACTGGA TGACAGATAC TCTGCTCGTG⁹⁰¹
CAAAACGCTA ACCCCGATTG CAAAACCATC TTGAGAGCTC TCGGTCCAGG TGCCACCCTT⁹⁶¹
GAGGAAATGA TGACAGCATG TCAAGGCGTG GGAGGACCTG GGCACAAGGC CAGAGTTCTC¹⁰²¹
GCTGAGGCCA TGAGCCAGAC AAACTCAGGC AATATCATGA TGCAGAGGAG TAACTTTAAG¹⁰⁸¹
GGTCCAGGA GAATCGTCAA GTGCTTCAAT TGTGGCAAGG AGGGTCACAT TGCCAGGAAC¹¹⁴¹
TGCCGCGCCC CCAGGAAGAA AGGCTGCTGG AAGTGTGGCA AAGAGGGCCA CCAGATGAAG¹²⁰¹
GATTGCACCG AGCGCCAAGC AAACTTCCTG GGAAAGATTT GGCCCAGTCA TAAGGGCCGC¹²⁶¹
CCTGGC                                                           ¹³²¹
```

Figure 34

```
MAARASILRG EKLDKWEKIR LRPGGKKHYM LKHIVWASRE LERFALNPGL LETSEGCKQI¹
MKQLQPALQT GTEELKSLYN TVATLYCVHE KIEVRDTKEA LDKIEEEQNK CQQKTQQAKA⁶¹
ADGKVSQNYP IVQNLQGQMV HQAISPRTLN AWVKVIEEKA FSPEVIPMFT ALSEGATPQD¹²¹
LNTMLNTVGG HQAAMQMLKD TINEEAAEWD RLHPVHAGPI APGQMREPRG SDIAGTTSTL¹⁸¹
QEQIAWMTSN PPIPVGDIYK RWIILGLNKI VRMYSPVSIL DIRQGPKEPF RDYVDRFFKT²⁴¹
LRAEQATQEV KNWMTDTLLV QNANPDCKTI LRALGPGATL EEMMTACQGV GGPGHKARVL³⁰¹
AEAMSQTNSG NIMMQRSNFK GPRRIVKCFN CGKEGHIARN CRAPRKKGCW KCGKEGHQMK³⁶¹
DCTERQANFL GKIWPSHKGR PG                                         ⁴²¹
```

Figure 35

```
GGGAAAGATT TGGCCCAGTC ATAAGGGCCG CCCTGGCGAA TTCTGCGGCA AGAAGGCCAT¹
CGGCACCGTG CTGGTGGGCC CCACCCCCGT GAACATCATC GGCCGGAACA TGCTGACCCA⁶¹
GCTGGGCTGC ACCCTGAACT TCCCCATCAG CCCCATCGAG ACCGTGCCCG TGAAGCTGAA¹²¹
GCCCGGCATG GACGGCCCCA AGGTGAAGCA GTGGCCCCTG ACCGAGGTGA AGATCAAGGC¹⁸¹
CCTGACCGCC ATCTGCGAGG AGATGGAGAA GGAGGGCAAG ATCACCAAGA TCGGCCCCGA²⁴¹
GAACCCCTAC AACACCCCCA TCTTCGCCAT CAAGAAGGAG GACAGCACCA AGTGGCGGAA³⁰¹
GCTGGTGGAC TTCCGGGAGC TGAACAAGCG GACCCAGGAC TTCGGGAGG TGCAGCTGGG³⁶¹
CATCCCCCAC CCCGCCGGCC TGAAGAAGAA GAAGAGCGTG ACCGTGCTGG ACGTGGGCGA⁴²¹
CGCCTACTTC AGCGTGCCCC TGGACGAGGG CTTCCGGAAG TACACCGCCT TCACCATCCC⁴⁸¹
CAGCATCAAC AACGAGACCC CCGGCATCCG GTACCAGTAC AACGTGGAGC CCCAGGGCTG⁵⁴¹
GAAGGGCAGC CCCGCCATCT TCCAGGCCAG CATGACCAAG ATCCTGGAGC CCTTCCGGGC⁶⁰¹
CAAGAACCCC GAGATCGTGA TCTACCAGTA CATGGCCGCC CTGTACGTGG GCAGCGACCT⁶⁶¹
GGAGATCGGC CAGCACCGGG CCAAGATCGA GGAGCTGCGG GAGCACCTGC TGAAGTGGGG⁷²¹
CTTCACCACC CCCGACAAGA AGCACCAGAA GGAGCCCCCC TTCCTGTGGA TGGGCTACGA⁷⁸¹
GCTGCACCCC GACAAGTGGA CCGTGCAGCC CATCCAGCTG CCCGAGAAGG ACAGCTGGAC⁸⁴¹
CGTGAACGAC ATCCAGAAGC TGGTGGGCAA GCTGAACTGG ACCAGCCAGA TCTACCCCGG⁹⁰¹
CATCAAGGTG CGGCAGCTGT GCAAGCTGCT GCGGGGCACC AAGGCCCTGA CCGACATCGT⁹⁶¹
GCCCCTGACC GAGGAGGCCG AGCTGGAGCT GGCCGAGAAC CGGGAGATCC TGAAGGAGCC¹⁰²¹
CGTGCACGGC GTGTACTACG ACCCCAGCAA GGACCTGATC GCCGAGATCC AGAAGCAGGG¹⁰⁸¹
CGACGACCAG TGGACCTACC AGATCTACCA GGAGCCCTTC AAGAACCTGA AAACCGGCAA¹¹⁴¹
GTACGCCAAG CGGCGGACCA CCCACACCAA CGACGTGAAG CAGCTGACCG AGGCCGTGCA¹²⁰¹
GAAGATCAGC CTGGAGAGCA TCGTGACCTG GGGCAAGACC CCCAAGTTCC GGCTGCCCAT¹²⁶¹
CCAGAAGGAG ACCTGGGAGA TCTGGTGGAC CGACTACTGG CAGGCCACCT GGATCCCCGA¹³²¹
GTGGGAGTTC GTGAACA                                              ¹³⁸¹
```

Figure 36

```
CGKKAIGTVL VGPTPVNIIG RNMLTQLGCT LNFPISPIET VPVKLKPGMD GPKVKQWPLT¹
EVKIKALTAI CEEMEKEGKI TKIGPENPYN TPIFAIKKED STKWRKLVDF RELNKRTQDF⁶¹
WEVQLGIPHP AGLKKKKSVT VLDVGDAYFS VPLDEGFRKY TAFTIPSINN ETPGIRYQYN¹²¹
VLPQGWKGSP AIFQASMTKI LEPFRAKNPE IVIYQYMAAL YVGSDLEIGQ HRAKIEELRE¹⁸¹
HLLKWGFTTP DKKHQKEPPF LWMGYELHPD KWTVQPIQLP EKDSWTVNDI QKLVGKLNWT²⁴¹
SQIYPGIKVR QLCKLLRGTK ALTDIVPLTE EAELELAENR EILKEPVHGV YYDPSKDLIA³⁰¹
EIQKQGDDQW TYQIYQEPFK NLKTGKYAKR RTTHTNDVKQ LTEAVQKISL ESIVTWGKTP³⁶¹
KFRLPIQKET WEIWWTDYWQ ATWIPEWEFV N                              ⁴²¹
```

Figure 37

SEQUENCE LISTING

```
<160> NUMBER OF SEQ ID NOS: 38

<210> SEQ ID NO 1
<211> LENGTH: 306
<212> TYPE: DNA
<213> ORGANISM: Human immunodeficiency virus type 1

<400> SEQUENCE: 1
atggagccaa tagatcctaa cctagagccc tggaaccatc caggaagtca gcctaatact     60
ccttgtaata actgctattg taaacactgt agctaccatt gtctagtttg ctttcagaca    120
aaaggcttag gcatttccta tggcaggaag aagcggagac agcgacgaag cactcctcca    180
agcagtgaag atcatcaaaa tcctatatca aagcaaccct tatcccaaac ccgagggggac    240 ccgacaggct cggaagaatc gaagaagaag gtggagagca agacaaagac agatccattc    300
gattag                                                               306

<210> SEQ ID NO 2
<211> LENGTH: 101
<212> TYPE: PRT
<213> ORGANISM: Human immunodeficiency virus type 1

<400> SEQUENCE: 2

Met Glu Pro Ile Asp Pro Asn Leu Glu Pro Trp Asn His Pro Gly Ser
1               5                   10                  15

Gln Pro Asn Thr Pro Cys Asn Asn Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Arg Arg Gln Arg Arg Ser Thr Pro Pro Ser Ser Glu Asp
    50                  55                  60

His Gln Asn Pro Ile Ser Lys Gln Pro Leu Ser Gln Thr Arg Gly Asp
65                  70                  75                  80
```

Pro Thr Gly Ser Glu Glu Ser Lys Lys Lys Val Glu Ser Lys Thr Lys
             85                  90                  95

Thr Asp Pro Phe Asp
            100

<210> SEQ ID NO 3
<211> LENGTH: 306
<212> TYPE: DNA
<213> ORGANISM: Human immunodeficiency virus type 1

<400> SEQUENCE: 3
atggagccaa tagatcctaa cctagagccc tggaaccatc caggaagtca acctaacact        60
ccttgtacta atgctattg taaatactgc agctatcatt gtctagtttg ctttcagaca       120
aaaggcttag gcatttccta tggcaggaag aagcggagac agcgacgaag cactcctcca       180
agcagtgagg atcatcaaaa tcttatatca gagcagccct taccccaagc ccgaggggtc       240
ccgacaggct cggaagaatc gaagaagaag gtggagagca agacaaaaac agatccattc       300
gattag                                                                  306

<210> SEQ ID NO 4
<211> LENGTH: 101
<212> TYPE: PRT
<213> ORGANISM: Human immunodeficiency virus type 1

<400> SEQUENCE: 4

Met Glu Pro Ile Asp Pro Asn Leu Glu Pro Trp Asn His Pro Gly Ser
1               5                   10                  15

Gln Pro Asn Thr Pro Cys Thr Lys Cys Tyr Cys Lys Tyr Cys Ser Tyr
            20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Thr Pro Pro Ser Ser Glu Asp
        50                  55                  60

His Gln Asn Leu Ile Ser Glu Gln Pro Leu Pro Gln Ala Arg Gly Val
65                  70                  75                  80

Pro Thr Gly Ser Glu Glu Ser Lys Lys Lys Val Glu Ser Lys Thr Lys
             85                  90                  95

Thr Asp Pro Phe Asp
            100

<210> SEQ ID NO 5
<211> LENGTH: 618
<212> TYPE: DNA
<213> ORGANISM: Human immunodeficiency virus type 1

<400> SEQUENCE: 5 atgggggggca agtggtcaaa aagcagcata gtgggatggc ctgctgtaag agaaagaata       60
agaagaactg agccagcagc agagggagta ggaccagcat ctcaagactt agataaacat      120
ggagcgctta caagcagcaa cacagcccac aataatcctg actgtgcctg gctacaagca      180
caagaggagg aagaagacgt aggttttcca gtcagacctc aggtgcctct aagaccaatg      240
acttataagg cagcattcga tctcagcttc tttttaaaag aaaaggggggg actggaaggg      300 ttaattcact ctaagagaag acaagacatt cttgatttgt gggtctatca cacacaaggc      360
tacttccctg attggcaaaa ctacacgccg ggaccaggga tcagataccc actgaccttt      420
ggatggtgct tcaagctagt gccagttgat ccaagggaag tagaagaggc caacaaagga      480

```
gaaaacaact gtttgctaca ccctatgagc cagcatggaa tggaggatgc agacagagaa    540
gtattaagat gggtgtttga cagcagtcta gcacgcagac acctggcccg cgagaaacat    600
ccggagtatt acaaagac                                                  618
```

<210> SEQ ID NO 6
<211> LENGTH: 207
<212> TYPE: PRT
<213> ORGANISM: Human immunodeficiency virus type 1

<400> SEQUENCE: 6

```
Met Gly Gly Lys Trp Ser Lys Ser Ser Ile Val Gly Trp Pro Ala Val
 1               5                  10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Pro Asp Cys Ala Trp Leu Gln Ala Gln Glu Glu Glu
    50                  55                  60

Pro Glu Val Gly Phe Pro Val Arg Pro Gln Val Pro Leu Arg Pro Met
65                  70                  75                  80

Thr Tyr Lys Ala Ala Phe Asp Leu Ser Phe Phe Leu Lys Glu Lys Gly
                85                  90                  95

Gly Leu Glu Gly Leu Ile Tyr Ser Lys Lys Arg Gln Asp Ile Leu Asp
            100                 105                 110

Leu Trp Val Tyr His Thr Gln Gly Tyr Phe Pro Asp Trp Gln Asn Tyr
        115                 120                 125

Thr Pro Gly Pro Gly Val Arg Leu Pro Leu Thr Phe Gly Trp Cys Phe
    130                 135                 140

Lys Leu Val Pro Val Asp Pro Glu Glu Val Glu Glu Ala Asn Lys Gly
145                 150                 155                 160

Glu Asn Asn Cys Leu Leu His Pro Leu Ser Gln His Gly Met Glu Asp
                165                 170                 175

Ala Asp Arg Glu Val Leu Lys Trp Val Phe Asp Ser Ser Leu Ala Arg
            180                 185                 190

Arg His Leu Ala Arg Glu Lys His Pro Glu Tyr Tyr Lys Asp Cys
        195                 200                 205
```

<210> SEQ ID NO 7
<211> LENGTH: 324
<212> TYPE: DNA
<213> ORGANISM: Human immunodeficiency virus type 1

<400> SEQUENCE: 7

```
atggcaggaa gaagcggaga cagcgacgaa gcactcctcc aagcagtgaa gatcatcaaa     60
atcctatatc aaagcaaccc ttatcccaaa cccgagggga cccgacaggc tcggaagaat    120
cgaagaagaa ggtggagagc aagacaaaga cagatccatt cgattagtga gcggattctt    180
agcacttgcc tgggacgatc tgcggagcct gtgcctcttc agctaccacc aattgagaga    240
cttcatattg actgcagcga gagcagcgga acttctggga cgcagcagtc tcaggggact    300
gcagagaggg tgggaagtcc ttaa                                           324
```

<210> SEQ ID NO 8
<211> LENGTH: 107
<212> TYPE: PRT
<213> ORGANISM: Human immunodeficiency virus type 1

-continued

```
<400> SEQUENCE: 8

Met Ala Gly Arg Ser Gly Asp Ser Asp Glu Ala Leu Leu Gln Ala Val
1               5                   10                  15

Lys Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Ser Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gly Thr Ala Glu Arg Val Gly Ser Pro
            100                 105

<210> SEQ ID NO 9
<211> LENGTH: 392
<212> TYPE: DNA
<213> ORGANISM: Human immunodeficiency virus type 1

<400> SEQUENCE: 9
ggatccgcgg ccgcaagctt gccaccatgg taggcatttc ctatggcagg aagaagcgga      60
gacagcgacg aagcactcct ccaagcagtg aggatcatca aaatcctata tcaaagcagc    120
ccttacccca aacccgaggg gacccgacag gctcggaaga atcgaagaag aaggtggaga    180
gcaagacaaa aacagatcca ttcgattgta aatactgcag ctatcattgt ctagtttgct    240
ttcagacaaa aggcttaggt attagctatg aaggaagaa acggatggag ccaatagatc    300
ctaacctaga gccctggaac catccaggaa gtcaacctaa cactccttgt aataaatgct    360
attgtaagta ctgttcatat cattgcctag tt                                  392

<210> SEQ ID NO 10
<211> LENGTH: 392
<212> TYPE: DNA
<213> ORGANISM: Human immunodeficiency virus type 1

<400> SEQUENCE: 10
ggatccgcgg ccgcaagctt gccaccatgg tgggcatcag ctacggccgc aagaagcgcc     60
gccagcgccg cagcaccccg cccagcagcg aggaccacca gaaccccatc agcaagcagc   120
ccctgcccca gacccgcggc gaccccaccg gcagcgagga gagcaagaag aaggtggaga   180
gcaagaccaa gaccgacccc ttcgactgca agtactgcag ctaccactgt ctggtgtgct   240
tccagaccaa gggcctgggc atctcctacg ggcgcaagaa acggatggag cccatcgacc   300
ccaacctgga gccctggaac caccccggca gccagcccaa caccccctgc aacaagtgct   360 actgcaaaata ctgctcctac cactgcctcg tg                                 392

<210> SEQ ID NO 11
<211> LENGTH: 122
<212> TYPE: PRT
<213> ORGANISM: Human immunodeficiency virus type 1

<400> SEQUENCE: 11

Met Leu Gly Ile Ser Tyr Gly Arg Lys Lys Arg Arg Gln Arg Arg Ser
1               5                   10                  15
```

```
Thr Pro Pro Ser Ser Glu Asp His Gln Asn Pro Ile Ser Lys Gln Pro
         20                  25                  30

Leu Pro Gln Thr Arg Gly Asp Pro Thr Gly Ser Glu Glu Ser Lys Lys
         35                  40                  45

Lys Val Glu Ser Lys Thr Lys Thr Asp Pro Phe Asp Cys Lys Tyr Cys
 50                  55                  60

Ser Tyr His Cys Leu Val Cys Phe Gln Thr Lys Gly Leu Gly Ile Ser
 65                  70                  75                  80

Tyr Gly Arg Lys Lys Arg Met Glu Pro Ile Asp Pro Asn Leu Glu Pro
             85                  90                  95

Trp Asn His Pro Gly Ser Gln Pro Asn Thr Pro Cys Asn Lys Cys Tyr
            100                 105                 110

Cys Lys Tyr Cys Ser Tyr His Cys Leu Val
            115                 120
```

```
<210> SEQ ID NO 12
<211> LENGTH: 617
<212> TYPE: DNA
<213> ORGANISM: Human immunodeficiency virus type 1

<400> SEQUENCE: 12
gtgggatggc ctgctgtaag agaaagaata agaagaactg agccagcagc agagggagta     60
ggaccagcat ctcaagactt agataaacat ggagcgctta caagcagcaa cacagcccac    120
aataatcctg actgtgcctg gctacaagca caagaggagg aagaagacgt aggttttcca    180
gtcagacctc aggtgcctct aagaccaatg acttataagg cagcattcga tctcagcttc    240
tttttaaaag aaaaggggggg actggaaggg ttaattcact ctaagagaag acaagacatt    300
cttgatttgt gggtctatca cacacaaggc tacttccctg attggcaaaa ctacacgccg    360
ggaccaggag tcagataccc actgaccttt ggatggtgct tcaagctagt gccagttgat    420
ccaagggaag tagaagaggc caacaaagga gaaaacaact gtttgctaca ccctatgagc    480
cagcatggaa tggaggatgc agacagagaa gtattaagat gggtgtttga cagcagtcta    540
gcacgcagac acctggcccg cgagaaacat ccggagtatt acaaagacta ggaattctct    600
agagcggccg cgtcgac                                                   617
```

```
<210> SEQ ID NO 13
<211> LENGTH: 617
<212> TYPE: DNA
<213> ORGANISM: Human immunodeficiency virus type 1

<400> SEQUENCE: 13
gtgggctggc cgccgtgcg cgagcgcatc cgccgcaccg agcccgccgc cgagggcgtg     60
ggccccgcca gccaggacct ggacaagcac ggcgccctga ccagcagcaa caccgcccac    120
aacaaccccg actgcgcctg ctgcaggcc caggaggagg aggaggacgt gggcttcccc    180
gtgcgccccc aggtgcccct gcgccccatg acctacaagg ccgccttcga cctgagcttc    240
ttcctgaagg agaagggcgg cctggagggc ctgatccaca gcaagcgccg ccaggacatc    300
ctggacctgt gggtgtacca cacccagggc tacttccccg actggcagaa ctacaccccc    360
ggccccggcg tgcgctaccc cctgaccttc ggctggtgct tcaagctggt gccgtggac    420 ccccgcgagg tggaggaggc caacaagggc gagaacaact gcctgctgca ccccatgagc    480
cagcacggca tggaggacgc cgaccgcgag gtgctgcgct gggtgttcga cagcagcctg    540
```

```
gcccgccgcc acctggcccg cgagaagcac cccgagtact acaaggactg agaattctct      600
agagcggccg cgtcgac                                                    617
```

<210> SEQ ID NO 14
<211> LENGTH: 196
<212> TYPE: PRT
<213> ORGANISM: Human immunodeficiency virus type 1

<400> SEQUENCE: 14

```
Val Gly Trp Pro Ala Val Arg Glu Arg Ile Arg Arg Thr Glu Pro Ala
1               5                   10                  15

Ala Glu Gly Val Gly Pro Ala Ser Gln Asp Leu Asp Lys His Gly Ala
            20                  25                  30

Leu Thr Ser Ser Asn Thr Ala His Asn Asn Pro Asp Cys Ala Trp Leu
        35                  40                  45

Gln Ala Gln Glu Glu Glu Asp Val Gly Phe Pro Val Arg Pro Gln
    50                  55                  60

Val Pro Leu Arg Pro Met Thr Tyr Lys Ala Ala Phe Asp Leu Ser Phe
65                  70                  75                  80

Phe Leu Lys Glu Lys Gly Gly Leu Glu Gly Leu Ile His Ser Lys Arg
                85                  90                  95

Arg Gln Asp Ile Leu Asp Leu Trp Val Tyr His Thr Gln Gly Tyr Phe
            100                 105                 110

Pro Asp Trp Gln Asn Tyr Thr Pro Gly Pro Gly Val Arg Tyr Pro Leu
        115                 120                 125

Thr Phe Gly Trp Cys Phe Lys Leu Val Pro Val Asp Pro Arg Glu Val
    130                 135                 140

Glu Glu Ala Asn Lys Gly Glu Asn Asn Cys Leu Leu His Pro Met Ser
145                 150                 155                 160

Gln His Gly Met Glu Asp Ala Asp Arg Glu Val Leu Arg Trp Val Phe
                165                 170                 175

Asp Ser Ser Leu Ala Arg Arg His Leu Ala Arg Glu Lys His Pro Glu
            180                 185                 190

Tyr Tyr Lys Asp
        195
```

<210> SEQ ID NO 15
<211> LENGTH: 1009
<212> TYPE: DNA
<213> ORGANISM: Human immunodeficiency virus type 1

<400> SEQUENCE: 15

```
ggatccgcgg ccgcaagctt gccaccatgg taggcatttc ctatggcagg aagaagcgga       60 gacgcgacg aagcactcct ccaagcagtg aggatcatca aaatcctata tcaaagcagc       120
ccttacccca acccgagggg acccgacag gctcggaaga atcgaagaag aaggtggaga       180
gcaagacaaa aacagatcca ttcgattgta atactgcag ctatcattgt ctagtttgct       240
ttcagacaaa aggcttaggc atttcctatg caggaagaa gcggatggag ccaatagatc       300
ctaacctaga gccctggaac catccaggaa gtcaacctaa cactccttgt aataaatgct       360 attgtaaaata ctgcagctat cattgtctag ttgtgggatg gcctgctgta agagaaagaa       420
taagaagaac tgagccagca gcagagggag taggaccagc atctcaagac ttagataaac       480
atggagcgct tacaagcagc aacacagccc acaataatcc tgactgtgcc tggctacaag       540
cacaagagga ggaagaagac gtaggttttc cagtcagacc tcaggtgcct ctaagaccaa       600
```

-continued

```
tgacttataa ggcagcattc gatctcagct tcttttaaa agaaaagggg ggactggaag    660
ggttaattca ctctaagaga agacaagaca ttcttgattt gtgggtctat acacacaag    720 gctacttccc tgattggcaa aactacacgc cgggaccagg agtcagatac ccactgacct   780
ttggatggtg cttcaagcta gtgccagttg atccaaggga agtagaagag gccaacaaag   840
gagaaaacaa ctgtttgcta caccctatga gccagcatgg aatggaggat gcagacagag   900
aagtattaag atgggtgttt gacagcagtc tagcacgcag acacctggcc cgcgagaaac   960
atccggagta ttacaaagac taggaattct ctagagcggc cgcgtcgac              1009
```

<210> SEQ ID NO 16
<211> LENGTH: 318
<212> TYPE: PRT
<213> ORGANISM: Human immunodeficiency virus type 1

<400> SEQUENCE: 16

```
Met Val Gly Ile Ser Tyr Gly Arg Lys Lys Arg Gln Arg Arg Ser
 1               5                  10                  15

Thr Pro Ser Ser Glu Asp His Gln Asn Pro Ile Ser Lys Gln Pro
             20                  25                  30

Leu Pro Gln Thr Arg Gly Asp Pro Thr Gly Ser Glu Glu Ser Lys Lys
         35                  40                  45

Lys Val Glu Ser Lys Thr Lys Thr Asp Pro Phe Asp Cys Lys Tyr Cys
 50                  55                  60

Ser Tyr His Cys Leu Val Cys Phe Gln Thr Lys Gly Leu Gly Ile Ser
 65                  70                  75                  80

Tyr Gly Arg Lys Lys Arg Met Glu Pro Ile Asp Pro Asn Leu Glu Pro
                 85                  90                  95

Trp Asn His Pro Gly Ser Gln Pro Asn Thr Pro Cys Asn Lys Cys Tyr
            100                 105                 110

Cys Lys Tyr Cys Ser Tyr His Cys Leu Val Val Gly Trp Pro Ala Val
        115                 120                 125

Arg Glu Arg Ile Arg Arg Thr Glu Pro Ala Ala Glu Gly Val Gly Pro
    130                 135                 140

Ala Ser Gln Asp Leu Asp Lys His Gly Ala Leu Thr Ser Ser Asn Thr
145                 150                 155                 160

Ala His Asn Asn Pro Asp Cys Ala Trp Leu Gln Ala Gln Glu Glu Glu
                165                 170                 175

Glu Asp Val Gly Phe Pro Val Arg Pro Gln Val Pro Leu Arg Pro Met
            180                 185                 190

Thr Tyr Lys Ala Ala Phe Asp Leu Ser Phe Phe Leu Lys Glu Lys Gly
        195                 200                 205

Gly Leu Glu Gly Leu Ile His Ser Lys Arg Arg Gln Asp Ile Leu Asp
    210                 215                 220

Leu Trp Val Tyr His Thr Gln Gly Tyr Phe Pro Asp Trp Gln Asn Tyr
225                 230                 235                 240

Thr Pro Gly Pro Gly Val Arg Tyr Pro Leu Thr Phe Gly Trp Cys Phe
                245                 250                 255

Lys Leu Val Pro Val Asp Pro Arg Glu Val Glu Glu Ala Asn Lys Gly
            260                 265                 270

Glu Asn Asn Cys Leu Leu His Pro Met Ser Gln His Gly Met Glu Asp
        275                 280                 285
```

```
Ala Asp Arg Glu Val Leu Arg Trp Val Phe Asp Ser Ser Leu Ala Arg
    290                 295                 300

Arg His Leu Ala Arg Glu Lys His Pro Glu Tyr Tyr Lys Asp
305                 310                 315
```

<210> SEQ ID NO 17
<211> LENGTH: 1009
<212> TYPE: DNA
<213> ORGANISM: Human immunodeficiency virus type 1

<400> SEQUENCE: 17

```
ggatccgcgg ccgcaagctt gccaccatgg tgggcatcag ctacggccgc aagaagcgcc    60
gccagcgccg cagcaccccg cccagcagcg aggaccacca gaaccccatc agcaagcagc   120
ccctgcccca gacccgcggc gaccccaccg gcagcgagga gagcaagaag aaggtggaga   180
gcaagaccaa gaccgacccc ttcgactgca gtactgcag ctaccactgt ctggtgtgct    240
tccagaccaa gggcctgggc atctcctacg gcgcaagaa acggatggag cccatcgacc    300
ccaacctgga gcctggaac caccccggca gcagcccaa caccccctgc aacaagtgct    360
actgcaaata ctgctcctac cactgcctcg tggtgggctg gccgccgtg cgcgagcgca    420
tccgccgcac cgagcccgcc gccgagggcg tgggccccgc cagccaggac ctggacaagc    480
acggcgccct gaccagcagc aacaccgccc acaacaaccc cgactgcgcc tggctgcagg    540
cccaggagga ggaggaggac gtgggcttcc ccgtgcgccc ccaggtgccc ctgcgcccca    600
tgacctacaa ggccgccttc gacctgagct tcttcctgaa ggagaagggc ggcctggagg    660
gcctgatcca cagcaagcgc cgccaggaca tcctggacct gtgggtgtac cacacccagg    720
gctacttccc cgactggcag aactacaccc ccggccccgg cgtgcgctac cccctgacct    780
tcggctggtg cttcaagctg gtgcccgtgg accccgcga ggtggaggag gccaacaagg    840
gcgagaacaa ctgcctgctg cacccccatga gccagcacgg catggaggac gccgaccgcg    900
aggtgctgcg ctgggtgttc gacagcagcc tggcccgccg ccacctggcc cgcgagaagc    960
accccgagta ctacaaggac tgagaattct ctagagcggc cgcgtcgac              1009
```

<210> SEQ ID NO 18
<211> LENGTH: 101
<212> TYPE: PRT
<213> ORGANISM: Human immunodeficiency virus type 1

<400> SEQUENCE: 18

```
Met Glu Pro Val Asp Pro Asn Leu Glu Pro Trp Asn His Pro Gly Ser
1               5                   10                  15

Gln Pro Lys Thr Ala Cys Asn Lys Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Ala Pro Pro Ser Ser Glu Asp
    50                  55                  60

His Gln Asn Leu Ile Ser Lys Gln Pro Leu Pro Gln Thr Arg Gly Asp
65                  70                  75                  80

Pro Thr Gly Ser Glu Glu Ser Lys Lys Val Glu Ser Lys Thr Glu
                85                  90                  95

Thr Asp Pro Phe Asp
            100
```

```
<210> SEQ ID NO 19
<211> LENGTH: 207
<212> TYPE: PRT
<213> ORGANISM: Human immunodeficiency virus type 1

<400> SEQUENCE: 19

Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Ala Asp Cys Ala Trp Leu Gln Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Gly Ala Phe Asp Leu Ser Phe Phe Leu Lys Glu Lys Gly
                85                  90                  95

Gly Leu Glu Gly Leu Ile Tyr Ser Lys Lys Arg Gln Glu Ile Leu Asp
            100                 105                 110

Leu Trp Val Tyr His Thr Gln Gly Phe Phe Pro Asp Trp Gln Asn Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Arg Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser Ser Leu Ala Arg
            180                 185                 190

Arg His Met Ala Arg Glu Leu His Pro Glu Tyr Tyr Lys Asp Cys
        195                 200                 205

<210> SEQ ID NO 20
<211> LENGTH: 107
<212> TYPE: PRT
<213> ORGANISM: Human immunodeficiency virus type 1

<400> SEQUENCE: 20

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Pro Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gln Thr Thr Glu Gly Val Gly Ser Pro
            100                 105
```

```
<210> SEQ ID NO 21
<211> LENGTH: 20
<212> TYPE: DNA
<213> ORGANISM: Human immunodeficiency virus type 1

<400> SEQUENCE: 21
ggccgcagag ggaaccatac                                              20

<210> SEQ ID NO 22
<211> LENGTH: 21
<212> TYPE: DNA
<213> ORGANISM: Human immunodeficiency virus type 1

<400> SEQUENCE: 22
gccctgtctt attcttctag g                                            21

<210> SEQ ID NO 23
<211> LENGTH: 21
<212> TYPE: DNA
<213> ORGANISM: Human immunodeficiency virus type 1

<400> SEQUENCE: 23
cctcaatatc cccatcactc t                                            21

<210> SEQ ID NO 24
<211> LENGTH: 20
<212> TYPE: DNA
<213> ORGANISM: Human immunodeficiency virus type 1

<400> SEQUENCE: 24
tgccagcata gcagaatagg                                              20

<210> SEQ ID NO 25
<211> LENGTH: 24
<212> TYPE: DNA
<213> ORGANISM: Human immunodeficiency virus type 1

<400> SEQUENCE: 25
ctatcaatgc tcctactcct aatc                                         24

<210> SEQ ID NO 26
<211> LENGTH: 21
<212> TYPE: DNA
<213> ORGANISM: Human immunodeficiency virus type 1

<400> SEQUENCE: 26
gatagtagga ggcttgatag g                                            21

<210> SEQ ID NO 27
<211> LENGTH: 18
<212> TYPE: DNA
<213> ORGANISM: Human immunodeficiency virus type 1

<400> SEQUENCE: 27
ggtgtactcg ctatagtg                                                18

<210> SEQ ID NO 28
<211> LENGTH: 20
<212> TYPE: DNA
<213> ORGANISM: Human immunodeficiency virus type 1

<400> SEQUENCE: 28
ccttcagcta ctgctattgc                                              20
```

<210> SEQ ID NO 29
<211> LENGTH: 3687
<212> TYPE: DNA
<213> ORGANISM: Human immunodeficiency virus type 1

<400> SEQUENCE: 29

```
aagcttgcca ccatggctgc tcgcgcatct atcctcagag gcgaaaagtt ggataagtgg        60
gaaaaaatca gactcaggcc aggaggtaaa aaacactaca tgctgaagca tatcgtgtgg       120
gcatctaggg agttggagag atttgcactg aaccccggac tgctggaaac ctcagagggc       180
tgtaagcaaa tcatgaaaca gctccaacca gccttgcaga ccggaacaga agagctgaag       240
tccctttaca ataccgtggc aaccctctat tgcgtccacg agaagatcga ggtgagagac       300
acaaaggagg ccctggacaa aatcgaggag gagcagaata gtgccagca gaagacccag       360
caggcaaagg ctgctgacgg aaaggtctct cagaactatc ctatcgttca gaaccttcag       420
gggcagatgg tgcaccaagc aatcagccct agaaccctga cgcatgggt gaaggtgatc       480
gaggagaaag ccttttctcc cgaggttatc cccatgttta ccgccctgag cgaaggcgcc       540
actcctcaag acctgaacac tatgctgaac acagtgggag acaccaggc cgctatgcag       600
atgttgaagg ataccatcaa cgaggaggca gccgaatggg accgcctcca ccccgtgcac       660
gccggaccta tcgcccccgg acaaatgaga gaacctcgcg gaagtgatat tgccggtact       720
accagcaccc ttcaagagca gattgcttgg atgaccagca cccacccat cccagtgggc       780
gatatttaca aaaggtggat tattctgggg ctgaacaaaa ttgtgagaat gtactccccc       840
gtctccatcc tcgacatccg ccaaggaccc aaggagcctt ttagggatta cgtggacaga       900
ttcttcaaaa cccttagagc tgagcaagcc actcaggagg ttaagaactg gatgacagat       960
actctgctcg tgcaaaacgc taaccccgat tgcaaaacca tcttgagagc tctcggtcca      1020
ggtgccaccc ttgaggaaat gatgacagca tgtcaaggcg tgggaggacc tgggcacaag      1080
gccagagttc tcgctgaggc catgagccag acaaactcag caatatcat gatgcagagg      1140
agtaacttta gggtcccag gagaatcgtc aagtgcttca attgtggcaa ggagggtcac      1200
attgccagga actgccgcgc ccccaggaag aaaggctgct ggaagtgtgg caaagagggc      1260
caccagatga aggattgcac cgagcgccaa gcaaacttcc tgggaaagat ttggcccagt      1320
cataagggcc gccctggcga attcgcggc aagaaggcca tcggcaccgt gctggtgggc      1380
cccaccccg tgaacatcat cggccggaac atgctgaccc agctgggctg caccctgaac      1440
ttccccatca gccccatcga gaccgtgccc gtgaagctga gcccggcat ggacggcccc      1500
aaggtgaagc agtggcccct gaccgaggtg aagatcaagg ccctgaccgc catctgcgag      1560
gagatggaga aggagggcaa gatcaccaag atcggccccg agaacccta caacaccccc      1620
atcttcgcca tcaagaagga ggacagcacc aagtggcgga gctggtgga cttccgggag      1680
ctgaacaagc ggacccagga cttctgggag gtgcagctgg gcatccccca ccccgccggc      1740
ctgaagaaga gaagagcgt gaccgtgctg acgtgggcg acgcctactt cagcgtgccc      1800
ctggacgagg gcttccggaa gtacaccgcc ttcaccatcc ccagcatcaa caacgagacc      1860
cccggcatcc ggtaccagta caacgtgctg ccccagggct ggaagggcag ccccgccatc      1920
ttccaggcca gcatgaccaa gatcctggag cccttccggg ccaagaaccc cgagatcgtg      1980
atctaccagt acatggccgc cctgtacgtg ggcagcgacc tggagatcgg ccagcaccgg      2040
gccaagatcg aggagctgcg ggagcacctg ctgaagtggg gcttcaccac ccccgacaag      2100
aagcaccaga aggagccccc cttcctgtgg atgggctacg agctgcaccc cgacaagtgg      2160
```

-continued

```
accgtgcagc ccatccagct gcccgagaag gacagctgga ccgtgaacga catccagaag    2220
ctggtgggca agctgaactg gaccagccag atctaccccg gcatcaaggt gcggcagctg    2280
tgcaagctgc tgcggggcac caaggccctg accgacatcg tgcccctgac cgaggaggcc    2340
gagctggagc tggccgagaa ccgggagatc ctgaaggagc ccgtgcacgg cgtgtactac    2400
gaccccagca aggacctgat cgccgagatc cagaagcagg gcgacgacca gtggacctac    2460
cagatctacc aggagccctt caagaacctg aaaaccggca gtacgccaa gcggcggacc    2520
acccacacca cgacgtgaa gcagctgacc gaggccgtgc agaagatcag cctggagagc    2580
atcgtgacct ggggcaagac ccccaagttc cggctgccca tccagaagga gacctgggag    2640
atctggtgga ccgactactg gcaggccacc tggatccccg agtgggagtt cgtgaacagc    2700
ggccgcaagc ttgccaccat ggtgggcatc agctacggcc gcaagaagcg ccgccagcgc    2760
cgcagcaccc cgcccagcag cgaggaccac cagaaccca tcagcaagca gcccctgccc    2820
cagacccgcg cgaccccac cggcagcgag gagagcaaga agaaggtgga gagcaagacc    2880
aagaccgacc ccttcgactg caagtactgc agctaccact gtctggtgtg cttccagacc    2940
aagggcctgg gcatctccta cgggcgcaag aaacggatgg agcccatcga ccccaacctg    3000
gagccctgga ccaccccgg cagccagccc aacacccct gcaacaagtg ctactgcaaa    3060
tactgctcct accactgcct cgtggtgggc tggcccgccg tgcgcgagcg catccgccgc    3120
accgagcccg ccgccgaggg cgtgggcccc gccagccagg acctggacaa gcacggcgcc    3180
ctgaccagca gcaacaccgc ccacaacaac cccgactgcg cctggctgca ggcccaggag    3240
gaggaggagg acgtgggctt ccccgtgcgc ccccaggtgc ccctgcgccc catgacctac    3300
aaggccgcct tcgacctgag cttcttcctg aaggagaagg cggcctgga gggcctgatc    3360
cacagcaagc gccgccagga catcctggac ctgtgggtgt accacaccca gggctacttc    3420
cccgactggc agaactacac ccccggcccc ggcgtgcgct accccctgac cttcggctgg    3480
tgcttcaagc tggtgcccgt ggacccccgc gaggtggagg aggccaacaa gggcgagaac    3540
aactgcctgc tgcaccccat gagccagcac ggcatggagg acgccgaccg cgaggtgctg    3600
cgctgggtgt cgacagcag cctggcccgc cgccacctgg cccgcgagaa gcaccccgag    3660
tactacaagg actgagaatt ctctaga                                        3687
```

<210> SEQ ID NO 30
<211> LENGTH: 1228
<212> TYPE: PRT
<213> ORGANISM: Human immunodeficiency virus type 1

<400> SEQUENCE: 30

```
Lys Leu Ala Thr Met Ala Ala Arg Ala Ser Ile Leu Arg Gly Glu Lys
1               5                   10                  15

Leu Asp Lys Trp Glu Lys Ile Arg Leu Arg Pro Gly Gly Lys Lys His
            20                  25                  30

Tyr Met Leu Lys His Ile Val Trp Ala Ser Arg Glu Leu Glu Arg Phe
        35                  40                  45

Ala Leu Asn Pro Gly Leu Leu Glu Thr Ser Glu Gly Cys Lys Gln Ile
    50                  55                  60

Met Lys Gln Leu Gln Pro Ala Leu Gln Thr Gly Thr Glu Glu Leu Lys
65                  70                  75                  80

Ser Leu Tyr Asn Thr Val Ala Thr Leu Tyr Cys Val His Glu Lys Ile
                85                  90                  95
```

-continued

```
Glu Val Arg Asp Thr Lys Glu Ala Leu Asp Lys Ile Glu Glu Gln
            100                 105                 110

Asn Lys Cys Gln Gln Lys Thr Gln Gln Ala Lys Ala Ala Asp Gly Lys
        115                 120                 125

Val Ser Gln Asn Tyr Pro Ile Val Gln Asn Leu Gln Gly Gln Met Val
    130                 135                 140

His Gln Ala Ile Ser Pro Arg Thr Leu Asn Ala Trp Val Lys Val Ile
145                 150                 155                 160

Glu Glu Lys Ala Phe Ser Pro Glu Val Ile Pro Met Phe Thr Ala Leu
                165                 170                 175

Ser Glu Gly Ala Thr Pro Gln Asp Leu Asn Thr Met Leu Asn Thr Val
            180                 185                 190

Gly Gly His Gln Ala Ala Met Gln Met Leu Lys Asp Thr Ile Asn Glu
        195                 200                 205

Glu Ala Ala Glu Trp Asp Arg Leu His Pro Val His Ala Gly Pro Ile
    210                 215                 220

Ala Pro Gly Gln Met Arg Glu Pro Arg Gly Ser Asp Ile Ala Gly Thr
225                 230                 235                 240

Thr Ser Thr Leu Gln Glu Gln Ile Ala Trp Met Thr Ser Asn Pro Pro
                245                 250                 255

Ile Pro Val Gly Asp Ile Tyr Lys Arg Trp Ile Ile Leu Gly Leu Asn
            260                 265                 270

Lys Ile Val Arg Met Tyr Ser Pro Val Ser Ile Leu Asp Ile Arg Gln
        275                 280                 285

Gly Pro Lys Glu Pro Phe Arg Asp Tyr Val Asp Arg Phe Phe Lys Thr
    290                 295                 300

Leu Arg Ala Glu Gln Ala Thr Gln Glu Val Lys Asn Trp Met Thr Asp
305                 310                 315                 320

Thr Leu Leu Val Gln Asn Ala Asn Pro Asp Cys Lys Thr Ile Leu Arg
                325                 330                 335

Ala Leu Gly Pro Gly Ala Thr Leu Glu Glu Met Met Thr Ala Cys Gln
            340                 345                 350

Gly Val Gly Gly Pro Gly His Lys Ala Arg Val Leu Ala Glu Ala Met
        355                 360                 365

Ser Gln Thr Asn Ser Gly Asn Ile Met Met Gln Arg Ser Asn Phe Lys
    370                 375                 380

Gly Pro Arg Arg Ile Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Glu Phe
        435                 440                 445

Cys Gly Lys Lys Ala Ile Gly Thr Val Leu Val Gly Pro Thr Pro Val
    450                 455                 460

Asn Ile Ile Gly Arg Asn Met Leu Thr Gln Leu Gly Cys Thr Leu Asn
465                 470                 475                 480

Phe Pro Ile Ser Pro Ile Glu Thr Val Pro Val Lys Leu Lys Pro Gly
                485                 490                 495

Met Asp Gly Pro Lys Val Lys Gln Trp Pro Leu Thr Glu Val Lys Ile
            500                 505                 510
```

-continued

```
Lys Ala Leu Thr Ala Ile Cys Glu Glu Met Glu Lys Glu Gly Lys Ile
            515                 520                 525
Thr Lys Ile Gly Pro Glu Asn Pro Tyr Asn Thr Pro Ile Phe Ala Ile
        530                 535                 540
Lys Lys Glu Asp Ser Thr Lys Trp Arg Lys Leu Val Asp Phe Arg Glu
545                 550                 555                 560
Leu Asn Lys Arg Thr Gln Asp Phe Trp Glu Val Gln Leu Gly Ile Pro
                565                 570                 575
His Pro Ala Gly Leu Lys Lys Lys Ser Val Thr Val Leu Asp Val
            580                 585                 590
Gly Asp Ala Tyr Phe Ser Val Pro Leu Asp Glu Gly Phe Arg Lys Tyr
            595                 600                 605
Thr Ala Phe Thr Ile Pro Ser Ile Asn Asn Glu Thr Pro Gly Ile Arg
            610                 615                 620
Tyr Gln Tyr Asn Val Leu Pro Gln Gly Trp Lys Gly Ser Pro Ala Ile
625                 630                 635                 640
Phe Gln Ala Ser Met Thr Lys Ile Leu Glu Pro Phe Arg Ala Lys Asn
                645                 650                 655
Pro Glu Ile Val Ile Tyr Gln Tyr Met Ala Ala Leu Tyr Val Gly Ser
            660                 665                 670
Asp Leu Glu Ile Gly Gln His Arg Ala Lys Ile Glu Glu Leu Arg Glu
        675                 680                 685
His Leu Leu Lys Trp Gly Phe Thr Thr Pro Asp Lys Lys His Gln Lys
        690                 695                 700
Glu Pro Pro Phe Leu Trp Met Gly Tyr Glu Leu His Pro Asp Lys Trp
705                 710                 715                 720
Thr Val Gln Pro Ile Gln Leu Pro Glu Lys Asp Ser Trp Thr Val Asn
                725                 730                 735
Asp Ile Gln Lys Leu Val Gly Lys Leu Asn Trp Thr Ser Gln Ile Tyr
            740                 745                 750
Pro Gly Ile Lys Val Arg Gln Leu Cys Lys Leu Leu Arg Gly Thr Lys
        755                 760                 765
Ala Leu Thr Asp Ile Val Pro Leu Thr Glu Glu Ala Glu Leu Glu Leu
        770                 775                 780
Ala Glu Asn Arg Glu Ile Leu Lys Glu Pro Val His Gly Val Tyr Tyr
785                 790                 795                 800
Asp Pro Ser Lys Asp Leu Ile Ala Glu Ile Gln Lys Gln Gly Asp Asp
                805                 810                 815
Gln Trp Thr Tyr Gln Ile Tyr Gln Glu Pro Phe Lys Asn Leu Lys Thr
            820                 825                 830
Gly Lys Tyr Ala Lys Arg Arg Thr Thr His Thr Asn Asp Val Lys Gln
        835                 840                 845
Leu Thr Glu Ala Val Gln Lys Ile Ser Leu Glu Ser Ile Val Thr Trp
        850                 855                 860
Gly Lys Thr Pro Lys Phe Arg Leu Pro Ile Gln Lys Glu Thr Trp Glu
865                 870                 875                 880
Ile Trp Trp Thr Asp Tyr Trp Gln Ala Thr Trp Ile Pro Glu Trp Glu
                885                 890                 895
Phe Val Asn Ser Gly Arg Lys Leu Ala Thr Met Val Gly Ile Ser Tyr
            900                 905                 910
Gly Arg Lys Lys Arg Arg Gln Arg Arg Ser Thr Pro Pro Ser Ser Glu
        915                 920                 925
```

```
Asp His Gln Asn Pro Ile Ser Lys Gln Pro Leu Pro Gln Thr Arg Gly
        930                 935                 940

Asp Pro Thr Gly Ser Glu Ser Lys Lys Val Glu Ser Lys Thr
945                 950                 955                 960

Lys Thr Asp Pro Phe Asp Cys Lys Tyr Cys Ser Tyr His Cys Leu Val
                965                 970                 975

Cys Phe Gln Thr Lys Gly Leu Gly Ile Ser Tyr Gly Arg Lys Lys Arg
            980                 985                 990

Met Glu Pro Ile Asp Pro Asn Leu Glu Pro Trp Asn His Pro Gly Ser
        995                 1000                1005

Gln Pro Asn Thr Pro Cys Asn Lys Cys Tyr Cys Lys Tyr Cys Ser
    1010                1015                1020

Tyr His Cys Leu Val Val Gly Trp Pro Ala Val Arg Glu Arg Ile
    1025                1030                1035

Arg Arg Thr Glu Pro Ala Ala Glu Gly Val Gly Pro Ala Ser Gln
    1040                1045                1050

Asp Leu Asp Lys His Gly Ala Leu Thr Ser Ser Asn Thr Ala His
    1055                1060                1065

Asn Asn Pro Asp Cys Ala Trp Leu Gln Ala Gln Glu Glu Glu
    1070                1075                1080

Asp Val Gly Phe Pro Val Arg Pro Gln Val Pro Leu Arg Pro Met
    1085                1090                1095

Thr Tyr Lys Ala Ala Phe Asp Leu Ser Phe Phe Leu Lys Glu Lys
    1100                1105                1110

Gly Gly Leu Glu Gly Leu Ile His Ser Lys Arg Arg Gln Asp Ile
    1115                1120                1125

Leu Asp Leu Trp Val Tyr His Thr Gln Gly Tyr Phe Pro Asp Trp
    1130                1135                1140

Gln Asn Tyr Thr Pro Gly Pro Gly Val Arg Tyr Pro Leu Thr Phe
    1145                1150                1155

Gly Trp Cys Phe Lys Leu Val Pro Val Asp Pro Arg Glu Val Glu
    1160                1165                1170

Glu Ala Asn Lys Gly Glu Asn Asn Cys Leu Leu His Pro Met Ser
    1175                1180                1185

Gln His Gly Met Glu Asp Ala Asp Arg Glu Val Leu Arg Trp Val
    1190                1195                1200

Phe Asp Ser Ser Leu Ala Arg Arg His Leu Ala Arg Glu Lys His
    1205                1210                1215

Pro Glu Tyr Tyr Lys Asp Glu Phe Ser Arg
    1220                1225

<210> SEQ ID NO 31
<211> LENGTH: 1326
<212> TYPE: DNA
<213> ORGANISM: Human immunodeficiency virus type 1

<400> SEQUENCE: 31
atggctgctc gcgcatctat cctcagaggc gaaaagttgg ataagtggga aaaaatcaga    60
ctcaggccag gaggtaaaaa acactacatg ctgaagcata tcgtgtgggc atctagggag   120
ttggagagat ttgcactgaa ccccggactg ctggaaacct cagagggctg taagcaaatc   180
atgaaacagc tccaaccagc cttgcagacc ggaacagaag agctgaagtc cctttacaat   240
accgtggcaa ccctctattg cgtccacgag aagatcgagg tgagagacac aaaggaggcc   300
ctggacaaaa tcgaggagga gcagaataag tgccagcaga agacccagca ggcaaaggct   360
```

```
gctgacggaa aggtctctca gaactatcct atcgttcaga accttcaggg gcagatggtg    420
caccaagcaa tcagccctag aaccctgaac gcatgggtga aggtgatcga ggagaaagcc    480 tttctcccg aggttatccc catgtttacc gccctgagcg aaggcgccac tcctcaagac     540
ctgaacacta tgctgaacac agtgggagga caccaggccg ctatgcagat gttgaaggat    600
accatcaacg aggaggcagc cgaatgggac cgcctccacc ccgtgcacgc cggacctatc    660 gccccggac aaatgagaga acctcgcgga agtgatattg ccggtactac cagcaccctt     720
caagagcaga ttgcttggat gaccagcaac ccacccatcc cagtgggcga tatttacaaa    780
aggtggatta ttctggggct gaacaaaatt gtgagaatgt actcccccgt ctccatcctc    840
gacatccgcc aaggacccaa ggagcctttt agggattacg tggacagatt cttcaaaacc    900
cttagagctg agcaagccac tcaggaggtt aagaactgga tgacagatac tctgctcgtg    960
caaaacgcta accccgattg caaaaccatc ttgagagctc tcggtccagg tgccacccct   1020
gaggaaatga tgacagcatg tcaaggcgtg gaggacctg gcacaaggc cagagttctc     1080 gctgaggcca tgagccagac aaactcaggc aatatcatga tgcagaggag taactttaag   1140
ggtcccagga gaatcgtcaa gtgcttcaat tgtggcaagg agggtcacat tgccaggaac   1200
tgccgcgccc ccaggaagaa aggctgctgg aagtgtggca agagggccac ccagatgaag   1260
gattgcaccg agcgccaagc aaacttcctg ggaaagattt ggcccagtca taagggccgc   1320
cctggc                                                               1326

<210> SEQ ID NO 32
<211> LENGTH: 442
<212> TYPE: PRT
<213> ORGANISM: Human immunodeficiency virus type 1

<400> SEQUENCE: 32

Met Ala Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190
```

```
Ala Ala Met Gln Met Leu Lys Asp Thr Ile Asn Glu Glu Ala Ala Glu
        195                 200                 205
Trp Asp Arg Leu His Pro Val His Ala Gly Pro Ile Ala Pro Gly Gln
    210                 215                 220
Met Arg Glu Pro Arg Gly Ser Asp Ile Ala Gly Thr Thr Ser Thr Leu
225                 230                 235                 240
Gln Glu Gln Ile Ala Trp Met Thr Ser Asn Pro Pro Ile Pro Val Gly
                245                 250                 255
Asp Ile Tyr Lys Arg Trp Ile Ile Leu Gly Leu Asn Lys Ile Val Arg
            260                 265                 270
Met Tyr Ser Pro Val Ser Ile Leu Asp Ile Arg Gln Gly Pro Lys Glu
        275                 280                 285
Pro Phe Arg Asp Tyr Val Asp Arg Phe Phe Lys Thr Leu Arg Ala Glu
    290                 295                 300
Gln Ala Thr Gln Glu Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
            340                 345                 350
Pro Gly His Lys Ala Arg Val Leu Ala Glu Ala Met Ser Gln Thr Asn
        355                 360                 365
Ser Gly Asn Ile Met Met Gln Arg Ser Asn Phe Lys Gly Pro Arg Arg
    370                 375                 380
Ile Val Lys Cys Phe Asn Cys Gly Lys Glu Gly His Ile Ala Arg Asn
385                 390                 395                 400
Cys Arg Ala Pro Arg Lys Lys Gly Cys Trp Lys Cys Gly Lys Glu Gly
                405                 410                 415
His Gln Met Lys Asp Cys Thr Glu Arg Gln Ala Asn Phe Leu Gly Lys
            420                 425                 430
Ile Trp Pro Ser His Lys Gly Arg Pro Gly
        435                 440

<210> SEQ ID NO 33
<211> LENGTH: 1397
<212> TYPE: DNA
<213> ORGANISM: Human immunodeficiency virus type 1

<400> SEQUENCE: 33
gggaaagatt tggcccagtc ataagggccg ccctggcgaa ttctgcggca agaaggccat      60
cggcaccgtg ctggtgggcc caccccccgt gaacatcatc ggccggaaca tgctgaccca     120
gctgggctgc accctgaact tccccatcag ccccatcgag accgtgcccg tgaagctgaa     180
gcccggcatg gacggcccca aggtgaagca gtggcccctg accgaggtga agatcaaggc     240
cctgaccgcc atctgcgagg agatggagaa ggagggcaag atcaccaaga tcggcccgga     300
gaacccctac aacaccccca tcttcgccat caagaaggag acagcacca agtggcggaa     360 gctggtggac ttccgggagc tgaacaagcg acccaggact tctgggagg tgcagctggg     420 catccccac cccgccggcc tgaagaagaa gagcgtg accgtgctgg acgtgggcga     480
cgcctacttc agcgtgcccc tggacgaggg cttccggaag tacaccgcct tcaccatccc     540
cagcatcaac aacgagaccc ccggcatccg gtaccagtac aacgtgctgc cccagggctg     600
gaagggcagc cccgccatct tccaggccag catgaccaag atcctggagc ccttccgggc     660
caagaacccc gagatcgtga tctaccagta catggccgcc ctgtacgtgg gcagcgacct     720
```

-continued

```
ggagatcggc cagcaccggg ccaagatcga ggagctgcgg gagcacctgc tgaagtgggg    780
cttcaccacc cccgacaaga agcaccagaa ggagccccc ttcctgtgga tgggctacga    840
gctgcacccc gacaagtgga ccgtgcagcc catccagctg cccgagaagg acagctggac    900
cgtgaacgac atccagaagc tggtgggcaa gctgaactgg accagccaga tctaccccgg    960
catcaaggtg cggcagctgt gcaagctgct gcggggcacc aaggccctga ccgacatcgt   1020
gcccctgacc gaggaggccg agctggagct ggccgagaac cggagatccc tgaaggagcc   1080
cgtgcacggc gtgtactacg accccagcaa ggacctgatc gccgagatcc agaagcaggg   1140
cgacgaccag tggaccctac cagatctacca ggagcccttc aagaacctga aaccggcaa   1200 gtacgccaag cggcggacca cccacaccaa cgacgtgaag cagctgaccg aggccgtgca   1260
gaagatcagc ctggagagca tcgtgacctg gggcaagacc cccaagttcc ggctgcccat   1320
ccagaaggag acctgggaga tctggtggac cgactactgg caggccacct ggatccccga   1380
gtgggagttc gtgaaca                                                  1397
```

<210> SEQ ID NO 34
<211> LENGTH: 451
<212> TYPE: PRT
<213> ORGANISM: Human immunodeficiency virus type 1

<400> SEQUENCE: 34

```
Cys Gly Lys Lys Ala Ile Gly Thr Val Leu Val Gly Pro Thr Pro Val
1               5                   10                  15

Asn Ile Ile Gly Arg Asn Met Leu Thr Gln Leu Gly Cys Thr Leu Asn
            20                  25                  30

Phe Pro Ile Ser Pro Ile Glu Thr Val Pro Val Lys Leu Lys Pro Gly
        35                  40                  45

Met Asp Gly Pro Lys Val Lys Gln Trp Pro Leu Thr Glu Val Lys Ile
    50                  55                  60

Lys Ala Leu Thr Ala Ile Cys Glu Glu Met Glu Lys Glu Gly Lys Ile
65                  70                  75                  80

Thr Lys Ile Gly Pro Glu Asn Pro Tyr Asn Thr Pro Ile Phe Ala Ile
                85                  90                  95

Lys Lys Glu Asp Ser Thr Lys Trp Arg Lys Leu Val Asp Phe Arg Glu
            100                 105                 110

Leu Asn Lys Arg Thr Gln Asp Phe Trp Glu Val Gln Leu Gly Ile Pro
        115                 120                 125

His Pro Ala Gly Leu Lys Lys Lys Ser Val Thr Val Leu Asp Val
    130                 135                 140

Gly Asp Ala Tyr Phe Ser Val Pro Leu Asp Glu Gly Phe Arg Lys Tyr
145                 150                 155                 160

Thr Ala Phe Thr Ile Pro Ser Ile Asn Asn Glu Thr Pro Gly Ile Arg
                165                 170                 175

Tyr Gln Tyr Asn Val Leu Pro Gln Gly Trp Lys Gly Ser Pro Ala Ile
            180                 185                 190

Phe Gln Ala Ser Met Thr Lys Ile Leu Glu Pro Phe Arg Ala Lys Asn
        195                 200                 205

Pro Glu Ile Val Ile Tyr Gln Tyr Met Ala Ala Leu Tyr Val Gly Ser
    210                 215                 220

Asp Leu Glu Ile Gly Gln His Arg Ala Lys Ile Glu Glu Leu Arg Glu
225                 230                 235                 240

His Leu Leu Lys Trp Gly Phe Thr Pro Asp Lys Lys His Gln Lys
                245                 250                 255
```

```
Glu Pro Pro Phe Leu Trp Met Gly Tyr Glu Leu His Pro Asp Lys Trp
                260                 265                 270

Thr Val Gln Pro Ile Gln Leu Pro Glu Lys Asp Ser Trp Thr Val Asn
            275                 280                 285

Asp Ile Gln Lys Leu Val Gly Lys Leu Asn Trp Thr Ser Gln Ile Tyr
        290                 295                 300

Pro Gly Ile Lys Val Arg Gln Leu Cys Lys Leu Leu Arg Gly Thr Lys
305                 310                 315                 320

Ala Leu Thr Asp Ile Val Pro Leu Thr Glu Glu Ala Glu Leu Glu Leu
                325                 330                 335

Ala Glu Asn Arg Glu Ile Leu Lys Glu Pro Val His Gly Val Tyr Tyr
            340                 345                 350

Asp Pro Ser Lys Asp Leu Ile Ala Glu Ile Gln Lys Gln Gly Asp Asp
        355                 360                 365

Gln Trp Thr Tyr Gln Ile Tyr Gln Glu Pro Phe Lys Asn Leu Lys Thr
    370                 375                 380

Gly Lys Tyr Ala Lys Arg Arg Thr Thr His Thr Asn Asp Val Lys Gln
385                 390                 395                 400

Leu Thr Glu Ala Val Gln Lys Ile Ser Leu Glu Ser Ile Val Thr Trp
                405                 410                 415

Gly Lys Thr Pro Lys Phe Arg Leu Pro Ile Gln Lys Glu Thr Trp Glu
            420                 425                 430

Ile Trp Trp Thr Asp Tyr Trp Gln Ala Thr Trp Ile Pro Glu Trp Glu
        435                 440                 445

Phe Val Asn
    450

<210> SEQ ID NO 35
<211> LENGTH: 1479
<212> TYPE: DNA
<213> ORGANISM: Human immunodeficiency virus type 1

<400> SEQUENCE: 35
atgggtgcga gagcgtcaat attaagaggg gaaaaattag ataaatggga aaaaattagg      60
ttaaggccag ggggaaagaa acattatatg ttaaaacaca tagtatgggc aagcagggag    120
ctggaaagat ttgcacttaa ccctggcctt tagaaacat cagaaggatg taaacaaata    180
atgaaacagc tacaaccagc tctccagaca ggaacagagg aacttaaatc attatacaac    240
acagtagcaa ctctctattg tgtacatgaa agatagaag tacgagacac caaggaagcc    300
ttagataaga taggaggaaga acaaaacaaa tgtcagcaaa aaacgcagca ggcaaaagcg    360
gctgacggga aagtcagtca aaattatcct atagtgcaga atctccaagg gcaaatggta    420
catcaagcca tatcacctag aaccttgaat gcatgggtaa agtaataga gaaaaggct    480 tttagcccag aggtaatacc catgtttaca gcattatcag aaggagccac cccacaagat    540
ttaaacacca tgttaaatac agtgggggga catcaagcag ccatgcaaat gttaaaagat    600
actattaatg aagaggctgc agaatgggat agagtacatc cagtccatgc ggggcctatt    660
gcaccaggcc agatgagaga accaagggga agtgacatag caggaactac tagtaccctt    720
caggaacaaa tagcatggat gacaagtaac ccacctattc cagtgggaga catctataaa    780
agatggataa tcctggggtt aaataaaata gtgagaatgt atagccctgt cagcattttg    840
gacataagac aaggccaaa ggaacccttt cgagactatg tagatcggtt ctttaaaact    900
ttaagagctg aacaagctac acaagaagta aaaaattgga tgacagacac cttgttagtc    960
```

-continued

```
caaaatgcga acccagattg taagaccatt ttgagagcat taggaccagg ggctacatta    1020
gaagaaatga tgacagcatg tcaaggggtg ggaggacctg gtcacaaagc aagagtattg    1080
gctgaggcaa tgagtcaagc aaacagtgga aacataatga tgcagagaag caattttaaa    1140
ggccctagaa gaattgttaa atgttttaac tgtggcaagg aagggcacat agccagaaat    1200
tgcagagccc ctaggaaaaa aggctgttgg aaatgtggaa aggaaggaca ccaaatgaaa    1260
gactgtactg aaaggcaggc taatttttta gggaaaattt ggccttccca caaggggagg    1320
ccagggaatt tccttcagaa cagaccagag ccaacagccc caccagcaga gagcttcagg    1380
ttcgaagaga caacccccgc tccgaaacag gagccgatag aaagggaacc cttaacttcc    1440
ctcaaatcac tctttggcag cgaccccttg tctcaataa                          1479
```

<210> SEQ ID NO 36
<211> LENGTH: 492
<212> TYPE: PRT
<213> ORGANISM: Human immunodeficiency virus type 1

<400> SEQUENCE: 36

```
Met Gly Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Val His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285
```

-continued

```
Pro Phe Arg Asp Tyr Val Asp Arg Phe Phe Lys Thr Leu Arg Ala Glu
    290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365

Ser Gly Asn Ile Met Met Gln Arg Ser Asn Phe Lys Gly Pro Arg Arg
370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
        435                 440                 445

Pro Glu Pro Thr Ala Pro Pro Ala Glu Ser Phe Arg Phe Glu Glu Thr
450                 455                 460

Thr Pro Ala Pro Lys Gln Glu Pro Ile Glu Arg Glu Pro Leu Thr Ser
465                 470                 475                 480

Leu Lys Ser Leu Phe Gly Ser Asp Pro Leu Ser Gln
                485                 490

<210> SEQ ID NO 37
<211> LENGTH: 2997
<212> TYPE: DNA
<213> ORGANISM: Human immunodeficiency virus type 1

<400> SEQUENCE: 37
tttagggaaa atttggcctt cccacaaggg gaggccaggg aatttccttc agaacagacc      60
agagccaaca gccccaccag cagagagctt caggttcgaa gaaacaaccc ccgctccgaa     120
acaggagccg agaaaaggga aaccttaac ttccctcaaa tcactctttg gcagcgaccc      180
cttgtctcaa taaaatagg gggccagaca agggaggctc tcttagacac aggagcagat     240
gatacagtat tagaagacat aaatttgcca ggaaaatgga accaaaaat gataggagga     300 attggaggtt ttatcaaagt aagacagtat gatcaaatac ttatagaaat ttgtggaaaa     360
aaggctatag gtacagtatt agtagggcct acacctgtca acataattgg cagaaacatg     420
ttgactcagc ttggatgcac actaaacttt ccaatcagtc ccattgaaac tgtaccagta     480
aaactgaagc caggaatgga tggcccaaag gttaaacaat ggccgttaac agaagagaaa     540
ataaaagcat taacagcaat ttgtgaagaa atggaaaagg aaggaaaaat tacaaaaatt     600
gggcctgaaa atccatataa cactccaata tttgccataa aaaagaaaga cagcactaag     660
tggagaaaat tagtagattt cagggaactc aataaaagaa ctcaagactt ttgggaggtt     720
caattaggaa taccacaccc agcagggtta aaaagaaaa aatcagtgac agtactggat     780
gtgggagatg catatttttc agttccttta gatgaaggct tcaggaaata tactgcattc     840
accataccta gtataaacaa tgaaacacca gggattagat atcaatataa tgtgcttcca     900
caaggatgga aagggtcacc agcaatattc cagggtagca tgacaaaaat cttagagccc     960
```

-continued

```
tttagagctc aaaatccaga aatagtcatc tatcaatata tggatgactt gtatgtagga     1020
tctgacttag aaataggca acatagagca aaaatagaag agttaagaga acatctatta      1080
aagtggggat ttaccacacc agacaaaaaa catcagaaag aacccccatt tctttggatg     1140
gggtatgaac tccatcctga caaatggaca gtacagccta tacagctgcc agaaaaggat    1200
agctggactg tcaatgatat acagaagtta gtgggaaaat taaactgggc aagtcagatt    1260
tacccaggga ttaaagtaag gcaactttgt aagctcctta ggggaccaa agcactaaca     1320 gacatagtac cactaactga agaagcagaa ttagaattgg cagagaacag ggaaattcta    1380
aaagaaccag tgcatggagt atattatgac ccatcaaaag acttgatagc tgaaatacag    1440
aaacaggggg atgaccaatg gacatatcaa atttaccaag aaccattcaa aaacctgaag    1500
acaggaaagt atgcaaaaag gaggactacc cacactaatg atgtaaaaca gttaacagag    1560
gcagtgcaaa aaatatcctt ggaaagcata gtaatatggg aaagactcc taaatttaga    1620 ctacccatcc aaaaagaaac atgggaaata tggtggacag actattggca agccacatgg    1680
attcctgagt gggagtttgt taatacccct cccctagtaa aactatggta ccagctagaa    1740
aaagaaccca tagcaggagc agaaactttc tatgtagatg gagcagctaa tagggaaact    1800
aaaataggaa aagcggggta tgttactgac agaggaaggc agaaaattgt aactctaagt    1860
gaaacaacaa atcagaagac tgaattacaa gcaattcagc tagctttgca agattcagaa    1920
tcagaagtaa acataataac agactcacag tacgcattag gaatcattca agcacaacca    1980
gataggagtg aatcagagtt ggtcaatcaa ataatagaac aattaataaa aaaggaaagg    2040
gtctatctgt catgggtacc agcacacaac ggacttgcag gaaatgaaca tgtagataaa    2100
ttagtaagta ggggaatcag gaaagtgctg ttctagatg aatagataa ggctcatgaa     2160 gagcatgaaa agtatcacag caattggaga gcaatggcta gtgagtttaa tctgccaccc    2220
gtagtagcaa gagaaatagt agccagctgt gataaatgtc agctaaaagg gaagccata    2280 catggacaag tagattgtag tccggggata tggcaattag attgtacaca tttagaagga    2340
aaaatcatcc tggtagcagt ccatgtagcc agtggctaca tagaagcaga ggttatccca    2400
gcagaaacag gacaagaaac agcatactat atactaaaat tagcaggaag atggccagtc    2460
aaagtaatac atacagacaa tggcagtaat ttcaccagtg ctgcagttaa ggcagcctgt    2520
tggtgggcag gtatccaaca ggaatttggg attccctaca tccccaaag tcagggagta    2580 gtagaatcca tgaataaaga attaaagaaa atcatagggc aggtaagaga tcaagctgag    2640
caccttaaga cagcagtaca aatggcagta ttcattcaca atttaaaag aaaaggggg    2700 attggggggt acagtgcagg ggaaagaata atagacataa tagcaacaga catacaaact    2760
aaagaattac aaaaacaaat tataaaaatt caaaattttc gggtttatta cagagacagc    2820
agagatccta tttggaaagg accagccaag ctactctgga aaggtgaagg ggcagtagta    2880
atacaagaca acagtgacat aaaggtagta ccaaggagga agtaaaaaat cattagggac    2940
tatggaaaac agatggcagg tgctgattgt gtggcaggta gacaggatga agattag      2997
```

<210> SEQ ID NO 38
<211> LENGTH: 998
<212> TYPE: PRT
<213> ORGANISM: Human immunodeficiency virus type 1

<400> SEQUENCE: 38

```
Phe Arg Glu Asn Leu Ala Phe Pro Gln Gly Glu Ala Arg Glu Phe Pro
1               5                   10                  15
```

```
Ser Glu Gln Thr Arg Ala Asn Ser Pro Thr Ser Arg Glu Leu Gln Val
             20                  25                  30

Arg Arg Asn Asn Pro Arg Ser Glu Thr Gly Ala Glu Arg Lys Gly Thr
         35                  40                  45

Leu Asn Phe Pro Gln Ile Thr Leu Trp Gln Arg Pro Leu Val Ser Ile
 50                  55                  60

Lys Ile Gly Gly Gln Thr Arg Glu Ala Leu Leu Asp Thr Gly Ala Asp
 65                  70                  75                  80

Asp Thr Val Leu Glu Asp Ile Asn Leu Pro Gly Lys Trp Lys Pro Lys
                 85                  90                  95

Met Ile Gly Gly Ile Gly Gly Phe Ile Lys Val Arg Gln Tyr Asp Gln
            100                 105                 110

Ile Leu Ile Glu Ile Cys Gly Lys Lys Ala Ile Gly Thr Val Leu Val
            115                 120                 125

Gly Pro Thr Pro Val Asn Ile Ile Gly Arg Asn Met Leu Thr Gln Leu
130                 135                 140

Gly Cys Thr Leu Asn Phe Pro Ile Ser Pro Ile Glu Thr Val Pro Val
145                 150                 155                 160

Lys Leu Lys Pro Gly Met Asp Gly Pro Lys Val Lys Gln Trp Pro Leu
                165                 170                 175

Thr Glu Glu Lys Ile Lys Ala Leu Thr Ala Ile Cys Glu Glu Met Glu
            180                 185                 190

Lys Glu Gly Lys Ile Thr Lys Ile Gly Pro Glu Asn Pro Tyr Asn Thr
            195                 200                 205

Pro Ile Phe Ala Ile Lys Lys Lys Asp Ser Thr Lys Trp Arg Lys Leu
210                 215                 220

Val Asp Phe Arg Glu Leu Asn Lys Arg Thr Gln Asp Phe Trp Glu Val
225                 230                 235                 240

Gln Leu Gly Ile Pro His Pro Ala Gly Leu Lys Lys Lys Lys Ser Val
                245                 250                 255

Thr Val Leu Asp Val Gly Asp Ala Tyr Phe Ser Val Pro Leu Asp Glu
            260                 265                 270

Gly Phe Arg Lys Tyr Thr Ala Phe Thr Ile Pro Ser Ile Asn Asn Glu
            275                 280                 285

Thr Pro Gly Ile Arg Tyr Gln Tyr Asn Val Leu Pro Gln Gly Trp Lys
290                 295                 300

Gly Ser Pro Ala Ile Phe Gln Gly Ser Met Thr Lys Ile Leu Glu Pro
305                 310                 315                 320

Phe Arg Ala Gln Asn Pro Glu Ile Val Ile Tyr Gln Tyr Met Asp Asp
                325                 330                 335

Leu Tyr Val Gly Ser Asp Leu Glu Ile Gly Gln His Arg Ala Lys Ile
            340                 345                 350

Glu Glu Leu Arg Glu His Leu Leu Lys Trp Gly Phe Thr Thr Pro Asp
            355                 360                 365

Lys Lys His Gln Lys Glu Pro Pro Phe Leu Trp Met Gly Tyr Glu Leu
370                 375                 380

His Pro Asp Lys Trp Thr Val Gln Pro Ile Gln Leu Pro Glu Lys Asp
385                 390                 395                 400

Ser Trp Thr Val Asn Asp Ile Gln Lys Leu Val Gly Lys Leu Asn Trp
                405                 410                 415

Ala Ser Gln Ile Tyr Pro Gly Ile Lys Val Arg Gln Leu Cys Lys Leu
            420                 425                 430
```

```
Leu Arg Gly Thr Lys Ala Leu Thr Asp Ile Val Pro Leu Thr Glu Glu
            435                 440                 445

Ala Glu Leu Glu Leu Ala Glu Asn Arg Glu Ile Leu Lys Glu Pro Val
    450                 455                 460

His Gly Val Tyr Tyr Asp Pro Ser Lys Asp Leu Ile Ala Glu Ile Gln
465                 470                 475                 480

Lys Gln Gly Asp Asp Gln Trp Thr Tyr Gln Ile Tyr Gln Glu Pro Phe
                485                 490                 495

Lys Asn Leu Lys Thr Gly Lys Tyr Ala Lys Arg Arg Thr Thr His Thr
            500                 505                 510

Asn Asp Val Lys Gln Leu Thr Glu Ala Val Gln Lys Ile Ser Leu Glu
        515                 520                 525

Ser Ile Val Ile Trp Gly Lys Thr Pro Lys Phe Arg Leu Pro Ile Gln
    530                 535                 540

Lys Glu Thr Trp Glu Ile Trp Trp Thr Asp Tyr Trp Gln Ala Thr Trp
545                 550                 555                 560

Ile Pro Glu Trp Glu Phe Val Asn Thr Pro Leu Val Lys Leu Trp
                565                 570                 575

Tyr Gln Leu Glu Lys Glu Pro Ile Ala Gly Ala Glu Thr Phe Tyr Val
            580                 585                 590

Asp Gly Ala Ala Asn Arg Glu Thr Lys Ile Gly Lys Ala Gly Tyr Val
        595                 600                 605

Thr Asp Arg Gly Arg Gln Lys Ile Val Thr Leu Ser Glu Thr Thr Asn
    610                 615                 620

Gln Lys Thr Glu Leu Gln Ala Ile Gln Leu Ala Leu Gln Asp Ser Glu
625                 630                 635                 640

Ser Glu Val Asn Ile Ile Thr Asp Ser Gln Tyr Ala Leu Gly Ile Ile
                645                 650                 655

Gln Ala Gln Pro Asp Arg Ser Glu Ser Glu Leu Val Asn Gln Ile Ile
            660                 665                 670

Glu Gln Leu Ile Lys Lys Glu Arg Val Tyr Leu Ser Trp Val Pro Ala
        675                 680                 685

His Asn Gly Leu Ala Gly Asn Glu His Val Asp Lys Leu Val Ser Arg
    690                 695                 700

Gly Ile Arg Lys Val Leu Val Leu Asp Gly Ile Asp Lys Ala His Glu
705                 710                 715                 720

Glu His Glu Lys Tyr His Ser Asn Trp Arg Ala Met Ala Ser Glu Phe
                725                 730                 735

Asn Leu Pro Pro Val Val Ala Arg Glu Ile Val Ala Ser Cys Asp Lys
            740                 745                 750

Cys Gln Leu Lys Gly Glu Ala Ile His Gly Gln Val Asp Cys Ser Pro
        755                 760                 765

Gly Ile Trp Gln Leu Asp Cys Thr His Leu Glu Gly Lys Ile Ile Leu
    770                 775                 780

Val Ala Val His Val Ala Ser Gly Tyr Ile Glu Ala Glu Val Ile Pro
785                 790                 795                 800

Ala Glu Thr Gly Gln Glu Thr Ala Tyr Tyr Ile Leu Lys Leu Ala Gly
                805                 810                 815

Arg Trp Pro Val Lys Val Ile His Thr Asp Asn Gly Ser Asn Phe Thr
            820                 825                 830

Ser Ala Ala Val Lys Ala Ala Cys Trp Trp Ala Gly Ile Gln Gln Glu
        835                 840                 845
```

```
Phe Gly Ile Pro Tyr Asn Pro Gln Ser Gln Gly Val Val Glu Ser Met
        850             855             860
Asn Lys Glu Leu Lys Lys Ile Ile Gly Gln Val Arg Asp Gln Ala Glu
865             870             875             880
His Leu Lys Thr Ala Val Gln Met Ala Val Phe Ile His Asn Phe Lys
                885             890             895
Arg Lys Gly Gly Ile Gly Gly Tyr Ser Ala Gly Glu Arg Ile Ile Asp
            900             905             910
Ile Ile Ala Thr Asp Ile Gln Thr Lys Glu Leu Gln Lys Gln Ile Ile
        915             920             925
Lys Ile Gln Asn Phe Arg Val Tyr Tyr Arg Asp Ser Arg Asp Pro Ile
    930             935             940
Trp Lys Gly Pro Ala Lys Leu Leu Trp Lys Gly Glu Gly Ala Val Val
945             950             955             960
Ile Gln Asp Asn Ser Asp Ile Lys Val Val Pro Arg Arg Lys Val Lys
            965             970             975
Ile Ile Arg Asp Tyr Gly Lys Gln Met Ala Gly Ala Asp Cys Val Ala
            980             985             990
Gly Arg Gln Asp Glu Asp
        995
```

HIV-1 SUBTYPE ISOLATE REGULATORY/ACCESSORY GENES, AND MODIFICATIONS AND DERIVATIVES THEREOF

CROSS REFERENCE TO RELATED APPLICATIONS

This application is the U.S. National Phase of PCT/IB02/04550 filed on 31 Oct. 2002 which claims priority to South African Patent Application No. 2001/8978 filed on 31 Oct. 2001, the contents of which are incorporated by reference herein.

BACKGROUND TO THE INVENTION

THIS invention relates to a process for the selection of HIV-1 subtype (clade) C isolate regulatory/accessory genes, selected HIV-1 subtype C isolate regulatory/accessory genes and modifications and derivatives thereof for use in prophylactic and therapeutic vaccines to produce proteins and polypeptides for the purpose of eliciting protection against HIV infection or disease.

The disease acquired immunodeficiency syndrome (AIDS) is caused by human immunodeficiency virus (HIV). Over 34 million people worldwide are thought to be living with HIV/AIDS, with over 95% of infected people living in developing countries (UNAIDS, 1999). It is estimated that 24.5 million infected people reside in sub-Saharan Africa and that South Africa currently has one of the world's fastest growing HIV-1 epidemics. At the end of 2000, over 24% of pregnant women attending government antenatal clinics in South Africa were HIV positive (Department of Health, 2001). A preventative vaccine is considered to be the only feasible way to control this epidemic in the long term.

HIV shows remarkable genetic diversity that has confounded the development of a vaccine. The molecular basis of variation resides in the viral enzyme reverse transcriptase which not only introduces an error every round of replication, but also promotes recombination between viral RNAs. Based on phylogenetic analysis of sequences, HIV has been classified into a number of groups: the M (major group) which comprises subtypes A to H and K, the O (outlier group) and the N (non-M, non-O group). Recently recombinant viruses have been more frequently identified and there are a number which have spread significantly and established epidemics (circulating recombinant forms or CRF) such as subtype A/G recombinant in West Africa, and CRF A/E recombinant in Thailand (Robertson et at., 2000).

Subtype C predominates in the Southern African region which includes Botswana, Zimbabwe, Zambia, Malawi, Mozambique and South Africa. In addition, increasing numbers of subtype C infections are being detected in the Southern region of Tanzania. This subtype also predominates in Ethiopia and India and is becoming more important in China.

A possible further obstacle to vaccine development is that the biological properties of HIV change as disease progresses. HIV requires two receptors to infect cells, the CD4 and co-receptors of which CCR5 and CXCR4 are the major co-receptors used by HIV-1 strains. The most commonly transmitted phenotype is non-syncytium inducing (NSI), macrophage-tropic viruses that utilise the CCR5 co-receptor for entry (R5 viruses). Langerhans cells in the mucosa are thought to selectively pick up R5 variants at the portal of entry and transport them to the lymph nodes where they undergo replication and expansion. As the infection progresses, viruses evolve that have increased replicative capacity and the ability to grow in T cell lines. These syncytium-inducing (SI) T-tropic viruses use CXCR4 in conjunction with or in preference to CCR5, and in some cases also use other minor co-receptors (Connor et al., 1997, Richman & Bozzette, 1994). However HIV-1 subtype C viruses appear to be unusual in that they do not readily undergo this phenotypic switch, as R5 viruses are also predominant in patients with advanced AIDS (Bjorndal et al., 1999, Peeters et al., 1999, Tscherning et al., 1998, Scarlatti et al., 1997).

An HIV vaccine aims to elicit both a CD8+ cytotoxic T lymphocyte (CTL) immune response as well as a neutralizing antibody response. Many current vaccine approaches have primarily focused on inducing a CTL response. It is thought that the CTL response may be more important as it is associated with the initial control of viral replication after infection, as well as control of replication during disease, and is inversely correlated with disease progression (Koup et al., 1994, Ogg et al., 1999 Schmitz et al., 1999). The importance of CTL in protecting individuals from infection is demonstrated by their presence in highly exposed seronegative individuals, for example certain sex-workers in Kenya (Rowland-Jones et al.,1998).

Knowledge of genetic diversity is highly relevant to the design of vaccines aiming at eliciting a cytotoxic T-lymphocyte (CTL) response. There are many CTL epitopes in common between viruses (HIV Molecular Immunology Database, 1998). In addition, several studies have now shown that there is a cross-reactive CTL response: individuals vaccinated with a subtype B-based vaccine could lyse autologous targets infected with a diverse group of isolates (Ferrari et al., 1997); and CTLs from non-B infected individuals could lyse subtype B-primed targets (Betts et al. 1997; Durali et al, 1998). A comparison of CTL epitopes in the HIV-1 sequence database indicated that there is a greater conservation of cytotoxic T epitopes within a subtype compared to between subtypes and that there will be a greater chance of a CTL response if the challenge virus is the same subtype as the vaccine strain.

It is thought that the regulatory genes of HIV are extremely important in eliciting an Immune response. Tat, Rev and Nef are all expressed early in the infectious cycle and would thus provide targets for cytotoxic T lymphocytes (CTLs) early in infection, possibly allowing virus infected cells to be destroyed before the virus can spread (Klotman et. al., 1991; Addo et. al., 2001). In addition, there is promising data showing that the Tat protein elicits an effective immune response in HIV-infected, asymptomatic people (Calarota et al., 1999; Calarota et. al., 2001). It has recently been reported that the Tat protein is one of the first to undergo escape from CTL in infected macaques (Allen et. al., 2000). This indicates that there is immune pressure on tat and that there is an early response to the Tat protein.

Viral strains used in the design of a vaccine need to be shown by genotypic analysis to be representative of the circulating strains and not an unusual or outlier strain. In addition, it is important that a vaccine strain also has the phenotype of a recently transmitted virus, which is NSI and uses the CCR5 co-receptor.

DEFINITIONS

In the specification which follows, certain terms are intended to have the following meanings:

"wild-type" means the naturally occurring HIV codon bias of the virus isolate;

"codon optimised" means the resynthesis of the gene using a human codon bias instead of the HIV codon bias;

"truncated" means having the first ten amino acids removed from the Nef protein to inactivate function whilst maintaining immunogenicity;

"shuffled" means the rearrangement of the Tat protein in order to inactivate function whilst maintaining immunogenicity.

SUMMARY OF THE INVENTION

According to a first aspect of the invention a molecule is provided, the molecule having:
 (i) the nucleotide sequence as set out in FIG. 1 (SEQ I.D. No. 1);
 (ii) an RNA sequence corresponding to the nucleotide sequence set out in FIG. 1 (SEQ I.D. No. 1);
 (iii) a sequence which is at least 97% DNA similar to the nucleotide sequence set out in FIG. 1 (SEQ I.D. No. 1) or an RNA sequence corresponding to it, and which displays substantially similar immunogenicity;
 (iv) a sequence which is homologous to the nucleotide sequence set out in Sequence I.D. No. 1 or an RNA sequence corresponding to it; or
 (v) a sequence which is a modification or derivative of the sequence of any one of (i) to (iv).

The modified sequence is preferably that set out in either one of FIGS. 9 and 10, which are consensus sequences of Du422 and Du151 (SEQ I.D. Nos. 9 and 10).

According to another aspect of the invention a molecule is provided, the molecule having:
 (i) the nucleotide sequence set out in FIG. 3 (SEQ I.D. No. 3);
 (ii) an RNA sequence corresponding to the nucleotide sequence set out in FIG. 3 (SEQ I.D. No. 3);
 (iii) a sequence which is at least 97% DNA similar to the nucleotide sequence set out in FIG. 3 (SEQ I.D. No. 3) or an RNA sequence corresponding to it, and which displays substantially similar immunogenicity;
 (iv) a sequence which is homologous to the nucleotide sequence set out in FIG. 3 (SEQ I.D. No. 3) or an RNA sequence corresponding to it; or
 (v) a sequence which is a modification or derivative of the sequence of any one of (i) to (iv).

The modified sequence is preferably that set out in either one of FIGS. 9 and 10, which are consensus sequences of Du422 and Du151 (SEQ I.D. No. 9 and No. 10).

According to another aspect of the invention a molecule is provided, the molecule having:
 (i) the nucleotide sequence set out in FIG. 5 (SEQ I.D. No. 5);
 (ii) an RNA sequence corresponding to the nucleotide sequence set out in FIG. 5 (SEQ I.D. No. 5);
 (iii) a sequence which is at least 98% DNA similar to the nucleotide sequence set out in FIG. 5 (SEQ I.D. No. 5) or an RNA sequence corresponding to it, and which displays substantially similar immunogenicity;
 (iv) a sequence which is homologous to the nucleotide sequence set out in FIG. 5 (SEQ I.D. No. 5) or an RNA sequence corresponding to it; or
 (v) a sequence which is a modification or derivative of the sequence of any one of (i) to (iv).

The modified sequence is preferably that set out in either one of FIGS. 12 and 13 (SEQ I.D. Nos. 12 and 13).

According to another aspect of the invention a molecule is provided, the molecule having:
 (i) the nucleotide sequence set out in FIG. 7 (SEQ I.D. No. 7);
 (ii) an RNA sequence corresponding to the nucleotide sequence set out in FIG. 7 (SEQ I.D. No. 7);
 (iii) a sequence which is at least 96% DNA similar to the nucleotide sequence set out in FIG. 7 (SEQ I.D. No. 7) or an RNA sequence corresponding to it, and which displays substantially similar immunogenicity;
 (iv) a sequence which is homologous to the nucleotide sequence set out in FIG. 7 (SEQ I.D. No. 7) or an RNA sequence corresponding to it; or
 (v) a sequence which is a modification or derivative of the sequence of any one of (i) to (iv).

The modified sequence preferably has similar or the same modifications as those set out in either one of FIGS. 12 and 13 (SEQ I.D. Nos. 12 and 13) for the nef gene of the isolate Du151.

According to another aspect of the invention a molecule is provided, the molecule having:
 (i) the nucleotide sequence set out in FIG. 15 (SEQ I.D. No. 15);
 (ii) an RNA sequence corresponding to the nucleotide sequence set out in FIG. 15 (SEQ I.D. No. 15);
 (iii) a sequence which is at least 90% or greater DNA similar to the nucleotide sequence set out in FIG. 15 (SEQ I.D. No. 15) or an RNA sequence corresponding to it, and which displays substantially similar immunogenicity;
 (iv) a sequence which is homologous to the nucleotide sequence set out in FIG. 15 (SEQ I.D. No. 15) or an RNA sequence corresponding to it; or
 (v) a sequence which is a modification or derivative of the sequence of any one of (i) to (iv).

According to another aspect of the invention a molecule is provided, the molecule having:
 (i) the nucleotide sequence set out in FIG. 17 (SEQ I.D. No. 17);
 (ii) an RNA sequence corresponding to the nucleotide sequence set out in FIG. 17 (SEQ I.D. No. 17);
 (iii) a sequence which is at least 90% DNA similar to the nucleotide sequence set out in FIG. 17 (Sequence I.D. No. 17) or an RNA sequence corresponding to it, and which displays substantially similar immunogenicity;
 (iv) a sequence which is homologous to the nucleotide sequence set out in FIG. 17 (SEQ I.D. No. 17) or an RNA sequence corresponding to it; or
 (v) a sequence which is a modification or derivative of the sequence of any one of (i) to (iv).

According to another aspect of the invention a polypeptide is provided, the polypeptide having:
 (i) the amino acid sequence set out in FIG. 2 (SEQ I.D. No. 2);
 (ii) a sequence which is at least 95% similar to the sequence of FIG. 2 and which has substantially similar immunogenicity; or
 (iii) a sequence which is a modification or derivative of the amino acid sequence set out in FIG. 2 (SEQ I.D. No. 2).

The modified sequence is preferably that set out in FIG. 11, which is a consensus sequence of Du422 and Du151 (SEQ I.D. No. 11).

According to another aspect of the invention a polypeptide is provided, the polypeptide having:
 (i) the amino acid sequence set out in FIG. 4 (SEQ I.D. No. 4);
 (ii) a sequence which is at least 95% similar to the sequence of FIG. 4 and which has substantially similar immunogenicity; or
 (iii) a sequence which is a modification or derivative of the amino acid sequence set out in FIG. 4 (SEQ I.D. No. 4).

The modified sequence is preferably that set out in FIG. 11 which is a consensus sequence of Du422 and Du151 (SEQ I.D. No. 11).

According to another aspect of the invention a polypeptide is provided, the polypeptide having:
   (i) the amino acid sequence set out in FIG. 6 (SEQ I.D. No. 6);
   (ii) a sequence which is at least 92% similar to the sequence of FIG. 6 and which has substantially similar immunogenicity; or
   (iii) a sequence which is a modification or derivative of the amino acid sequence set out in FIG. 6 (SEQ I.D. No. 6).

The modified sequence is preferably that set out in FIG. 14 (SEQ I.D. No. 14).

According to another aspect of the invention a polypeptide is provided, the polypeptide having:
   (i) the amino acid sequence set out in FIG. 8 (SEQ I.D. No. 8);
   (ii) a sequence which is at least 95% similar to the sequence of FIG. 8 and which has substantially similar immunogenicity; or
   (iii) a sequence which is a modification or derivative of the amino acid sequence set out in FIG. 8 (SEQ I.D. No. 8).

The modified sequence preferably has similar or the same modifications as those set out in FIG. 14 (SEQ I.D. No. 14) for the amino acid sequence of the nef gene of the isolate Du151.

According to another aspect of the invention a polypeptide is provided, the polypeptide having:
   (i) the amino acid sequence set out in FIG. 16 (SEQ I.D. No. 16);
   (ii) a sequence which is at least 90% similar to the sequence of FIG. 16 and which has substantially similar immunogenicity; or
   (iii) a sequence which is a modification or derivative of the amino acid sequence set out in FIG. 16 (SEQ I.D. No. 16).

According to another aspect of the invention a consensus amino acid sequence for the tat gene of HIV-1 subtype C is the following:

MEPVDPNLEPWNHPGSQPKTACNKCYCKHCSYH-CLVCFQTKGLVCFQTKGLGISYGRKKRRQRRSAP-P$^{60}$SSEDHQNLISKQPLPQTRGDPTGSEESKKKVESK-TETDPFD$^{101}$ (SEQ ID NO: 18)

According to another aspect of the invention a consensus amino acid sequence for the partial nef gene of HIV-1 subtype C is the following:

MGGKWSKSSIVGWPAVRERIRRTEPAAEGVGAAS-QDLDGKHGALTSSNSAHNNADCAWLQA$^{60}$QEEEEE-VGFPVRPQVPLRPMTYKGAFDLSFFLKEKGGLEGL-EGLIYSKKRQEILDLWVYHTQG$^{120}$FFPDWQNYTP-GPGVRYPLTFGWCFKLVPVDPREVEEANEGENNCLI-HPMSQHGMEDEDRE$^{180}$VLKWKVDSSLARRHMARE-LHPEYYKDC$^{207}$ (SEQ ID No: 19)

According to another aspect of the invention a consensus amino acid sequence for the partial rev gene of HIV-1 subtype C is the following:

MAGRSGDSDEALLQAVRIIKILYQSNPYPKPEGTR-QARKNRRRRWRARQRQIHSISERIL$^{60}$STCLGRPAEP-VPLQLPPIERLHIDCSESSGTSGTQQSQQTTEGVG-SP$^{107}$ (SEQ ID NO: 20)

According to a further aspect of the invention, there is provided the use of at least one of the sequences described above in the manufacture of a vaccine for use in the treatment or prevention of HIV infection. Preferably, at least two of the sequences are used in the vaccine.

According to a further aspect of the invention, there is provided a vaccine comprising at least two of the sequences described above.

According to a further aspect of the invention, there is provided a vaccine comprising at least portions of a gag gene sequence, a reverse transcriptase (pol) gene sequence; a shuffled tat gene sequence and a truncated nef gene sequence which have been ligated to form an in frame polygene designated grttnC (SEQ I.D. No: 30).

The vaccine may be for the treatment or prevention of HIV.

DESCRIPTION OF THE DRAWINGS

FIG. 1 (SEQ I.D. No 1) shows the nucleic acid sequence (cDNA) of the sequenced tat gene of the isolate Du422;

FIG. 2 (SEQ I.D. No 2) shows the amino acid sequence of the sequenced tat gene of the isolate Du422, derived from the nucleic acid sequence;

FIG. 3 (SEQ I.D. No 3) shows the nucleic acid sequence (cDNA) of the sequenced tat gene of the isolate Du151;

FIG. 4 (SEQ I.D. No 4) shows the amino acid sequence of the sequenced tat gene of the isolate Du151, derived from the nucleic acid sequence;

FIG. 5 (SEQ I.D. No 5) shows the nucleic acid sequence (cDNA) of the sequenced nef gene of the isolate Du151;

FIG. 6 (SEQ I.D. No 6) shows the amino acid sequence of the sequenced nef gene of the isolate Du151, derived from the nucleic acid sequence;

FIG. 7 (SEQ I.D. No 7) shows the nucleic acid sequence of the sequenced rev gene of the isolate Du422, derived from the nucleic acid sequence;

FIG. 8 (SEQ I.D. No 8) shows the amino acid sequence of the sequenced rev gene of the isolate Du422, derived from the nucleic acid sequence;

FIG. 9 (SEQ I.D. No 9) shows the nucleic acid sequence (DNA) of the wild-type, shuffled, sequenced tat gene of a consensus of the isolates Du422 and Du151;

FIG. 10 (SEQ I.D. No 10) shows the nucleic acid sequence (DNA) of the codon optimised, shuffled, sequenced tat gene of a consensus of the isolates Du422 and Du151 for the purposes of increased expression;

FIG. 11 (SEQ I.D. No 11) shows the amino acid sequence of the shuffled, sequenced Tat protein of a consensus of the isolates Du422 and Du151;

FIG. 12 (SEQ I.D. No 12) shows the nucleic acid sequence (DNA) of the wild-type, truncated, sequenced nef gene of the isolate Du151;

FIG. 13 (SEQ I.D. No 13) shows the nucleic acid sequence (DNA) of codon optimised, truncated, sequenced nef gene of the isolate Du151 for the purposes of increased expression;

FIG. 14 (SEQ I.D. No 14) shows the amino acid sequence of the truncated, sequenced Nef protein of the isolate Du151;

FIG. 15 (SEQ I.D. No 15) shows the nucleic acid sequence (DNA) of the wild-type polygene consisting of shuffled tat (SEQ I.D. No 9)—truncated nef (SEQ I.D. No 11) genes of the isolates Du422 and Du151;

FIG. 16 (SEQ I.D. No 16) shows the amino acid sequence of the sequenced shuffled Tat (SEQ I.D. No 10)—truncated Nef (SEQ I.D. No 12) polyprotein of the isolates Du422 and Du151; and FIG. 17 (SEQ I.D. No 17) shows the nucleic acid sequence (DNA) of the sequenced polygene consisting of shuffled tat—truncated nef genes of the isolates Du422 and Du151 modified to reflect human codon usage for the purposes of increased expression.

FIG. 22 shows how the sequences of the Tat proteins of each of a number of isolates (SEQ ID NOs: 39-56) varies from the South African consensus sequence for the tat gene which was developed according to the present invention;

FIG. 23 shows how the sequences of the Nef proteins of each of a number of isolates (SEQ ID NOs: 57-89) varies from the South African consensus sequence for the nef gene which was developed according to the present invention;

FIG. 24 shows how the sequences of the Rev proteins of each of a number of isolates (SEQ ID NOs: 90-107) varies from the South African consensus sequence for the rev gene which was developed according to the present invention;

FIG. 28 shows the percentage amino acid sequence identity of the sequenced Tat proteins of the various isolates in relation to one another, to the Du422 and Du151 Tat clones selected and to the South African consensus sequence for the Tat protein and is based on a pairwise comparison of the Tat proteins of the isolates;

FIG. 29 shows the percentage amino acid sequence identity of the sequenced Nef proteins of the various isolates in relation to one another, to the Du151 Nef clone selected and to the South African consensus sequence for the Nef protein and is based on a pairwise comparison of the Nef protein of the isolates;

FIG. 30 shows the percentage amino acid sequence identity of the sequenced Rev proteins of the various isolates in relation to one another, to the Du422 Rev clone selected and to the South African consensus sequence for the Rev protein and is based on a pairwise comparison of the Rev proteins of the isolates;

FIG. 31 shows a schematic representation of the shuffled Tat protein, including overlapping fragments for CTL epitope maintenance (SEQ ID NOs: 108-111);

FIG. 32a shows a nucleic acid sequence of GrttnC made up of gag (Du422), RT (Du151), shuffled tat (SEQ I.D. No. 10) and truncated nef (SEQ I.D. No. 13) (SEQ I.D. No. 29);

FIG. 32b shows an amino acid sequence of GrttnC, made up of gag (Du422), RT (Du151), shuffled tat and truncated nef (SEQ I.D. No. 16) (SEQ I.D. No. 30);

FIG. 34 shows the Du422 gag nucleotide sequence which forms part of grttnC (SEQ I.D. No: 31);

FIG. 35 shows the Du422 Gag amino acid sequence which forms part of grttnC (SEQ I.D. No: 32);

FIG. 36 shows the Du151 reverse transcriptase (RT) nucleotide sequence which forms part of grttnC (SEQ I.D. No: 33); and FIG. 37 shows the Du151 reverse transcriptase (RT) amino acid sequence which forms part of grttnC (SEQ I.D. No: 34).

DETAILED DESCRIPTION OF THE INVENTION

Figure 18:
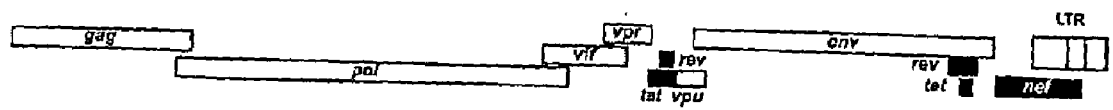
FIG. 18 shows a schematic representation of the HIV-1 genome and illustrates the location of overlapping fragments that were sequenced having been generated by reverse transcriptase followed by polymerase chain reaction, in order to generate the South African consensus sequences.

This invention relates to the selection of HIV-1 subtype C isolate regulatory and accessory genes and the use of these genes and modifications and derivatives thereof in making prophylactic and therapeutic pharmaceutical compositions and formulations, and in particular vaccines against HIV-1 subtype C. The compositions could therefore be used either prophylactically to prevent infection or therapeutically to prevent or modify disease. A number of factors must be taken into consideration in the development of an HIV vaccine and one aspect of the present invention relates to a process for the selection of suitable HIV isolates accessory and regulatory genes that may be used in the development of a vaccine.

The applicant envisages that the vaccine developed according to the above method could be used against one or more HIV subtypes as well as HIV-1 subtype C.

A process was developed to identify appropriate strains for use in developing a vaccine for HIV-1 subtype C. Viral isolates from acutely infected individuals were collected. They were sequenced in the tat, rev and nef regions and the amino acid sequences for the tat, rev and nef genes from these isolates were compared. A consensus sequence, the South African consensus sequence, was then formed by selecting the most frequently appearing amino acid at each position. The consensus sequence for each of the tat, rev and nef genes of HIV-1 subtype C also forms an aspect of the invention. Appropriate strains for vaccine development were then selected from these isolates by comparing them with the consensus sequence and characterising them phenotypically. The isolates also form an aspect of the invention.

In order to select for NSI strains which use the CCR5 co-receptor, a well established sex worker cohort was used to identify the appropriate strains. Appropriate strains were identified from acutely infected individuals by comparing them with the consensus sequence which had been formed. Viral isolates from 12 acutely infected individuals were sequenced in the tat, rev and/or nef regions and phenotypically characterised. These sequences were compared with viral isolates from 15 asymptomatic individuals from another region having more than 500 CD4 cells, as well as 11 viral isolates from AIDS patients attending a TB infectious disease hospital in Gauteng (n=9) and two children with AIDS (n=2). Other published subtype C sequences located in the Los Alamos Database were also included (http://ww.hiv-web.lan-1.gov/).

Two potential vaccine strains, designated Du422 and Du151 were selected. Du422 and Du151 were selected based on amino acid homology to the consensus sequence in all three gene regions: tat, rev and net, CCR5 tropism and ability to grow and replicate in tissue culture. The nucleotide and amino acid sequences of the three gene regions of the three isolates and modifications and derivatives thereof also form aspects of the invention.

The isolation and selection of viral strains for the design of a vaccine

The following criteria were used to select appropriate strains for inclusion into HIV-1 vaccines for Southern Africa:
that the strains be genotypically representative of circulating strains;
that the strain not be an outlier strain;
that the strain be as close as possible to the consensus amino acid sequence developed according to the invention for the tat, rev and nef genes of HIV-1 subtype C;

that the strain have an R5 phenotype, i.e. a phenotype associated with transmission for selection; and that the vaccine be able to be grown in tissue culture.

The following procedure was followed in the selection of viral strains for the design of a vaccine. A well-established sex worker cohort in Kwazulu Natal, South Africa was used to identify the appropriate strains for use in an HIV vaccine. Viral isolates from 12 acutely infected individuals were sequenced in tat, rev and nef and were also isolated and phenotypically characterised. These sequences were compared with a similar collection from asymptomatc and AIDS infected (nef region) individuals from the Gauteng region in South Africa and Cape Town region of the Western Cape as well as other published subtype C sequences.

Patients

Individuals with HIV infection were recruited from 4 regions in South Africa. Blood samples were obtained from recently infected sex workers from Kwazulu-Natal (n=12). Recent infection was defined as individuals who were previously seronegative and had became seropositive within the previous year. Samples were also collected from individuals attending out-patients clinics in Cape Town (n=2), women attending antenatal clinics in Johannesburg (n=6) and men attending a STD clinic on a gold mine outside. Johannesburg (n=7). The latter 2 groups were clinically stable and were classified as asymptomatic infections. In addition, for comparison in the nef gene, 11 isolates from AIDS patients were included from Gauteng; 9 isolates from patients attending a TB infectious disease hospital and 2 isolates from children infected with AIDS. Blood samples were collected in EDTA and used to determine the CD4 T cell count and genetic analysis of the virus. In the case of recent infections a branched chain (bDNA) assay (Chiron) to measure plasma viral load was done, and the virus was isolated. HIV-1 serostatus was determined by ELISA. The results of the CD4 T cell counts and the viral loads on the sex workers were established and information on the clinical status as at date of seroconversion, CD4, and data on the co-receptor usage is set out in Table 1 below.

Virus Isolation

HIV was isolated from peripheral blood mononuclear cells (PBMC) using standard co-culture techniques with mitogen-activated donor PBMC. $2\times10^6$ patient PBMC were co-cultured with $2\times10^6$ donor PBMC in 12 well plates with 2 ml RPMI 1640 with 20% FCS, antibiotics and 5% IL-2 (Boehringer). Cultures were replenished twice weekly with fresh medium containing IL-2 and once with $5\times10^5$/ml donor PBMC. Virus growth was monitored weekly using a commercial p24 antigen assay (Coulter). Antigen positive cultures were expanded and cultured for a further 2 weeks to obtain 40 ml of virus containing supernatant which was stored at −70° C. until use. The results of the isolation of the viruses from the commercial sex workers is also shown in Table 1 below.

Viral Phenotypes

Virus-containing supernatant was used to assess the biological phenotype of viral isolates on MT-2 and co-receptor transfected cell lines. For the MT-2 assay, 500 μl of supernatant was incubated with $5\times10^4$ MT-2 cells in PRMI plus 10% FCS and antibiotics. Cultures were monitored daily for syncitia formation over 6 days. U87.CD4 cell expressing either the CCR5 or CXCR4 co-receptor were grown in DMEM with 10% FCS, antibiotics, 500 μg/ml G418 and 1 μg/ml puromycin. GHOST cells expressing minor co-receptors were grown in DMEM with 10% FCS, 500 μg/ml G418, 1 μg/ml puromycin and 100 μg/ml hygromycin. Cell lines were passaged twice weekly by trypsination. Co-receptor assays were done in 12 well plates; $5\times10^4$ cells were plated in each well and allowed to adhere overnight. The following day 500 μl of virus containing supernatant was added and incubated overnight to allow viral attachment and infection and washed three times the following day. Cultures were monitored on days 4, 8 and 12 for syncitia formation and p24 antigen production. Cultures that showed evidence of syncitia and increasing concentrations of p24 antigen were considered positive for viral growth. The results of co-receptor usage of the viruses from the commercial sex workers are also shown in Table 1.

TABLE 1

COHORT OF ACUTE INFECTIONS FOR SELECTION OF VACCINE CANDIDATES

| Sample ID | Sero date | Sample date | Duration of infection | CD4 count | Viral load | Co-culture p24 pos | MT-2 assay | Biotype |
|---|---|---|---|---|---|---|---|---|
| Du123 | 17 Aug. 1998 | 17 Nov. 1998 | 3 mon | 841 | 19,331 | d6 (50 pg) | NSI | R5 |
| Du151 | 12 Oct. 1998 | 24 Nov. 1998 | 1.5 mon | 367 | >500,000 | d6 (>1 ng) | NSI | R5 |
| Du156 | 16 Nov. 1998 | 17 Nov. 1998 | <1 mon | 404 | 22,122 | d6 (>1 ng) | NSI | R5 |
| Du179 | 13 Aug. 1997 | 20 May 1999 | 21 mon | 394* | 1,359* | d7 (<50 pg) | SI | R5 × 4 |

TABLE 1-continued

COHORT OF ACUTE INFECTIONS FOR SELECTION OF VACCINE CANDIDATES

| Sample ID | Sero date | Sample date | Duration of infection | CD4 count | Viral load | Co-culture p24 pos | MT-2 assay | Biotype |
|---|---|---|---|---|---|---|---|---|
| Du204 | 20 May 1998 | 20 May 1999 | 1 year | 633* | 8,734* | d7 (<50 pg) | NSI | R5 |
| Du258 | 3 Jun. 1998 | 22 Jun. 1999 | 1 year | 433* | 9,114* | — | No isolate | — |
| Du281 | 24 Jul. 1998 | 17 Nov. 1998 | 4 mon | 594 | 24,689 | d6 (1 ng) | NSI | R5 |
| Du285 | 2 Oct. 1998 | — | — | 560* | 161* | — | No isolate | — |
| Du368 | 8 Apr. 1998 | 24 Nov.1998 | 7.5 mon | 670 | 13,993 | d6 (300 pg) | NSI | R5 |
| Du422 | 2 Oct. 1998 | 28 Jan. 1999 | 4 mon | 397 | 17,118* | d6 (600 pg) | NSI | R5 |
| Du457 | 17 Aug. 1998 | 17 Nov. 1998 | 3 mon | 665 | 6,658 | — | No isolate | — |
| Du467 | 26 Aug. 1998 | — | — | 671 | 19,268 | — | No isolate | — |

*date from November 1998

Sequencing

RNA was isolated from plasma and the gene fragments were amplified from RNA using reverse transcriptase to generate a cDNA followed by PCR to generate amplified DNA segments. The positions of the PCR primers are as follows, (numbering using the HIV-1 HXBr sequence): tat outer forward primer (5'GGC CGC AGA GGG AAC CAT AC3' (SEQ ID No: 21) 5584-5703 bp), or rev outer reverse primer (5'GCC CTG TCT TAT TCT TCT AGG3' (SEQ ID No: 22) 8753-8774 bp). The remaining primers used for nested PCR were as follows: the tat outer reverse primer (5'CCT CAA TAT CCC CAT CAC TCT C3' (SEQ ID No: 23) 6226-6248 bp), tat inner forward (5'TGC CAG CAT AGC AGA ATA GG3' (SEQ ID No: 24) 5785-5804 bp) and reverse (5'CTA TCA ATG CTC CTA CTC CTA ATC3' (SEQ ID No: 25) 6078-6101 bp) primers and for rev, with the rev outer forward primer (5'GAT AGT AGG AGG CTT GAT AGG3' (SEQ ID No: 26) 8285-8302 bp) and inner forward (5'GGT GTA CTC GCT ATA GTG3' (SEQ ID No: 27) 8321-8339 bp) and reverse primers (5'CCT TCA GCT ACT GCT ATT GC3' (SEQ ID No: 28) 8689-8698 bp).

The amplified DNA fragments were purified using the QIAQUICK PCR Purification Kit (Qiagen, Germany). The DNA fragments were then sequenced using the upstream PCR primers as sequencing primers. Sequencing was done using the Sanger dideoxyterminator strategy with fluorescent dyes attached to the dideoxynucleotides. The sequence determination was made by electrophoresis using an ABI 377 Sequencer. A mapped illustration of an HIV-1 proviral genome showing the tat, rev and nef genes sequenced as described above, is shown in FIG. 18.

Genotypic Characterisation

To select the vaccine isolate or isolates, a survey covering the three HIV genes tat (101 codons, 306 bases), rev (107 contiguous codons, 324 bases) and nef (207 codons, 618 bases) was done (FIG. 18). The map of FIG. 18 shows the 5' long terminal repeat, the structural and functional genes (gag, pol and env) as well as the regulatory and accessory proteins (vif, tat, rev, nef, vpr and vpu). The gag open reading frame illustrates the regions encoding p17 matrix protein and the p24 core protein and the p7 and p6 nuclearcapsid proteins. The pol open reading frame illustrates the protease (PR) p15, reverse transcriptase (RT) p66 and the Rnase H integrase p51. The env open reading frame indicates the region coding for gp120 and the region coding for gp41.

Of a total of 38 isolates, 12 were from the Durban cohort (DU), 24 were from Johannesburg (GG, RB, COT and SW) and 2 from Cape Town (CT). Of these 17 were sequenced in the tat gene, 17 in the rev gene and 32 in the nef gene. The isolates that were sequenced are shown in Table 2.

TABLE 2

LIST OF ISOLATES AND THE REGIONS GENES SEQUENCED

| Isolate | Tat sequence | Rev sequence | Nef sequence |
|---|---|---|---|
| CTSC1 | ✓ | — | — |
| CTSC2 | ✓ | ✓ | ✓ |
| Du123 | ✓ | ✓ | ✓ |
| Du151 | ✓ | ✓ | ✓ |
| Du156 | ✓ | ✓ | — |
| Du179 | ✓ | ✓ | ✓ |
| Du204 | ✓ | ✓ | — |
| Du258 | — | — | ✓ |
| Du281 | ✓ | ✓ | — |
| Du368 | ✓ | ✓ | ✓ |
| Du422 | ✓ | ✓ | ✓ |
| Du457 | — | — | ✓ |
| Du467 | — | — | ✓ |
| GG10 | ✓ | ✓ | ✓ |
| GG2 | ✓ | — | ✓ |
| GG3 | — | — | ✓ |
| GG4 | ✓ | — | ✓ |
| GG5 | — | ✓ | ✓ |
| GG6 | — | — | ✓ |
| RB12 | ✓ | ✓ | ✓ |
| RB13 | ✓ | ✓ | ✓ |
| RB15 | — | — | ✓ |
| RB18 | — | ✓ | ✓ |
| RB21 | — | ✓ | ✓ |
| RB27 | — | ✓ | — |
| RB28 | ✓ | ✓ | ✓ |
| SW10 | — | — | ✓ |
| SW7 | — | — | ✓ |
| SW15 | — | — | ✓ |
| SW5 | — | — | ✓ |
| SW20 | — | — | ✓ |
| SW9 | — | — | ✓ |
| SW2 | — | — | ✓ |
| SW8 | — | — | ✓ |
| SW23 | — | — | ✓ |
| COT2 | — | — | ✓ |
| COT6 | — | — | ✓ |

Figure 19:
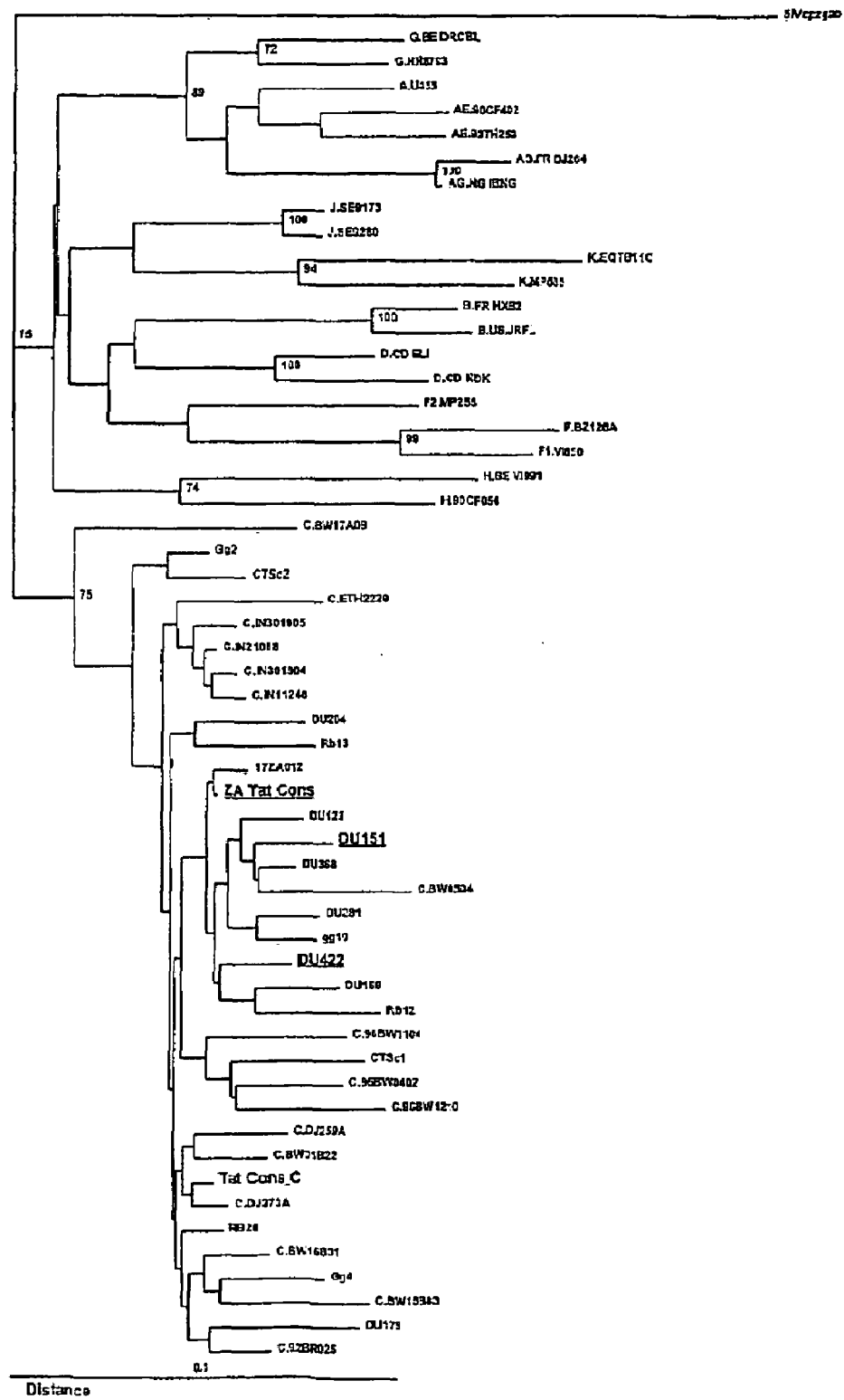
FIG. 19 shows a phylogenetic tree of nucleic acid sequences of various HIV-1 subtype C isolates based on the sequences of the tat gene of the various isolates and includes a number of consensus sequences as well as the South African consensus sequence of the present invention and selected isolates, Du422 and Du151, of the present invention.
Figure 20:
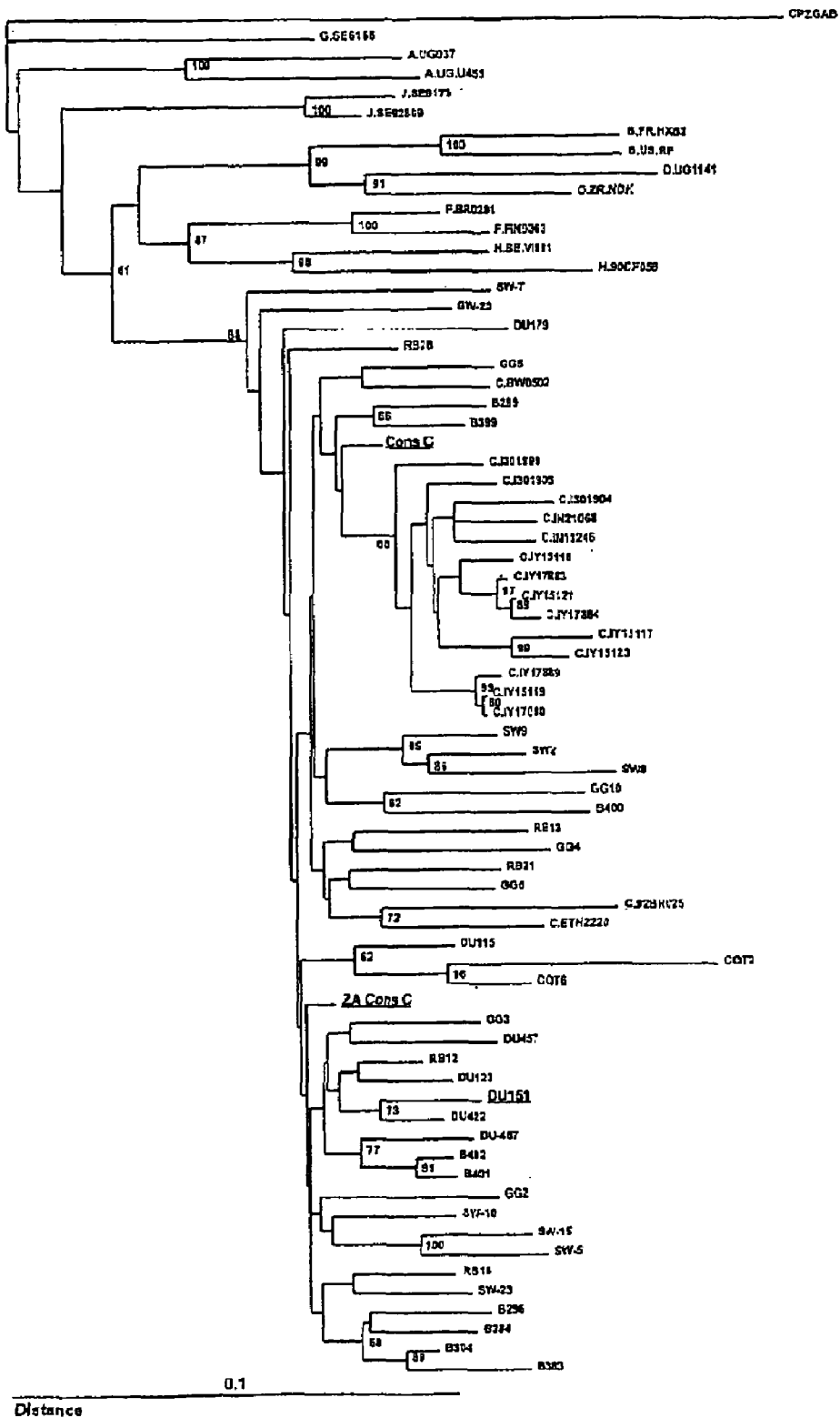
FIG. 20 shows a phylogenetic tree of nucleic acid sequences of various HIV-1 subtype C isolates based on the sequences of the nef gene of the various isolates and includes a number of consensus sequences as well as the South African consensus sequence of the present invention and a selected isolate, Du151, of the present invention.
Figure 21:
FIG. 21 shows a phylogenetic tree of nucleic acid sequences of various HIV-1 subtype C isolates based on the sequences of the rev gene of the various isolates and includes a number of consensus sequences as well as the South African consensus sequence of the present invention and a selected isolate, Du422, of the present invention.
Figure 25:
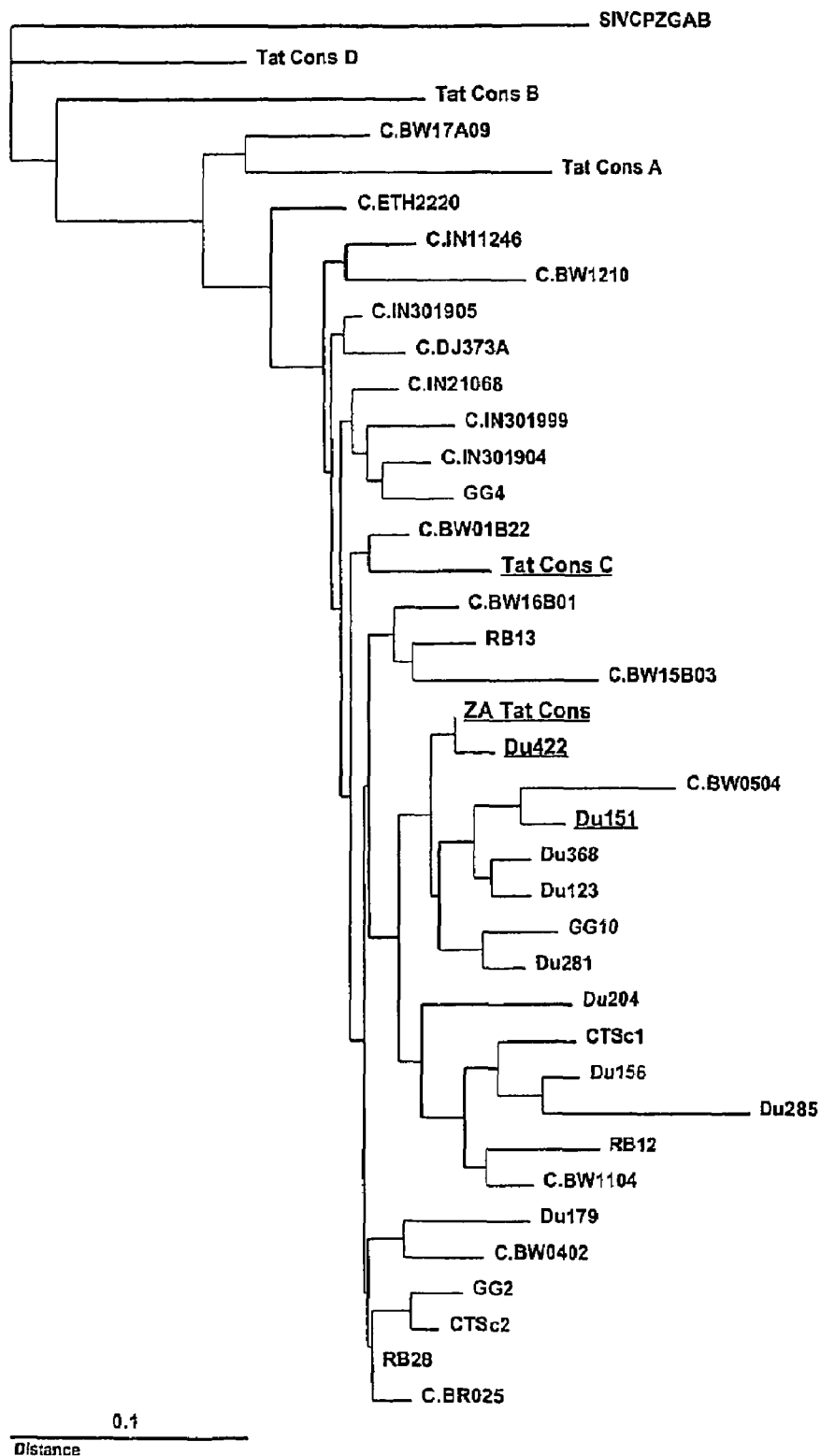
FIG. 25 shows the phylogenetic tree of amino acid sequences of various HIV-1 subtype C isolates based on the sequences of the Tat protein of the various isolates and including a number of consensus sequences, as well as the South African consensus sequence of the present invention and selected isolates, Du422 and Du151, of the present invention.
Figure 26:
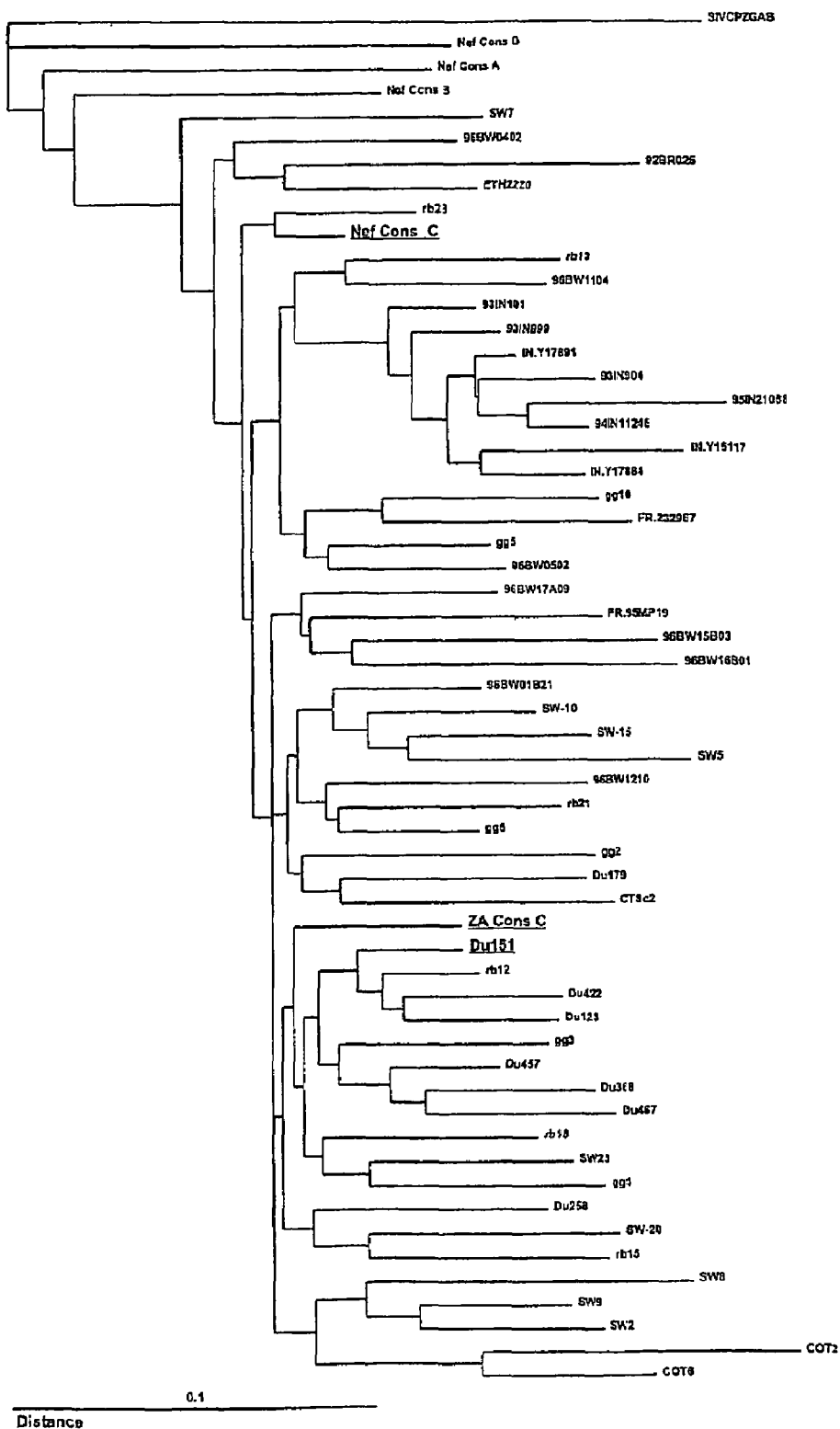
FIG. 26 shows the phylogenetic tree of amino acid sequences of various HIV-1 subtype C isolates based on the sequences of the Nef protein of the various isolates and including a number of consensus sequences, as well as the South African consensus sequence of the present invention and selected isolates, Du422 and Du151, of the present invention.
Figure 27:
FIG. 27 shows the phylogenetic tree of amino acid sequences of various HIV-1 subtype C isolates based on the sequences of the Tat protein of the various isolates and including a number of consensus sequences, as well as the South African consensus sequence of the present invention and selected isolates, Du422 and Du151, of the present invention.

The nucleic acid sequences from the Durban (Du) Johannesburg (GG, RB, SW and COT) and Cape Town (CT) cohorts were phylogenetically compared to a number of available published subtype C sequences (obtained from the Los Alamos HIV Sequence Database) including sequences from the other southern African countries and the overall subtype C consensus from the Los Alamos HIV sequence database. This comparison was done to ensure that the selected vaccine isolates were not phylogenetic outliers when compared to the Southern African sequences and the results of the comparison are shown in FIG. 19, FIG. 20 and FIG. 21. FIGS. 19 to 21 illustrate that the sequences from Southern Africa are divergent and that the Indian sequences usually form a separate distinct cluster from these African sequences. The South African sequences are not unique and, in general, are as related to each other as they are to other sequences from Southern Africa. Overall this suggests Indian sequences are unique from Southern African subtype C sequences and that we do not have a clonal epidemic in South Africa, but rather South African viruses reflect the diversity of subtype C viruses in the Southern African region Determination of a Consensus Sequence Amino acid sequences were derived from the sequences shown in Table 2 and were used to determine a South African consensus sequence. The most frequently appearing amino acid at each position was selected as the consensus amino acid at that position. In this way, the consensus sequence was determined along the linear length of each of the sequenced genes (tat, rev and nef genes). The alignments were done using the DNAMAN program (DNAMAN2 output), which generates a consensus sequence in this manner. These resulted in the consensus sequence for each gene region. The alignments of the amino acid sequences and the resulting consensus sequences are shown in FIGS. 22, 23 and 24 (SEQ ID NOs: 39-56, 57-89 and 90-107, respectively). The amino acid similarities are shown in FIGS. 25 to 27.

The final choice of which isolate or isolates to use was based on the similarity of the sequence of the tat, rev and nef genes of a particular isolate to the South African consensus sequence that had been derived as set out above, as well as the availability of an R5 isolate which had good replication kinetics as shown in Table 1.

Selection of Vaccine Isolates

Based on the considerations and methodology set out above, two strains were selected from the acute infection cohort as the vaccine strains. The first strain is Du151 for the tat and nef genes and the second strain is Du422 for the tat and rev genes. These three strains were selected for the following reasons:

1. At the time the samples were obtained, Du151 had been infected for 6 weeks and had a CD4 count of 367 cells per ul of blood and a viral load above 500,000 copies per ml of plasma. Given the high viral load, and the recorded time from infection, it is probable that the individual was still in the initial stages of viraemia prior to control of HIV replication by the immune system.
2. At the time the samples were obtained, Du422 had been infected for 4 months with a CD4 count of 397 cells per ul of blood and a viral load of 17,118 copies per ml of plasma. In contrast to Du151, this individual had already brought viral replication under control to a certain extent.

Both isolates are able to grow in cell culture and have been sequence analyzed throughout their whole genome.

Based on the analysis of the amino acid pairwise comparison between Du151 and Du422 Tat protein sequences and other isolates shown in FIG. 28, the Du151 and Du422 tat sequences were shown to be very similar to the South African consensus sequence shown in FIGS. 19 and 22. They shared 89.4% (Du151) and 91.6% (Du422) amino acid sequence identity with the consensus sequence. Both Du151 and Du422 were thus used to generate the resynthesized, shuffled Tat in both a wild-type (non-codon optimized) and humanized (codon-optimized) form. They were chosen over slightly closer related isolates to the South African consensus sequence due to their ability to grow in tissue culture and due to both isolates entire genome having been sequenced and characterized.

Figure 29:
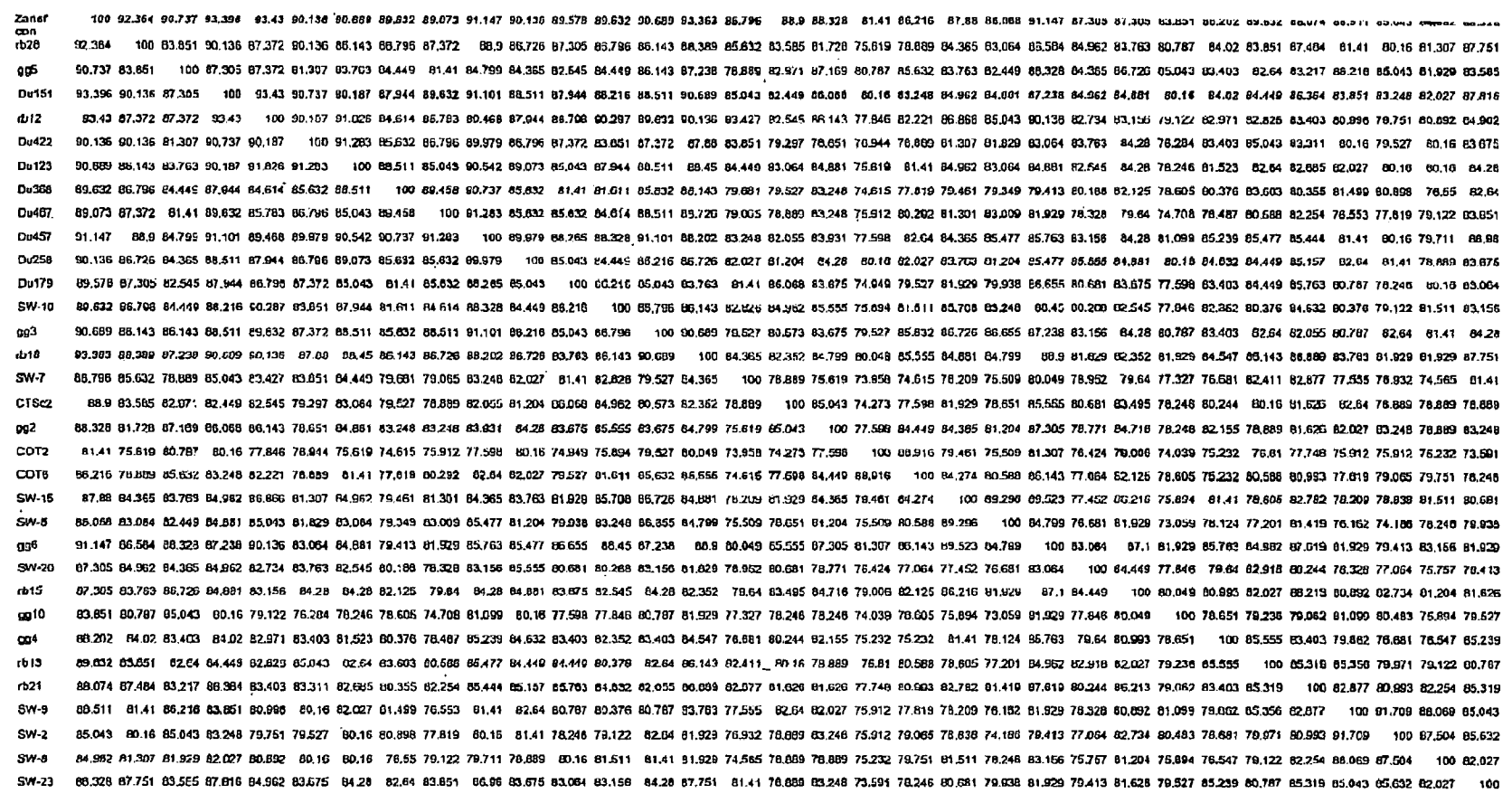

The nef gene showed the greatest sequence diversity. Based on the analysis of the Nef amino acid pairwise identity score with the SA consensus (93.4%) shown in FIG. 29, we chose the Du151 isolate as the source of the nef gene. All pairwise identity scores are above 80.2% with either the Du151 isolate sequence when compared to the other recent seroconverters, as shown in FIG. 29. Other contributing factors in this decision were that this is the same isolate that was chosen for the source of the env and pot genes and that this was an isolate with excellent growth properties in vitro.

The rev gene was the most conserved of the three. Based on the amino acid pairwise identity score with the SA consensus (95.2%), the Du422 rev gene was selected. In addition, all pairwise identity scores are above 83% with the Du422 isolate sequence when compared to the other recent seroconverters, as shown in FIG. 30. These pairwise scores make the Du422 sequence similar to the best scores in this sequence pool and combine these levels of similarity with an R5 virus with good cell culture replication kinetics.

Resynthesis of Genes

The Tat-nef polyprotein gene was produced by synthesis of oligonucleotide fragments that were ligated together to form the full gene by GeneArt (geneart GmbH, Regensburg). The codon optimised and non-codon optimised versions were synthesised and cloned into pPCR-Script (Stratagene) vector. The identity of the insert was confirmed by sequencing the insert on both strands and comparing these sequences to the original sequences. The modifications to the tat and nef gene sequences of Du422/Du151 and Du151 separately and Tat-nef polyprotein gene sequence are shown in Sequence I.D. Nos. 9-17.

The Tat protein was split into three overlapping fragments and reshuffled (as shown in FIG. 31 (SEQ ID NOs: 108-111)) to inactivate the protein, making it safer, but without losing potential CTL epitopes. The Nef protein was shortened by 10 amino acids, removing the N terminal myristylation site that allows the Nef protein to exit the cell (SEQ I.D. No.12). Apart from making the protein safer, it is hoped that this will result in a more efficient CTL response, as the protein is trapped inside the cell.

Vaccine Development

The vaccines of the invention will be formulated in a number of different ways using a variety of different vectors. They involve encapsulating RNA or transcribed DNA sequences from the viruses in a variety of different vectors. The vaccines may contain at least part of the tat and rev genes from the Du422 isolate, and at least part of the tat and nef genes from the Du151 isolate of the present invention or derivatives or modifications thereof.

Genes for use in DNA vaccines have been resynthesized to reflect human codon usage. The tat Du422 gene was also divided into three fragments with overlapping ends so that no potential CTL epitopes are lost and reshuffled to improve safety of the Tat protein. The Du151 nef gene had the first 10 amino acids deleted to remove the myristylation site for safety reasons. The reshuffled tat and shortened nef were then synthesised together in the same reading frame to constitute a Tat-Nef polyprotein. Both humanised and non-humanised versions of the Tat-nef polyprotein have been synthesised for alternative vaccines. A similarly codon optimised rev gene may be expressed by DNA vaccines.

Other vaccines will contain DNA transcribed from the RNA for the tat gene from the Du422 and Du151 isolates, DNA transcribed from the RNA for the nef gene from the Du151 isolate and DNA transcribed from the RNA for the rev gene from the Du422 isolate. These genes could also be expressed as oligomeric envelope glycoprotein complexes (Progenics, USA) as published in *J Virol* 2000 January; 74(2):

627-43 (Binley, J. L. et al.), or in the adeno associated virus (AAV) (Target Genetics), the Venezuelan equine encephalitis virus (U.S. patent application U.S. Ser. No. 60/216,995, which is incorporated herein by reference) as well as in Modified Vaccinia Ankara (MVA) (Amara et al., 2002), BCG and other vaccines being developed at the University of Cape Town.

Figure 33:
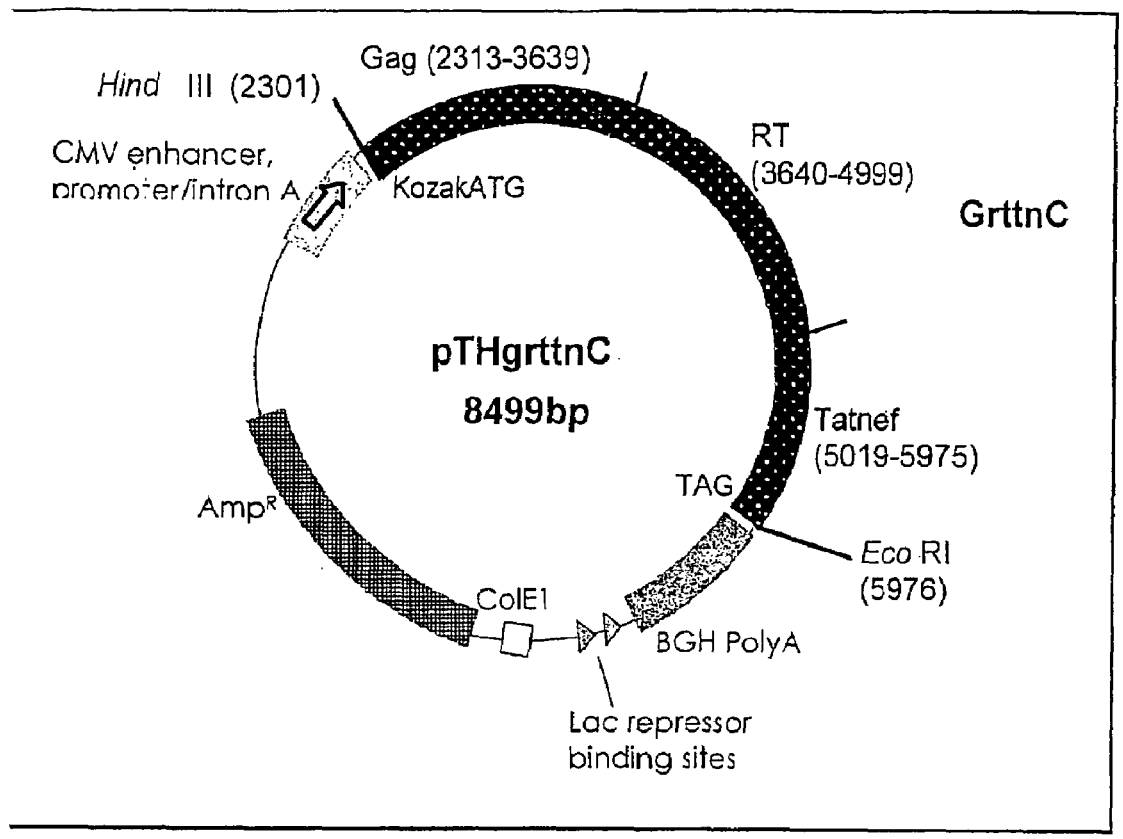
FIG. 33 shows a plasmid map of pTHgrttnC, the DNA vaccine vector expressing GrttnC for prophylactic or therapeutic use against HIV infection.

A vaccine construct containing an in frame polygene, GrttnC (FIGS. 32a and 32b; SEQ I.D. Nos. 29 and 30) including codon optimised Du422 gag (FIGS. 34 and 35; SEQ I.D. Nos. 31 and 32), Du151 RT (reverse transcriptase) (FIGS. 36 and 37; SEQ I.D. Nos. 33 and 34) (WO 02/04494, the contents of which are incorporated herein by reference) and the shuffled tat—truncated nef (SEQ I.D. No. 17) has been developed and will be incorporated into a number of vaccine candidates, including a DNA vaccine, pTHgrttnC (FIG. 33) using the pTH DNA vaccine vector (Hanke et al., 2000) and an MVA vaccine (Amara at al., 2002). The nucleotide and amino acid sequences of the gag and pol genes isolated from Du422 and Du151 are shown in SEQ I.D. Nos. 35 to 38, respectively.

The invention is not intended to be limited to the precise embodiments described.

DEPOSITS

The following material has been deposited with the European Collection of Cell Cultures, Centre for Applied Microbiology and Research, Salisbury, Wiltshire SP4 OJG, United Kingdom (ECACC).

| Material | ECACC Deposit No. | Deposit Date |
|---|---|---|
| HIV-1 Viral isolate Du151 | Accession Number 00072724 | 27 Jul. 2000 |
| HIV-1 Viral isolate Du422 | Provisional Accession Number 00072726 | 27 Jul. 2000 |
| | Provisional Accession Number 01032114 | 22 Mar. 2001 |

The deposit was made under the provisions of the Budapest Treaty on the International Recognition of the Deposit of Microorganisms for the Purpose of Patent Procedure and regulations thereunder (Budapest Treaty).

REFERENCES

UNAIDS. AIDS epidemic update. December 1999. www.unaids.org/hivaidsinfo/documents.html Addo, M. M., Altfeld, M., Rosenburg, E. S., Eldridge, R. L., Philips, M. N., Habeeb, K., Khatri, A., Brander, C., Robbins, G. K., Mazzara, G. P., Goulder, P. J. R., Walker, B. D., and the HIV Controller Study Collaboration. (2001). The HIV-1 regulatory proteins Tat and Rev are frequently targeted by cytotoxic T lymphocytes derived from HIV-1-infected individuals. *Proc Natl Acad Sci USA* 98(4): 1781-1786.

Allen, T. M., O'Connor, D. H., Jing, P., Dzuris, J. L., Mothe, B. R., Vogel, T. U., Dunphy, E., Liebl, M. E., Emerson, C., Wilson, N., Kunstman, K. J., Wang, X., Allison, D. B., Hughes, A. L., Desrosiers, R. C., Altman, J. D., Wolinsky, S. M., Sette, A. and Watkins, D. I. (2000). Tat-specific cytotoxic T lymphocytes select for SIV escape variants during resolution of primary viraemia. *Nature* 407(6802): 386-90.

Amara R R, Villinger F, Staprans S I, Altman J D, Montefiori D C, Kozyr N L, Xu Y, Wyatt L S, Earl P L, Herndon J G, McClure H M, Moss B, Robinson H L. (2002). Different patterns of immune responses but similar control of a simian-human immunodeficiency virus 89.6P mucosal challenge by modified vaccinia virus Ankara (MVA) and DNA/MVA vaccines. *J Virol* Aug.; 76(15):7625-31.

Betts, M. R., Krowka, J., Santamaria, C., Belsamo, K., Gao, F., Mulundu, G., Luo, C., N'Gandu, N., Sheppard, H., Hahn, B. H., Allen, S. and Frelinger, J. A. (1997). Cross-clade human immunodeficiency virus (HIV)-specific cytotoxic T-lymphocyte responses in HIV-infected Zambians. *J Virol,* 71(11):8908-11.

Binley J M, Sanders R W, Clas B, Schuelke N, Master A, Guo Y, Kajumo F, Anselma D J, Maddon P J, Olson W C, Moore J P, (2000). *J Virol* Jan.; 74(2):627-43

Bjorndal, A., Sonnerborg, A., Tscherning, C., Albert, J. & Fenyo, E. M. (1999). Phenotypic characteristics of human immunodeficiency virus type 1 subtype C isolates of Ethiopian AIDS patients. *AIDS Res Hum Retroviruses.* 15(7): 647-53.

Calarota, S. A., Kjerrstrom, A., Islam, K. B., and Wahren, B. (2001). Gene combination raises broad human immunodeficiency virus-specific cytotoxicity. *Hum Gene Ther* 12(13):1623-37.

Calarola, S. A., Leandersson, A. C., Bratt, G., Hinkula, J., Klinman, D. M., Weinhold, K. J., Sandstrom, E. and Wahren, B. (1999). Immune responses in asymptomatic HIV-1-infected patients after HIV-DNA immunization followed by highly active antiretroviral treatment *J. Immunol* 163(4):2330-8.

Connor, R., Sheridan, K., Ceraldini, D., Choe, S. & Landau, N. (1997). Changes in co-receptor use correlates with disease progression in HIV-1-infected individuals. *J Exp Med* 185, 621-628.

Durali D, Morvan J, Letoumeur F, Schmitt D, Guegan N, Dalod M, Saragosti S, Sicard D, Levy J P & Gomard E (1998). Cross-reactions between the cytotoxic T-lymphocyte responses of human immunodeficiency virus-infected African and European patients. *J Virol* 72:3547-53.

Ferrari G, Humphrey W, McElrath M J, Excler J L, Duliege A M, Clements M L, Corey L C, Bolognesi D P & Weinhold K J (1997). Clade B-based HIV-1 vaccines elicit cross-clade cytotoxic T lymphocyte reactivities in uninfected volunteers. *Proc Natl Aced Sci USA* 94(4):1396-401.

Hanke T, McMichael A J. (2000). Design and construction of an experimental HIV-1 vaccine for a year-2000 clinical trial in Kenya. *Nat Med* Sep.; 6(9):951-5.

HIV Molecular Immunology Database 1998: Korber B, Brander C, Koup R, Walker B, Haynes B, & Moore J, Eds. Theoretical Biology and Biophysics Group, Los Alamos National Laboratory, Los Alamos, N.M.

Klotman, M. E., Kim, S., Buchbinder, A., DeRossi, A., Baltimore, D. and Wong-Staal, F. (1991). Kinetics of expression of multiply spliced RNA in early human immunodeficiency virus type 1 infection of lymphocytes and monocytes. *Proc Natl Acad Sci USA.* 88(11):5011-5.

Kostrikis, L. G., Cao, Y., Ngai, H., Moore, J. P. & Ho, D. D (1996). Quantitative analysis of serum neutralization of human immunodeficiency virus type 1 from subtypes A, B, C, D, E, F, and I: lack of direct correlation between neutralization serotypes and genetic subtypes and evidence for prevalent serum-dependent infectivity enhancement *J. Virol.* 70, 445-458.

Koup R A, Safrit J T, Cao Y, Andrews C A, McLeod G, Borkowsky W, Farthing C, Ho D D (1994). Temporal association of cellular immune responses with the initial control of viremia in primary human immunodeficiency virus type 1 syndrome. *J Virol.* 68(7):4650-5.

Moore J P, Cao Y, Leu J, Qin L, Korber B & Ho D D (1996). Inter- and intraclade neutralizaton of human imunodeficiency virus type 1: genetic clades do not correspond to neutralization serotypes but partially correspond to gp120 antigenic serotypes. *J. Virol.* 70, 427-444.

Ogg G S, Kostense S, Klein M R, Jurriaans S, Hemann D, McMichael A J & Miedema F (1999). Longitudinal phenotypic analysis of human immunodeficiency virus type 1-specific cytotoxic T lymphocytes: correlation with disease progression. *J Virol;* 73(11):9153-60.

Peeters, M., Vincent R., Perret, J.-L., Lasky, M., Patrel, D., Liegeois, F., Courgnaud, V., Seng, R., Malton, T., Molinier, S. & Delaporte, E. (1999). Evidence for differences in MT2 cell tropism according to genetic subtypes of HIV-1: syncitium-induring variants seem rare among subtype C HIV-1 viruses. *J Acquir Imm Def Synd* 20, 115-121.

Richman, D. & Bozzette, S. (1994). The impact of the syncytium-inducing phenotype of human immunodeficiency virus on disease progression. *J Inf Dis* 169, 968-974.

Robertson D L, Anderson J P, Bradac J A, Carr J K, Foley B, Funkhouser R K, Gao R, Hahn B H, Kalish M L, Kuiken C, Learn G H Leitner T, McCutchan F, Osmanov S, Peeters M. Pieniazek D, Salminen M, Sharp P M, Wolinsky S, Korber B (2000). HIV nomenclature proposal. *Science* 7;288 (5463):55-6.

Rowland-Jones S L, Dong T, Fowke K R, Kimani J, Krausa P, Newell H, Blanchard T, Ariyoshi K, Oyugi J, Ngugi E, Bwayo J, MacDonald K S, McMichael A J & Plummer F A (1998). Cytotoxic T-cell responses to multiple conserved epitopes in HIV-resistant prostitutes in Nairobi. *J. Clin. Invest.* 102 (9): 1758-1765.

Scarlatti, G., Tresoldi, E., Bjorndal, A., Fredriksson, R., Colognesi, C., Deng, H., Malnati, M., Plebani, A, Siccardi, A., Littman, D., Fenyo, E. & Lusso, P. (1997). In vivo evolution of HIV-1 co-receptor usage and sensitivity to chemokina-mediated suppression. *Nat Med* 3, 1259-1265.

Schmitz J E, Kuroda M J, Santra S, Sasseville V G, Simon M A, Lifton M A, Racz P, Tenner-Racz K, Dalesandro M, Scallon B J, Ghrayeb J, Forman M A, Montefiori D C, Rieber E P, Letvin N L, Reimann K A (1999). Control of viremia in simian immunodeficiency virus infection by CD8+ lymphocytes. *Science* 5;283(5403):857-60.

Summary Report: National HIV seroprevalence survey of women attending public antenatal clinics in South Africa, 2000 (2001). Department of Health, Directorate: Health Systems Research & Epidemiology, April 2001.

Tscherning, C., Alaeus, A., Fredriksson, R., Bjorndal, A., Deng, H., Littman, D., Fenyo, E. M. & Alberts, J. (1998). Differences in chemokine co-receptor usage between genetic subtypes of HIV-1. *Virology* 241, 181-188.

The invention claimed is:

1. An isolated nucleic acid molecule comprising:
   (i) the nucleic acid sequence as set forth in nucleotides 1-588 of SEQ ID NO: 12;
   (ii) the nucleic acid sequence as set forth in nucleotides 30-618 of SEQ ID NO: 5;
   (iii) an RNA sequence corresponding to the nucleic acid sequence as set forth in SEQ ID NOs: 5 or 12; or
   (iv) a DNA sequence that is at least 98% similar to the nucleic acid sequence as set forth in SEQ ID NOs: 5 or 12, or an RNA sequence corresponding to the nucleic acid sequence that is at least 98% identical to the sequence as set forth in SEQ ID NOs: 5 or 12.

2. An isolated nucleic acid molecule according to claim 1, further comprising a tat sequence as set forth in any one of SEQ ID NOs: 1, 3, 9 or 10.

3. An isolated nucleic acid molecule according to claim 2, as set forth in SEQ ID NO: 15.

4. An isolated nucleic acid molecule comprising:
   (i) a human codon-optimized nucleic acid sequence having the sequence as set forth in nucleotides 1-588 of SEQ ID NO: 13, or the human codon-optimized nucleotide sequence of nucleotides 30-618 of SEQ ID NO: 5, as set forth in nucleotides 1-588 of SEQ ID NO: 13;
   (ii) an RNA sequence corresponding to the nucleic acid sequence as set forth in SEQ ID NO: 13; or
   (iii) a DNA sequence that is at least 98% similar to the nucleic acid sequence as set forth in SEQ ID NO: 13, or an RNA sequence corresponding to the nucleic acid sequence that is at least 98% identical to the sequence as set forth in SEQ ID NO: 13.

5. An isolated nucleic acid molecule according to claim 4, further comprising a tat sequence as set forth in any one of SEQ ID NOs: 1, 3, 9 or 10.

6. An isolated nucleic acid molecule according to claim 5, as set forth in SEQ ID NOs: 17 or 29.

7. An isolated nucleic acid molecule comprising the nucleic acid sequence as set forth in any one of SEQ ID NOs: 1, 3, 9, 10, 13, 15, 17, or 29.

* * * * *